US009470692B2

(12) United States Patent (10) Patent No.: US 9,470,692 B2
Baumann et al. (45) Date of Patent: Oct. 18, 2016

(54) MASS SPECTROMETRIC ANALYSIS

(75) Inventors: Christian Baumann, Cobham (GB); Helen Byers, Cobham (GB); Peter Schulz-Knappe, Cobham (GB); Malcolm Ward, Cobham (GB)

(73) Assignee: ELECTROPHORETICS LIMITED, Cobham Surrey (GB)

( * ) Notice: Subject to any disclaimer, the term of this patent is extended or adjusted under 35 U.S.C. 154(b) by 539 days.

(21) Appl. No.: 12/994,400

(22) PCT Filed: May 18, 2009

(86) PCT No.: PCT/EP2009/056010
§ 371 (c)(1),
(2), (4) Date: Jan. 18, 2011

(87) PCT Pub. No.: WO2009/141310
PCT Pub. Date: Nov. 26, 2009

(65) Prior Publication Data
US 2011/0111513 A1 May 12, 2011

(30) Foreign Application Priority Data
May 23, 2008 (GB) .................................. 0809488.0

(51) Int. Cl.
*G01N 33/00* (2006.01)
*H01J 49/00* (2006.01)
*G01N 33/68* (2006.01)

(52) U.S. Cl.
CPC .. *G01N 33/6848* (2013.01); *Y10T 436/143333* (2015.01)

(58) Field of Classification Search
None
See application file for complete search history.

(56) References Cited

U.S. PATENT DOCUMENTS

| 6,824,981 B2 | 11/2004 | Chait et al. | |
|---|---|---|---|
| 2004/0219685 A1 | 11/2004 | Pappin | |
| 2006/0183238 A1* | 8/2006 | Nimkar et al. | 436/111 |

FOREIGN PATENT DOCUMENTS

| EP | 1736480 A1 | 12/2006 |
|---|---|---|
| WO | PCT/GB94/01675 A1 | 2/1995 |
| WO | PCT/US97/01046 A2 | 7/1997 |
| WO | PCT/US97/01070 A1 | 7/1997 |
| WO | PCT/US97/01304 A2 | 7/1997 |
| WO | PCT/US97/22639 A1 | 6/1998 |
| WO | PCT/GB98/00127 A1 | 7/1998 |
| WO | 00/02895 A1 | 1/2000 |
| WO | 01/68664 A2 | 9/2001 |
| WO | 03/025576 A2 | 3/2003 |
| WO | 2006/084130 A | 8/2006 |
| WO | 2007/012849 A | 2/2007 |
| WO | WO 2007/031717 * | 3/2007 |

OTHER PUBLICATIONS

International Preliminary Report on Patentability issued for PCT/EP2009/056010 on Nov. 23, 2010.*
Kiyonami et al., "Identification and Quantification of iTRAQ Labeled Peptides on the Finnigan LTQ using MS/MS and MS3," retrieved from http://www.thermo.com/eThermo/CMA/PDFs/Various/File_27402.pdf; created online Sep. 14, 2005; modified Oct. 11, 2005.*
A print-out retrieved from http://www.ehow.com/how_8429035_publication-date-website.html on Sep. 30, 2013.*
The Apr. 3, 2013 e-mail message from Thermo Scientific Website Support.*
Chang et al., "Implementation of Multiplexed iTRAQ Quantitation Tags on Ion Trap Instruments via MS3," Poster 569, ASMS 2005, San Antonio, TX.*
Beausoleil et al., "Large-scale characterization of HeLa cell nuclear phosphoproteins," PNAS, 2004, vol. 101, No. 33, pp. 12130-12135.*
Kiyonami et al., "Protein Identification and Quantification. Tutorial: Developing a Workflow on the Finnigan LTQ for iTRAQ Labeled Peptides," Genetic Engineering News, 2005, vol. 25, No. 20, pp. 29-30.*
Proceedings of 53rd ASMS Conference Jun. 5-9, 2005, San Antonio, TX, title pages.*
Ting et al., "MS3 eliminates ratio distortion in isobaric multiplexed quantitative proteomics," Nature Methods, 2011, vol. 8, pp. 937-940.*
Kawano et al., "Idnetification of drugs by ultra fast liquid chormoatography/electrospray ionization-quadrupole ion trap/time-of-flight mass spectromoetry," J. of Liquid Chromatography and Related Technologies, Jan. 2008, Taylor and Francis Inc., US, pp. 23-37, vol. 31, No. 1.
Tuynman, Antonin, Article 94(e) EPC Communication, European Patent Office, Dec. 7, 2011.
Wu et al., "Triple mass spectromoetry (MS/MS/MS) with a floated collision cell in a four-sector tandem mass spectrometer," Organic Mass Spectrometry, Oct. 1991, pp. 908-911, vol. 26, No. 10.
Marcos N. Eberlin et al.: "Novel [3+2] 1, 3-Cycloaddition of the Ionized Carbonyl Ylide+CH 2 OCH 2—with Carbonyl Compounds in the Gas Phase", Journal of the American Chemical Society, vol. 119, No. 15, Apr. 1, 1997, XP55041280, ISSN: 0002-7863, DOI: 10.1021/ja9514151, pp. 3550-3557.
Antonin Tuynman, Office Action, European Patent Office, Oct. 23, 2012, pp. 1-4.
Gygi et al., Quantitative Analysis of Complex Protein Mixtures using Isotope-Coded Affinity Tags, Nature Biotechnology, Oct. 1999, vol. 17, pp. 994-999.
Lloyd-Williams et. al., Convergent Solid-Phase Peptide Synthesis, Tetrahedron, 1993, vol. 49, No. 48, pp. 11065-11133.
Syka et al., Peptide and Protein Sequence Analysis by Electron Transfer Dissociation Mass Spectrometry, PNAS, Jun. 29, 2004, vol. 101, No. 26, pp. 9528-9533.

(Continued)

*Primary Examiner* — Galina Yakovleva
(74) *Attorney, Agent, or Firm* — Arent Fox LLP

(57) ABSTRACT

The disclosure provides a method for assaying for a target analyte, comprising providing a plurality of samples which may comprise the target analyte, wherein each sample is differentially labelled with a mass label or a combination of mass labels, wherein the mass labels are from a set of mass labels, wherein each mass label is an isobaric mass label comprising a mass spectrometrically distinct mass marker group, such that the samples can be distinguished by mass spectrometry and determining from the mass spectrum the quantity of the target analyte in each sample.

37 Claims, 42 Drawing Sheets

(56) References Cited

OTHER PUBLICATIONS

Thompson et al., Tandem mass tags: a novel quantification strategy for comparative analysis of complex protein mixtures by MS/MS, Apr. 15, 2003, Analytical Chemistry, vol. 75, No. 8, pp. 1895-1904.
Maskos et al., Oligonucleotide hybridisations on glass supports: a novel linker for oligonucleotide synthesis and hybridisation properties of oligonucleotides synthesised in situ, Nucleic Acids Research, 1992, vol. 20, No. 7, pp. 1679-1684.
Natarajan et al., Site-Specific Biotinylation; A Novel Approach and its Application to Endothelin-1 Analogs and PTH-Analog, Int. J. Peptide Protein Res., 1992, vol. 40(6), pp. 567-574.
Geahlen et. al., A General Method for Preparation of Peptides Biotinylated at the Carboxy Terminus, Analytical Biochemistry, 1992, vol. 202(1), pp. 68-70.
Sawutz et al., Synthesis and Molecular Characterization of a Biotinylated Analog of [Lys]bradykinin, Peptides, 1991, vol. 12(5), pp. 1019-1012.
Pappin, Darryl J., "Multiplexed Protein Quantitation in *Saccharomyces cerevisiae* Using Amine-Reactive Isobaric Tagging Reagents," MCP Papers in Press, published on Sep. 28, 2004 as Manuscript M400129-MCP200, pp. 1-74.
Tuynman, Antonin, International Search Report, PCT/EP09/056010, European Patent Office, Sep. 1, 2009.

\* cited by examiner

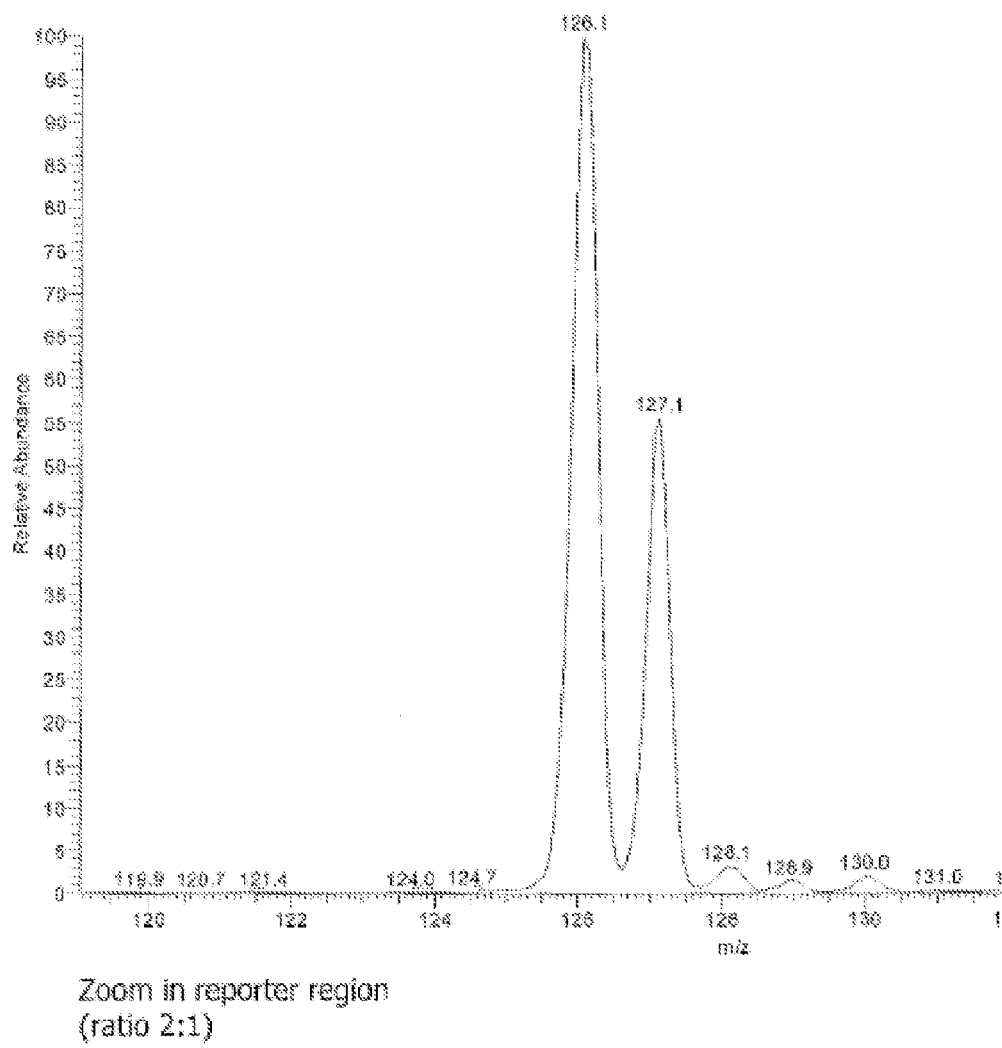

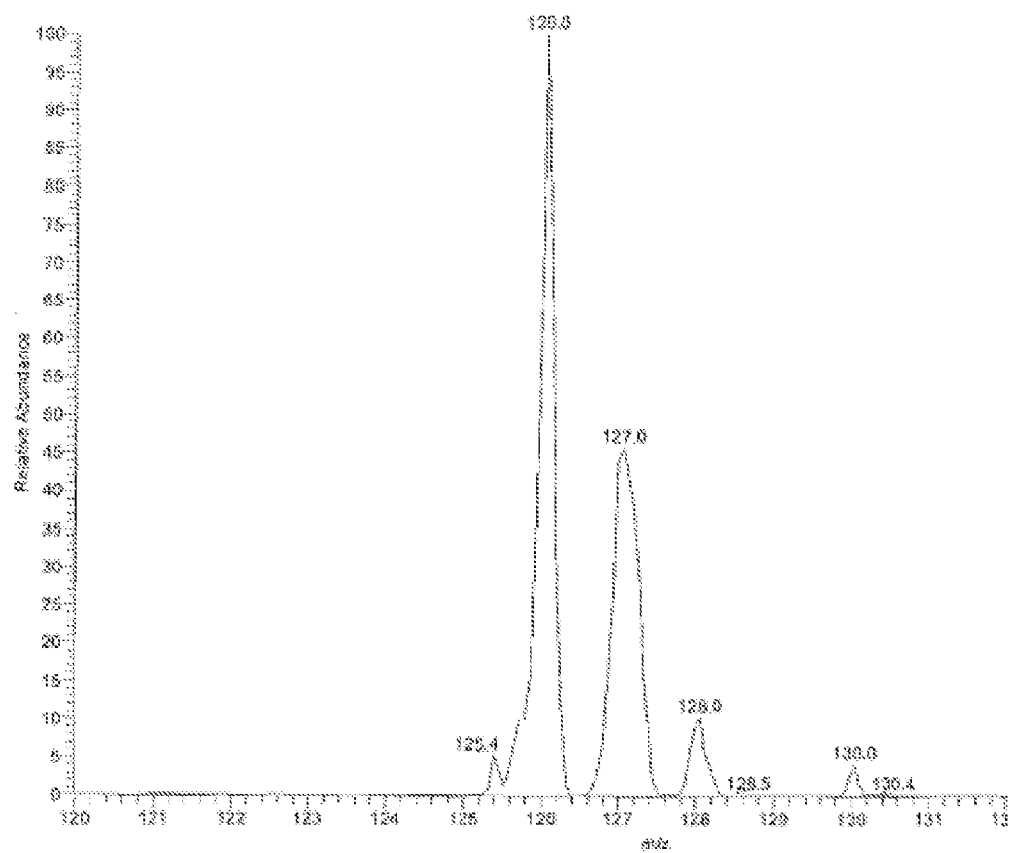

Figure 3

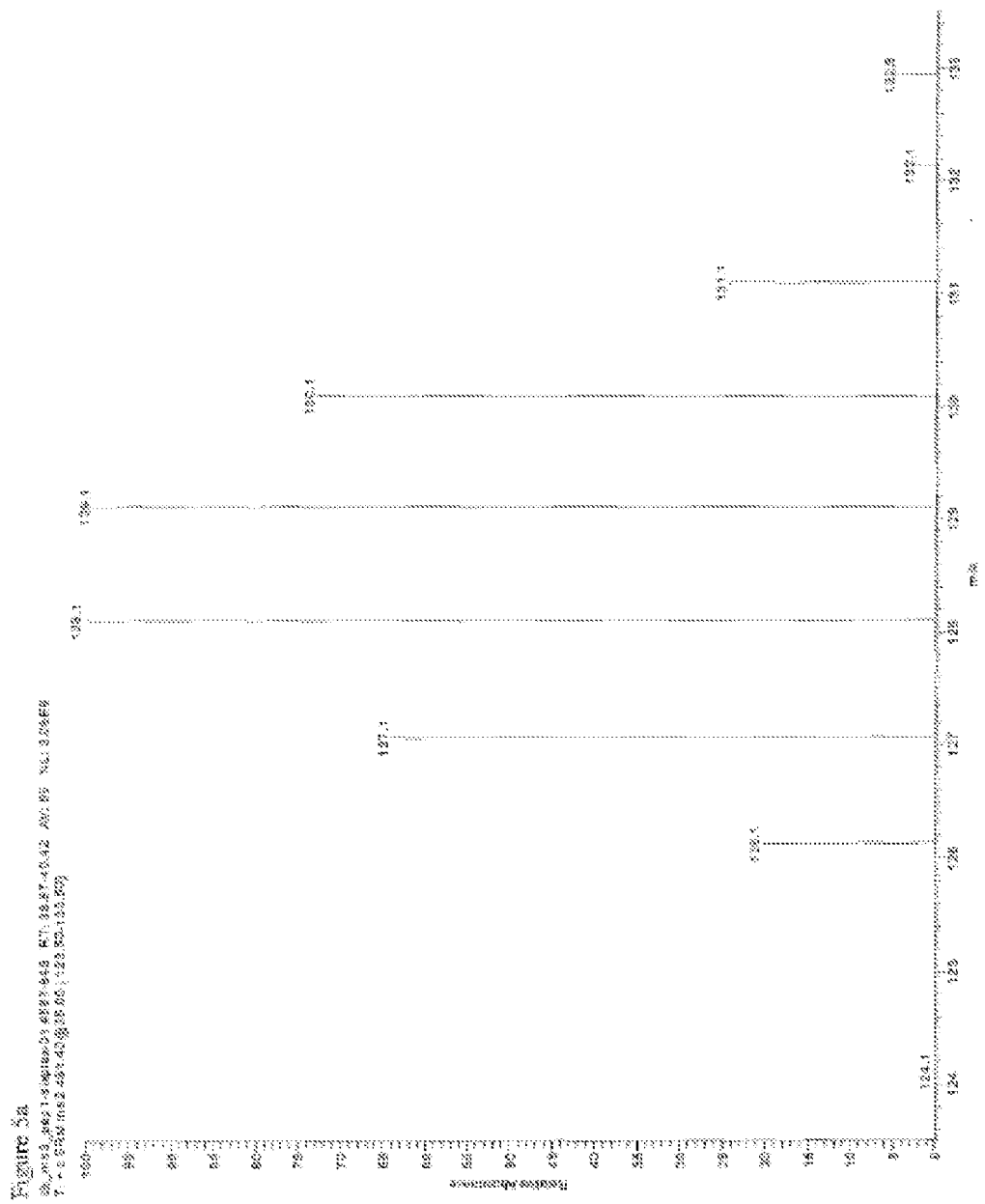

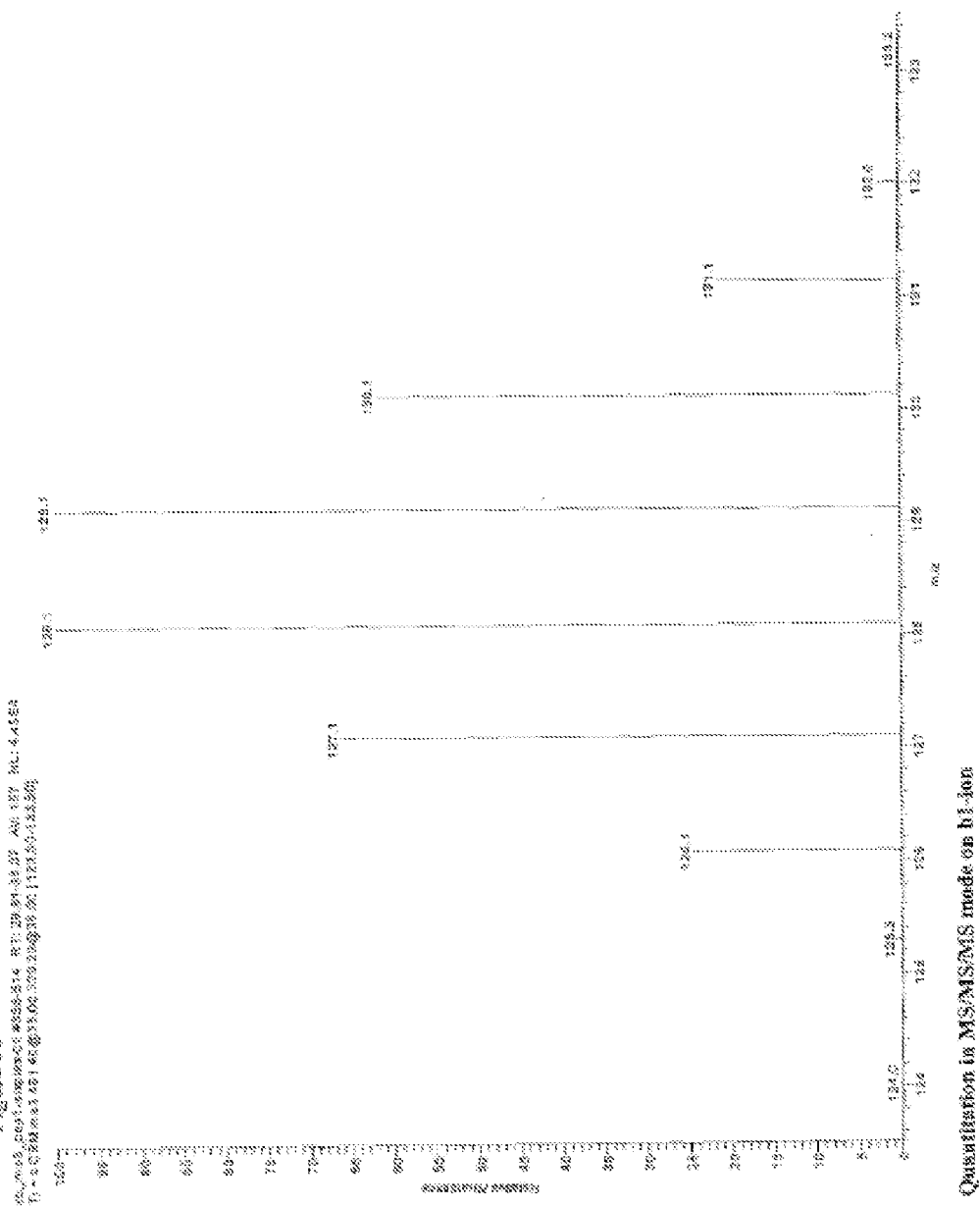

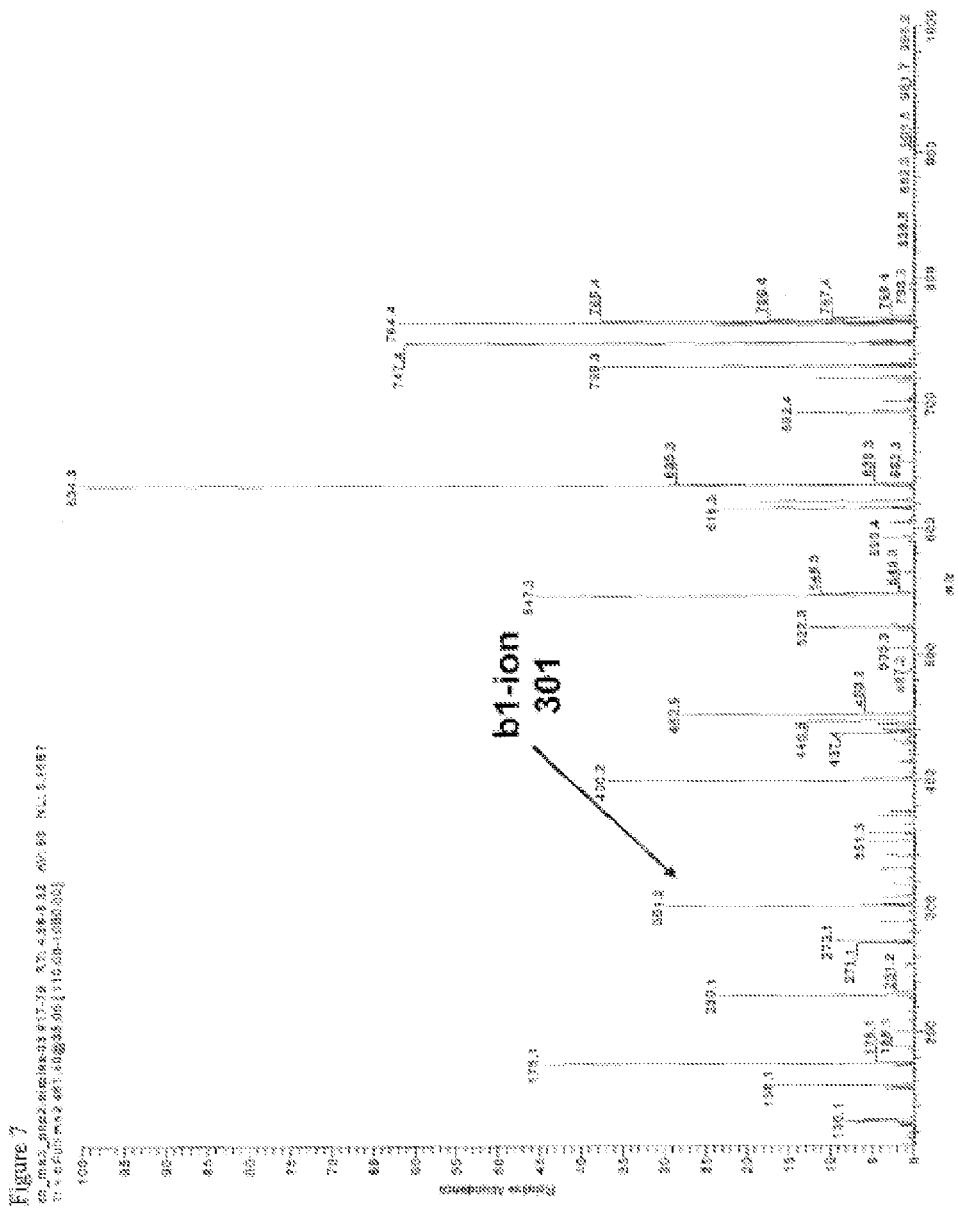

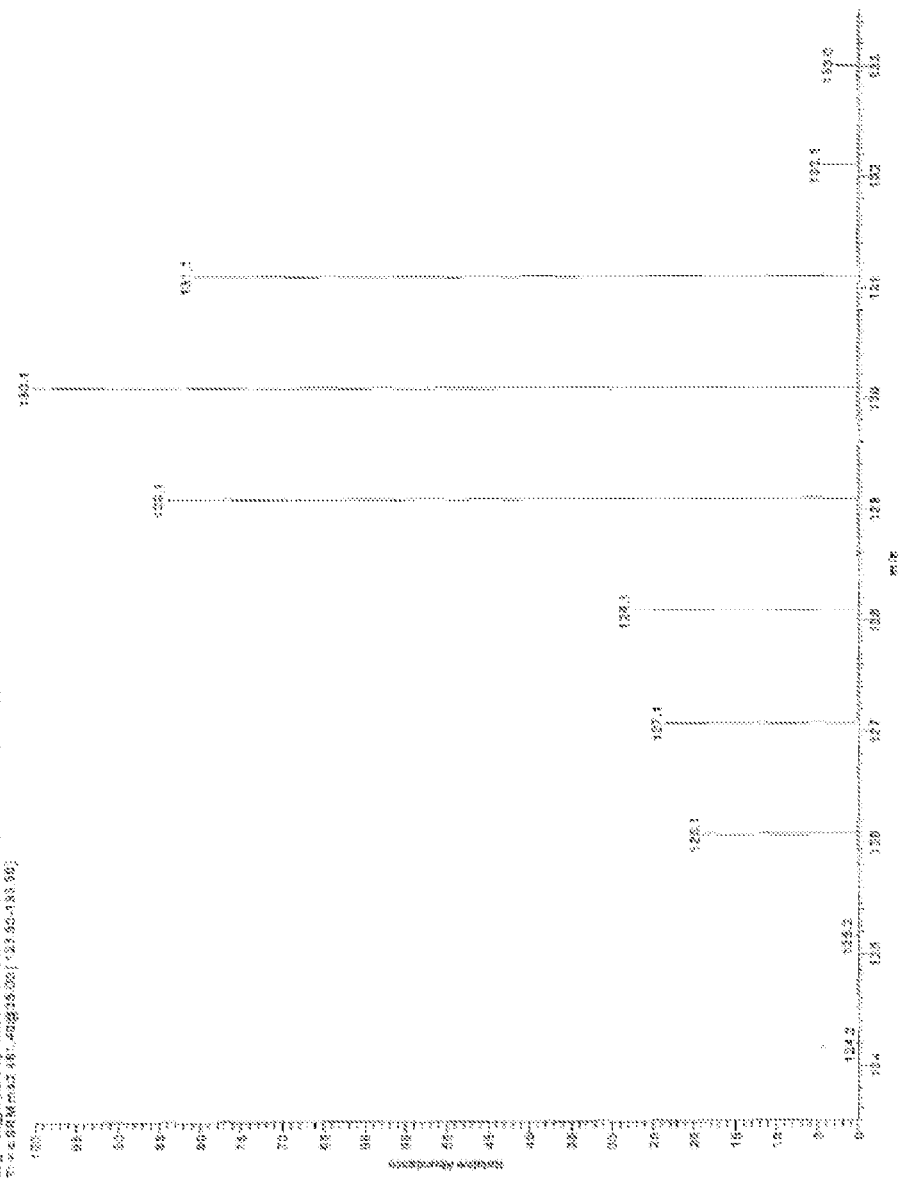

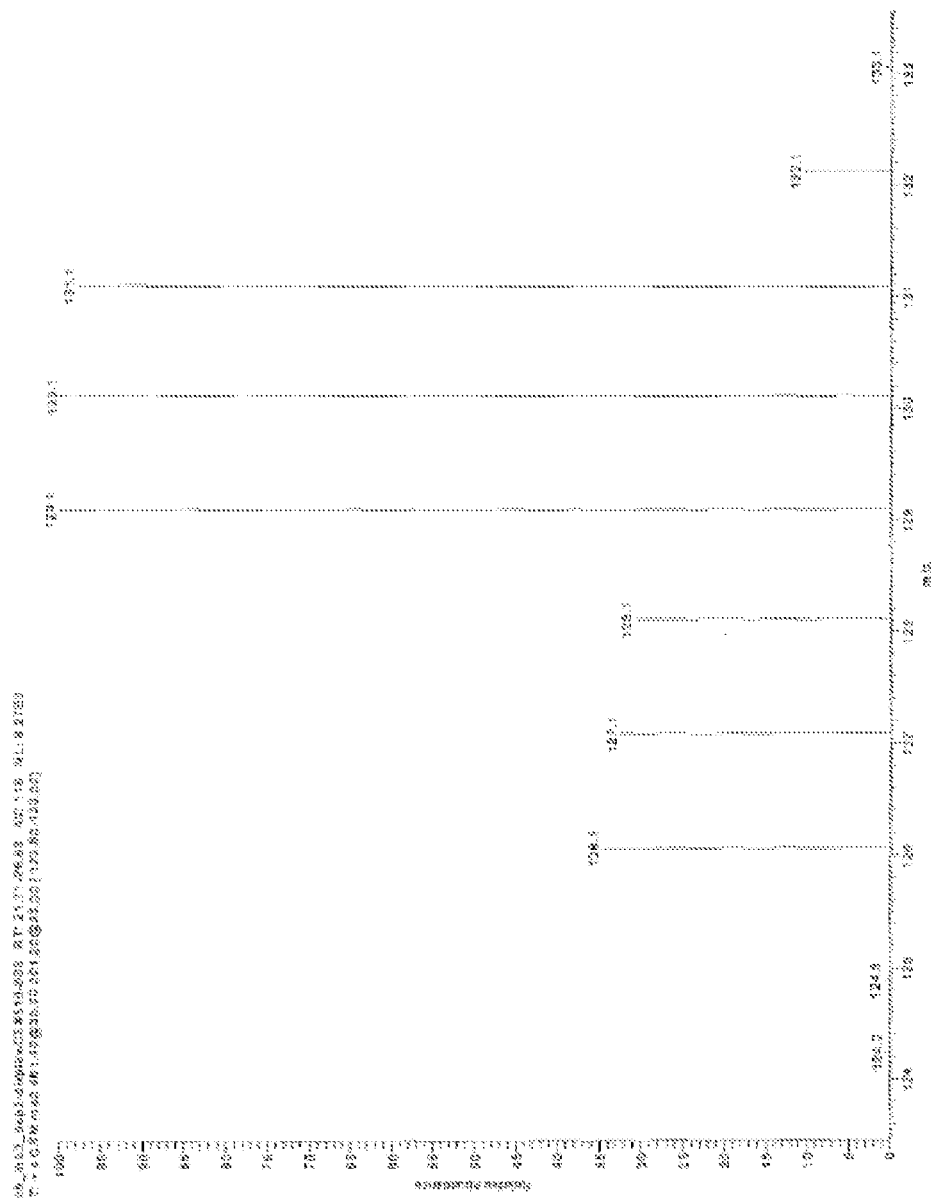

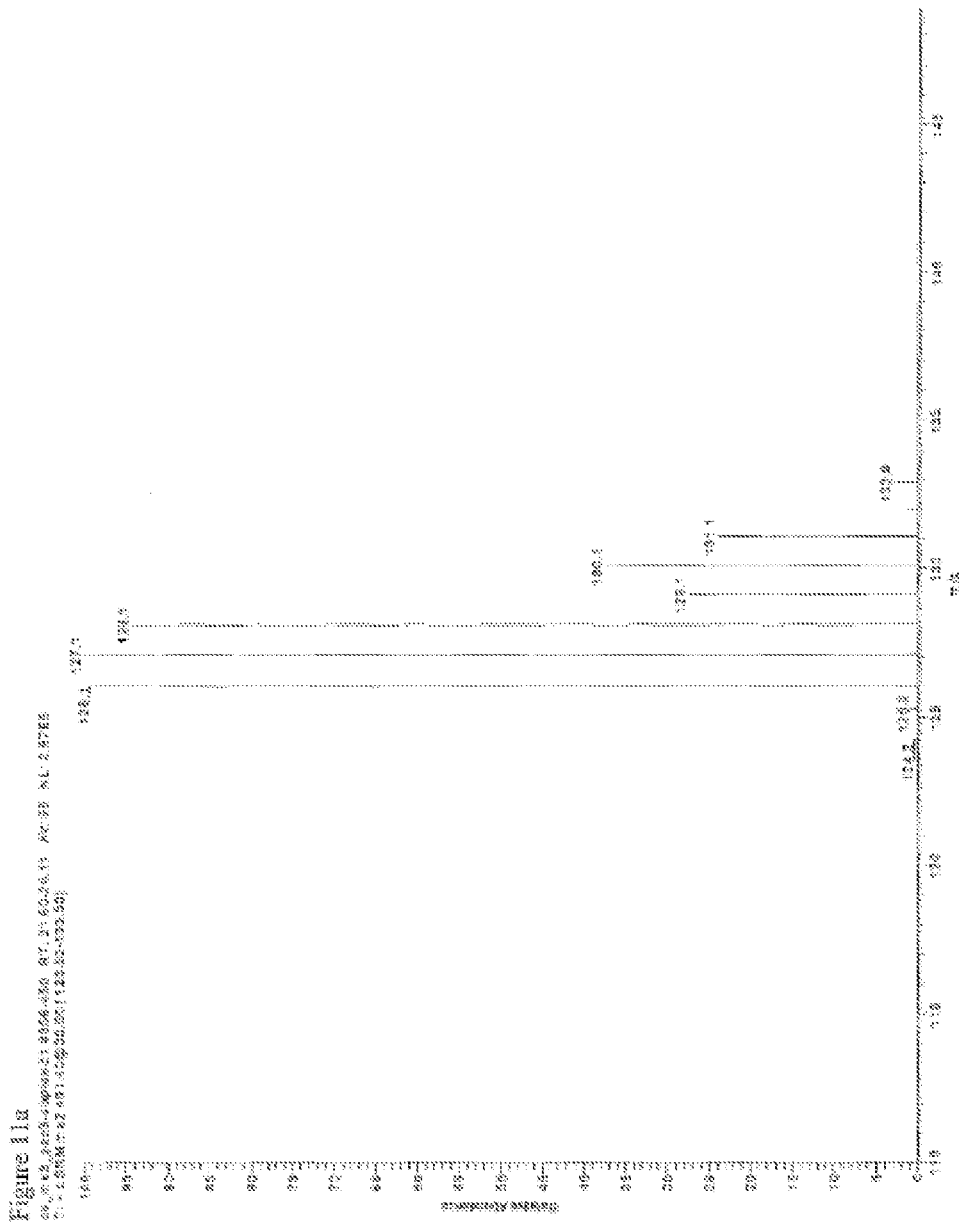

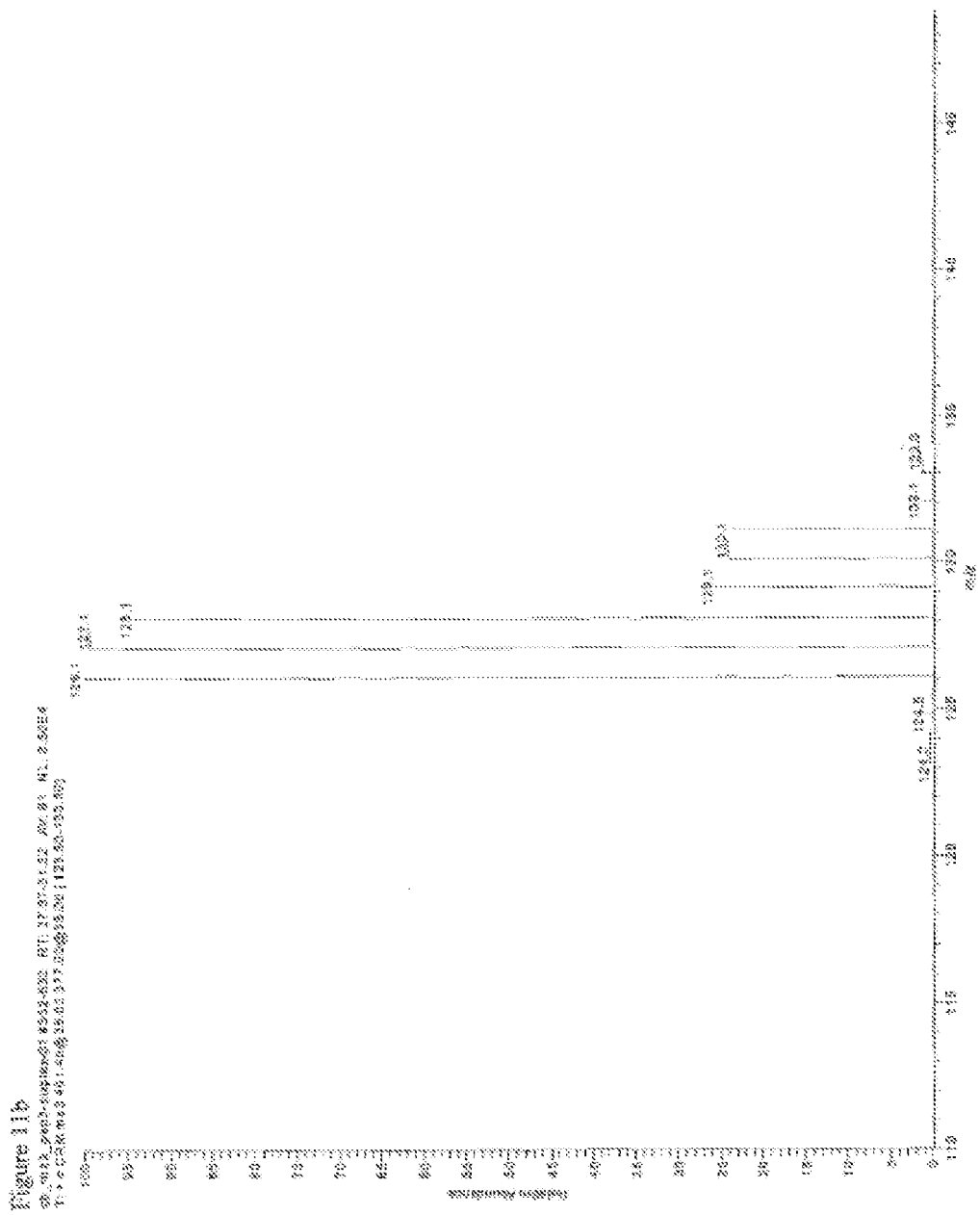

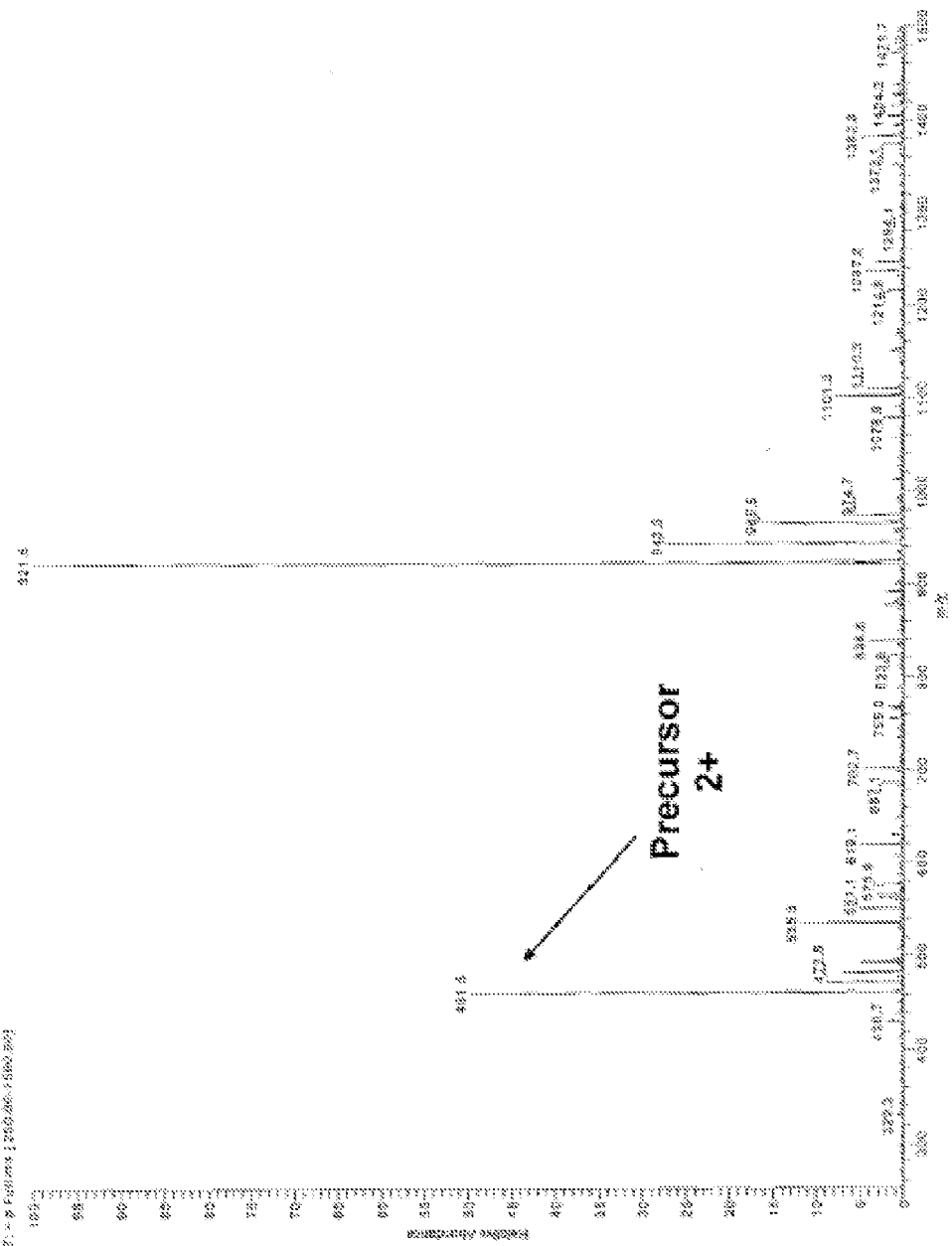

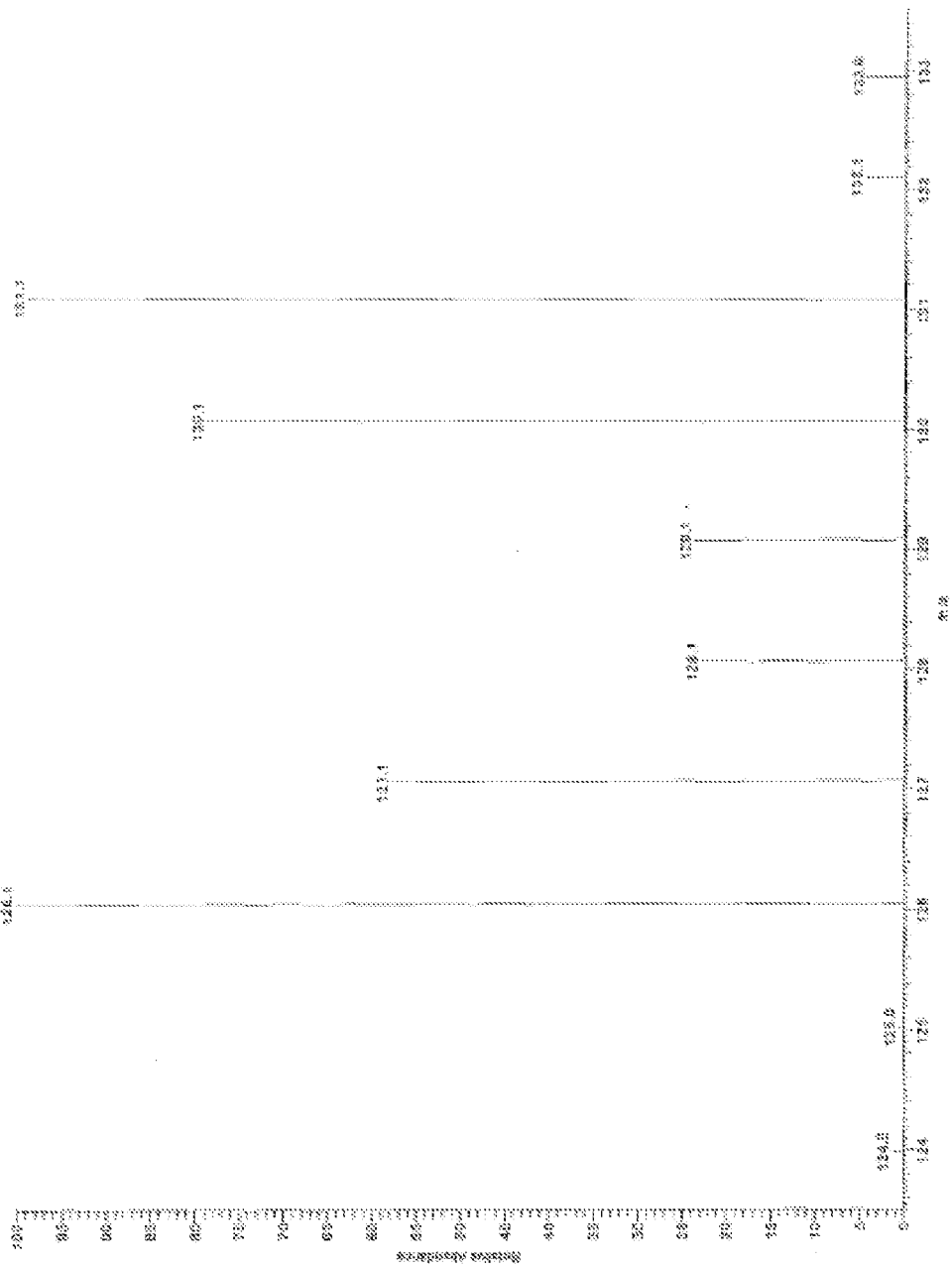

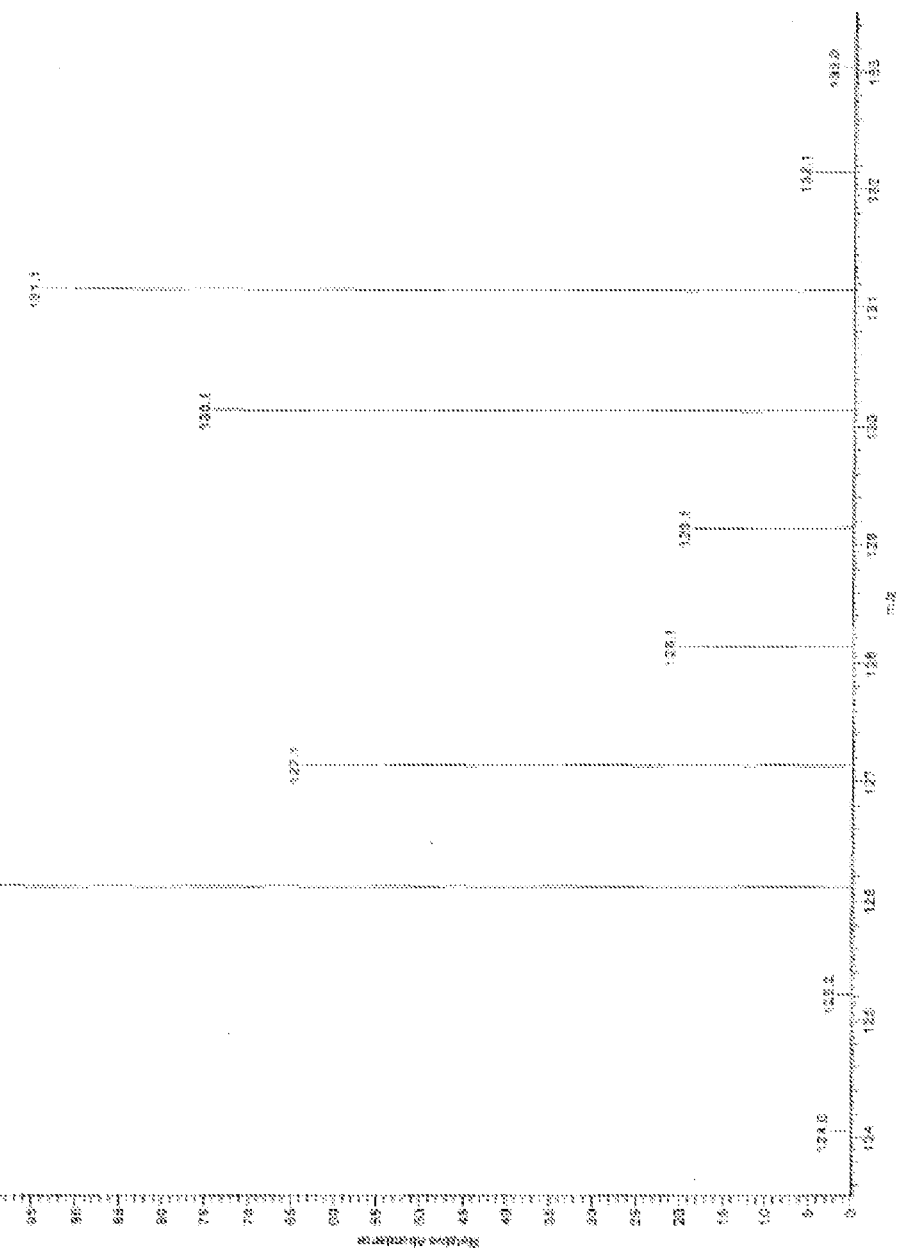

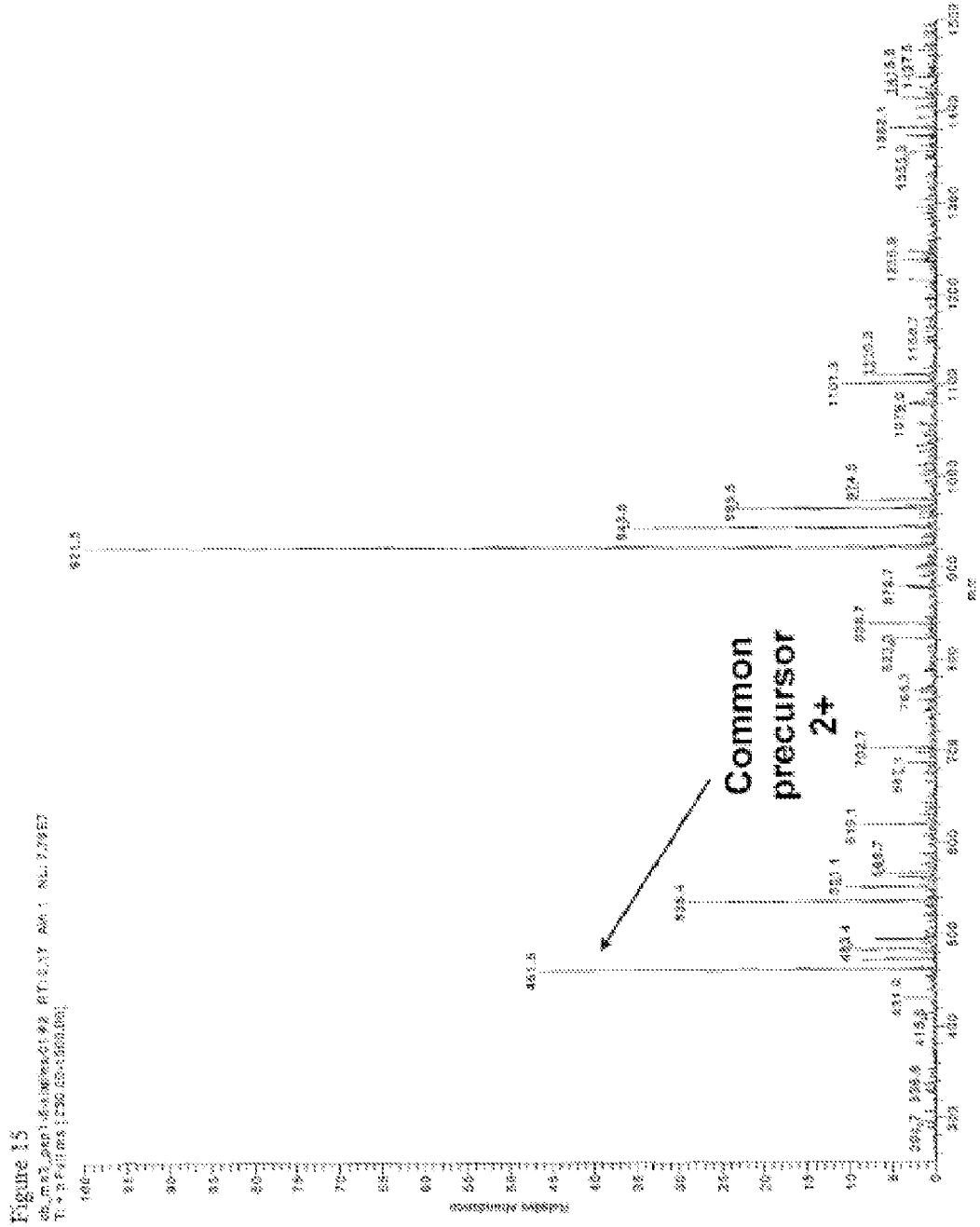

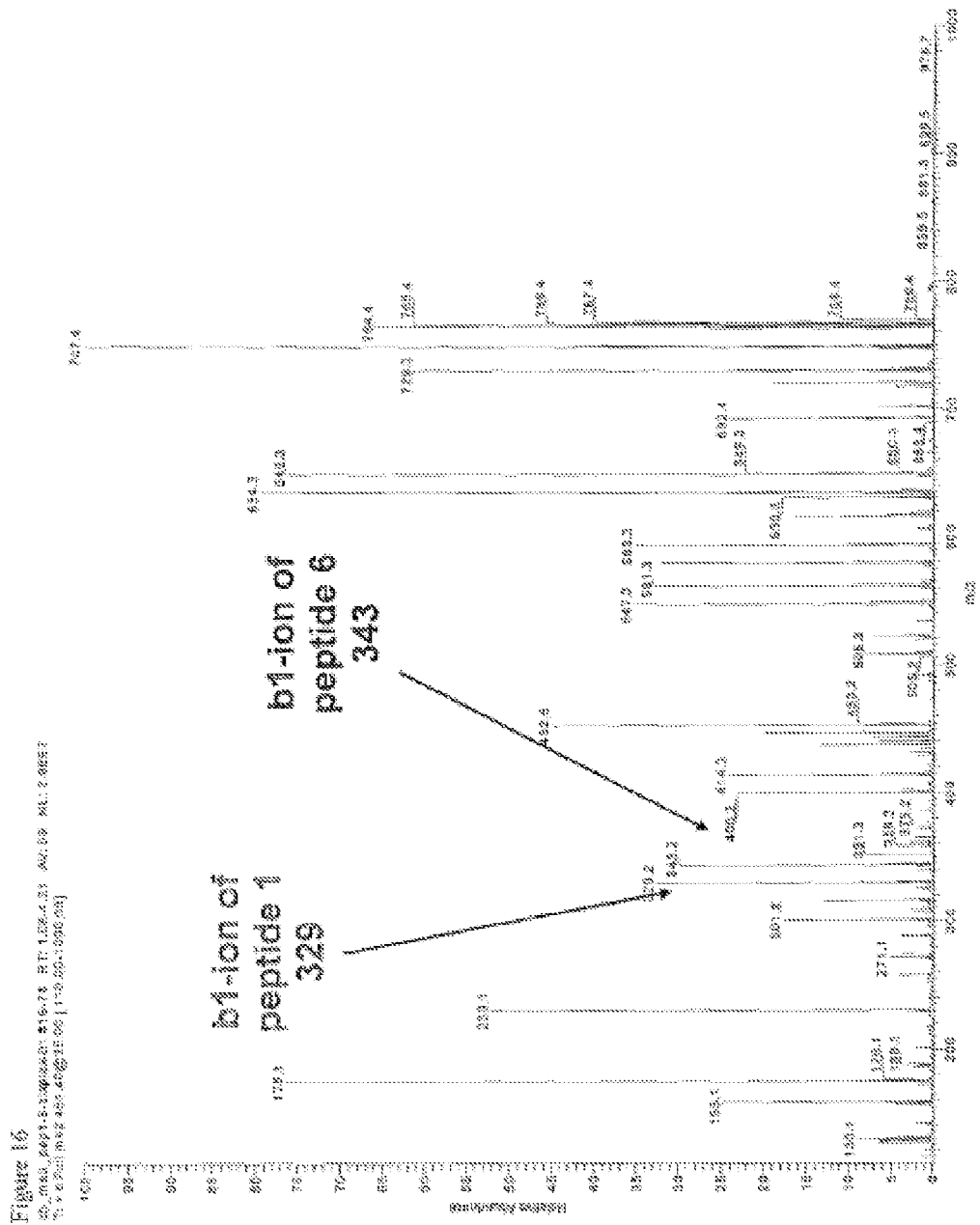

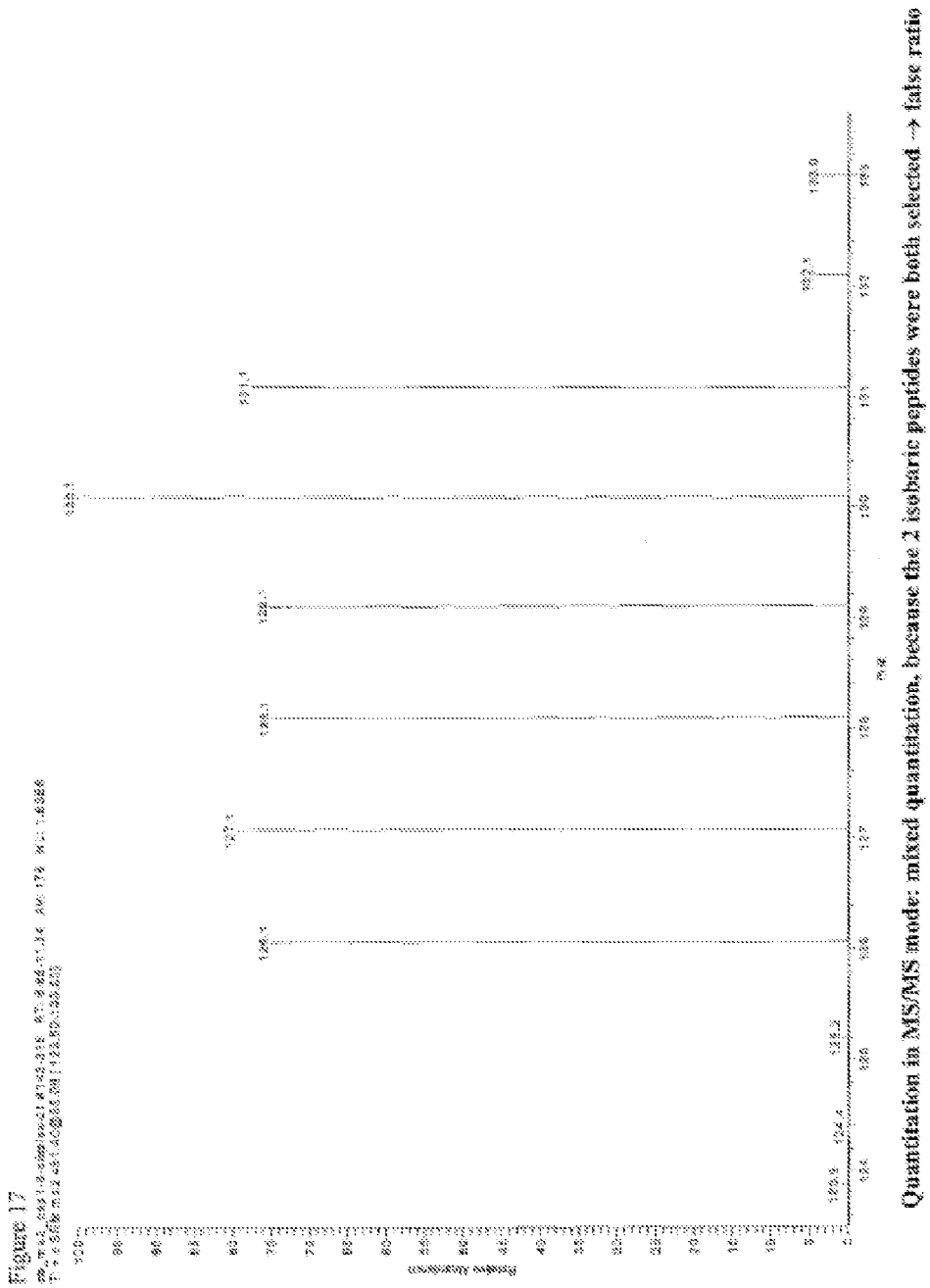

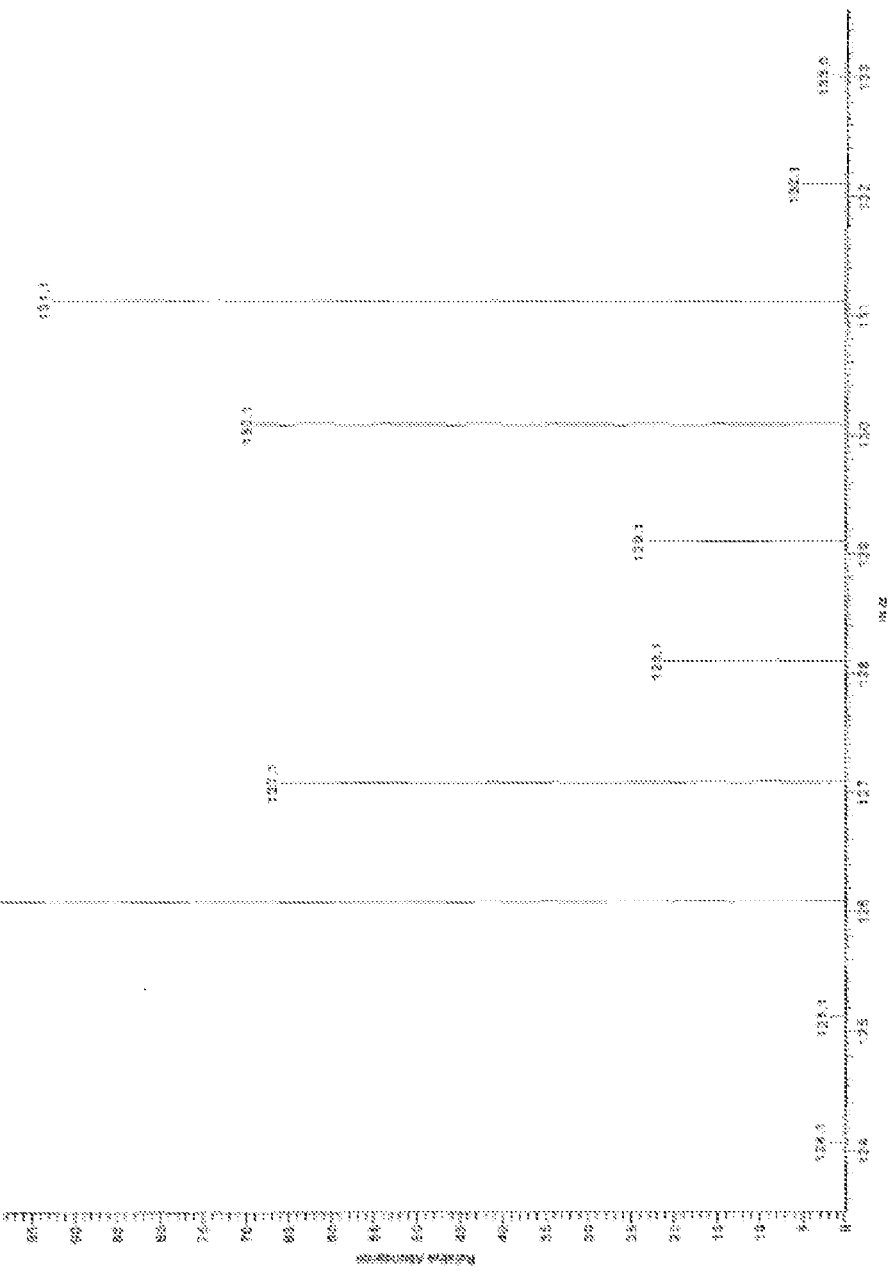

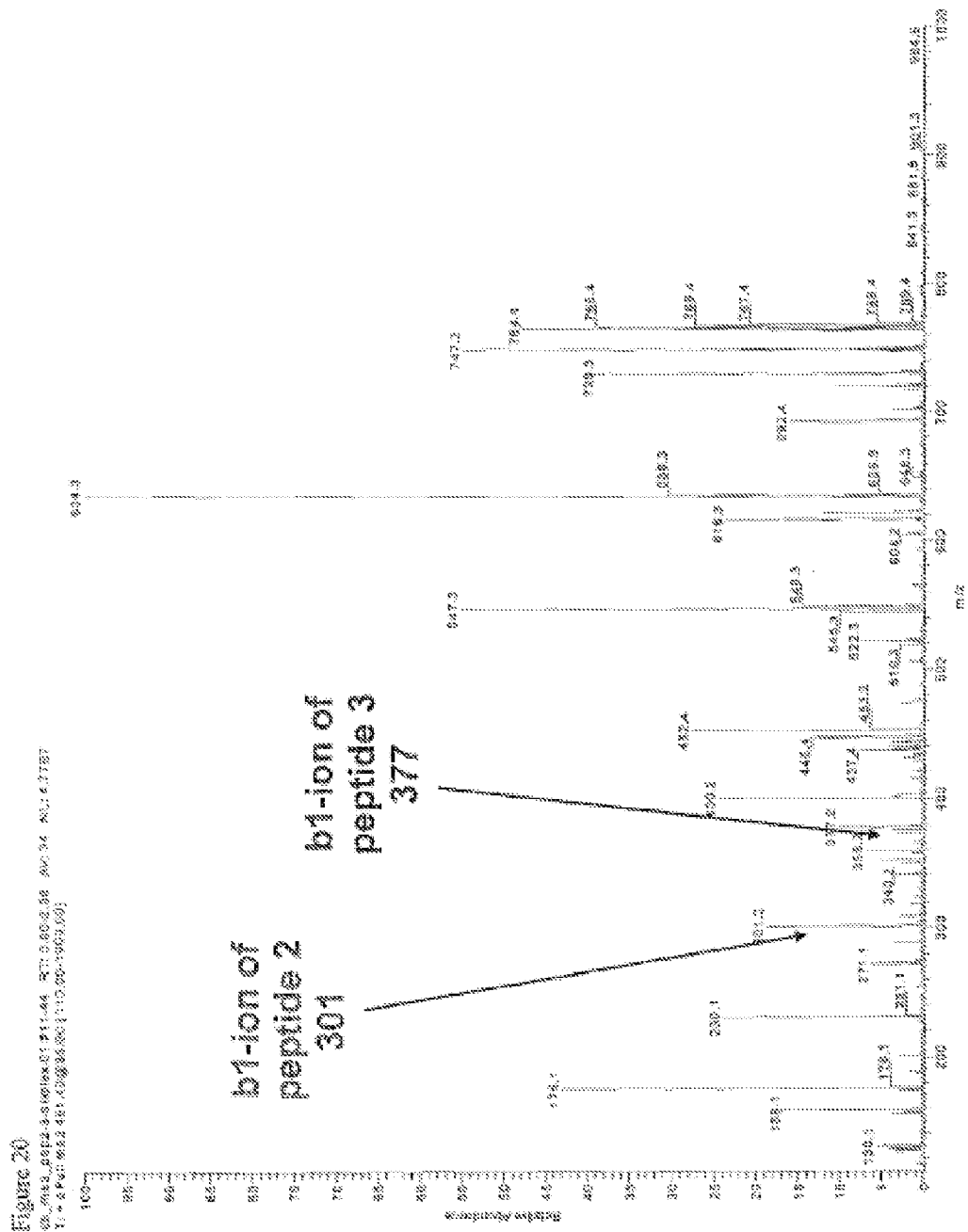

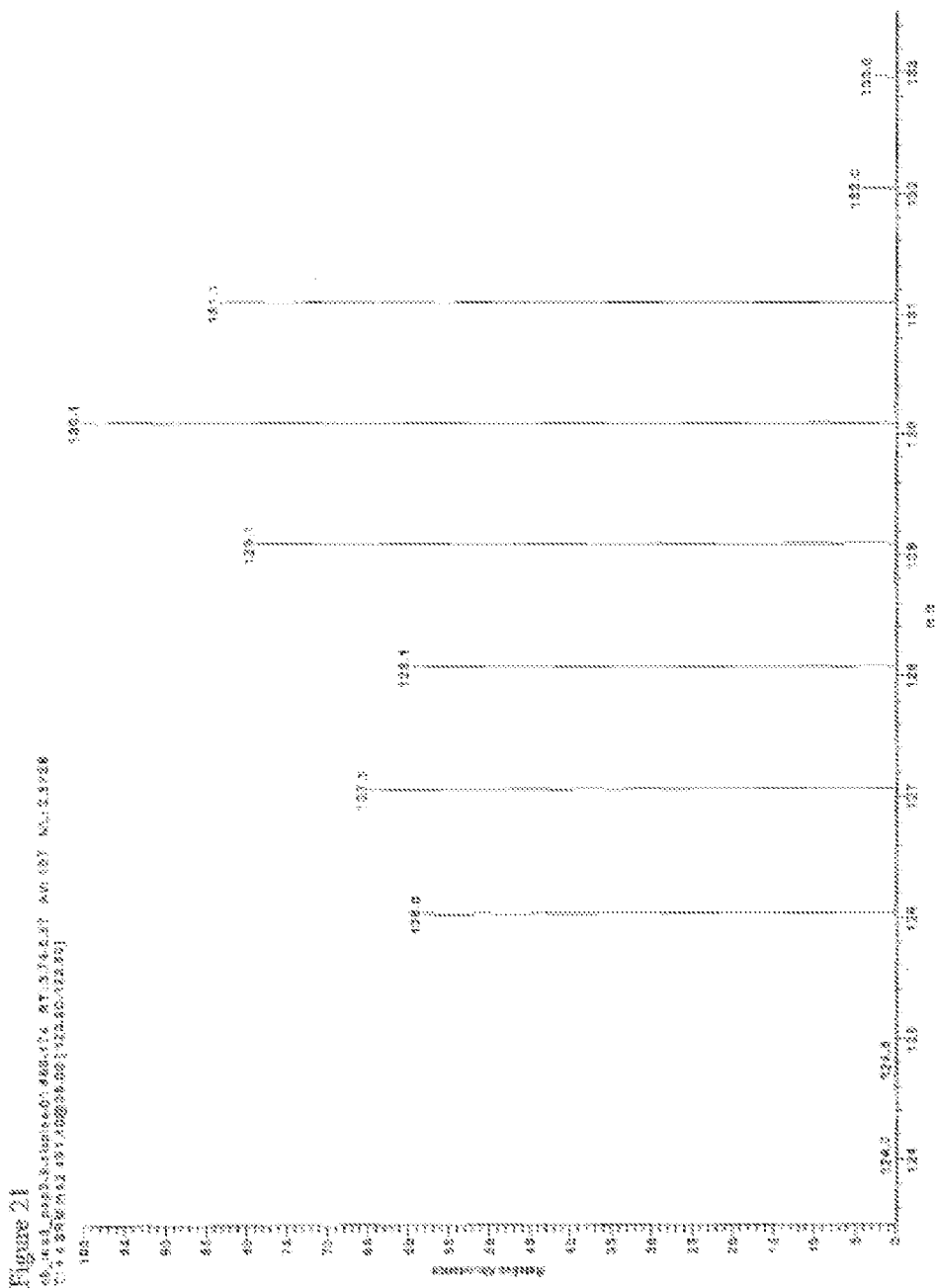

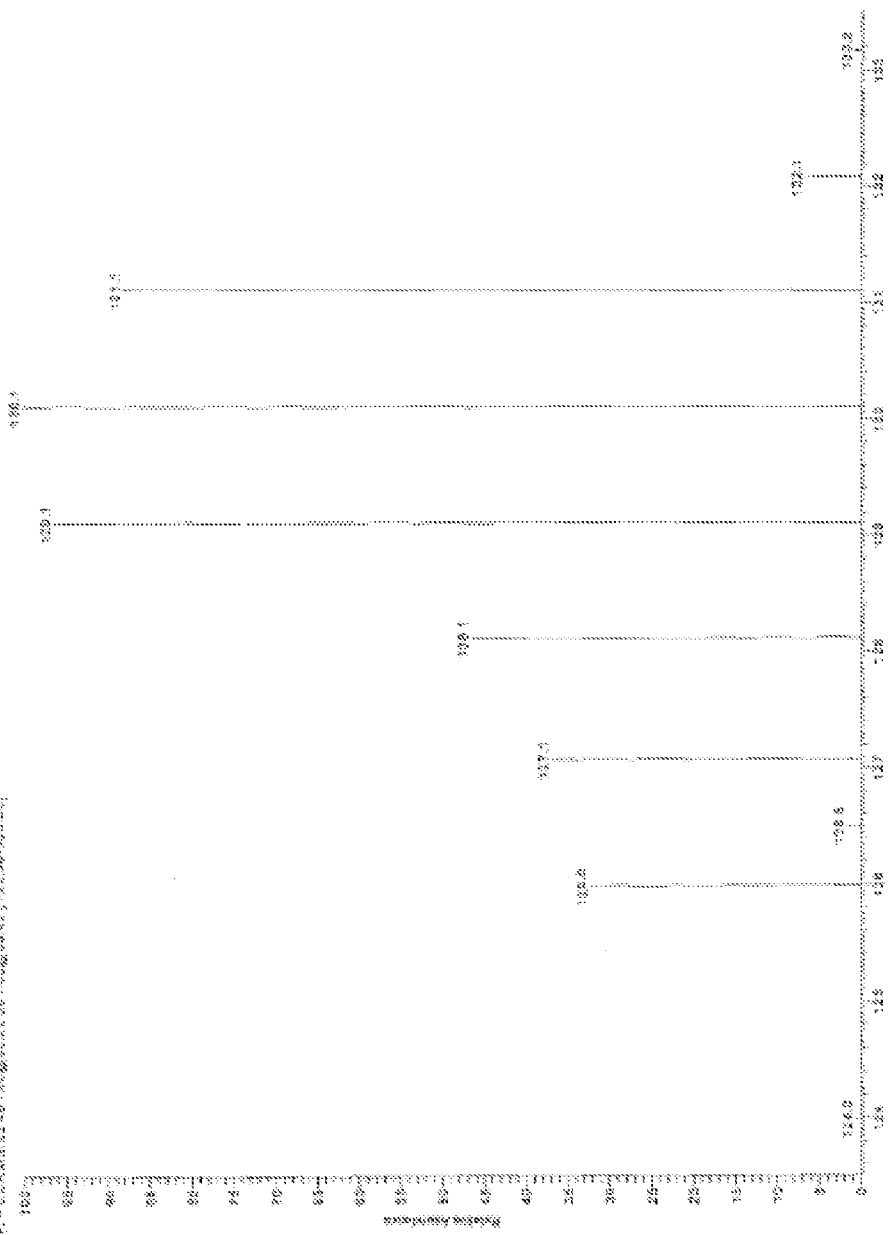

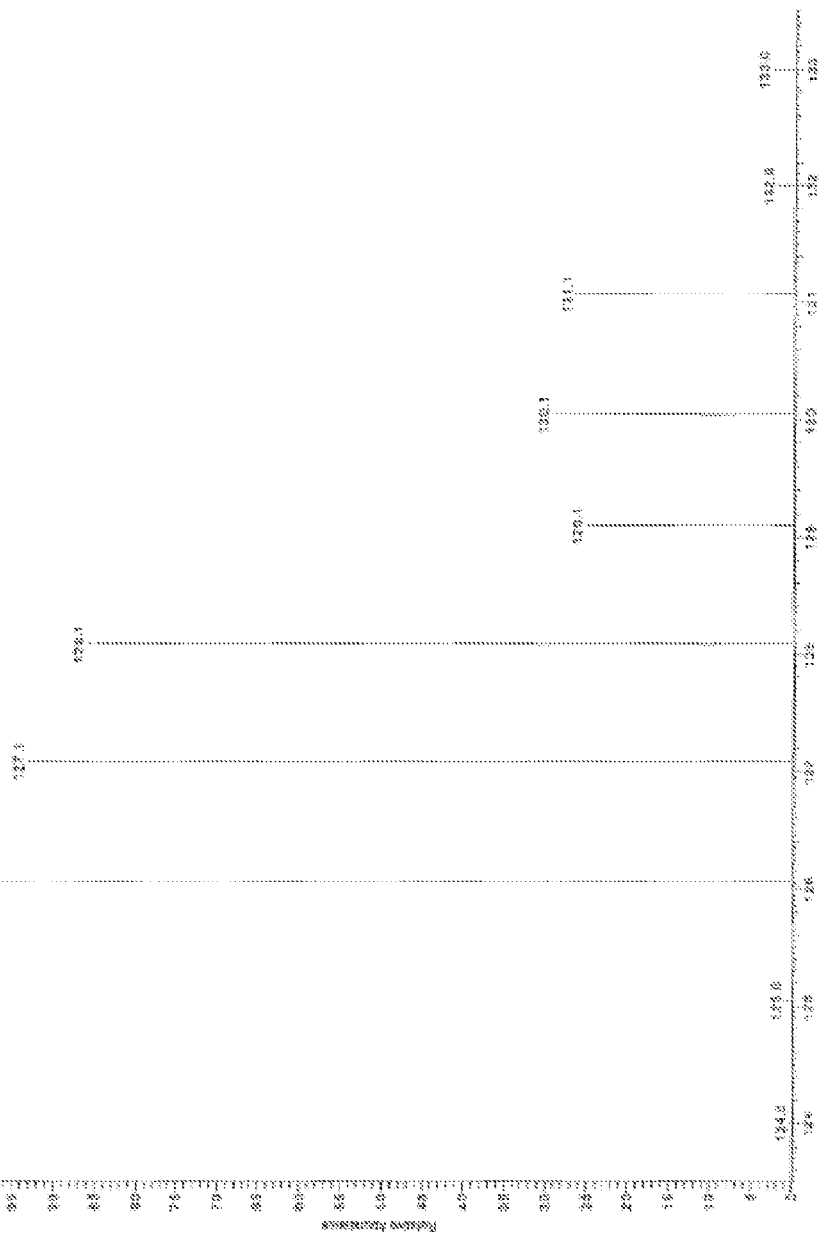

SEQUENCE LISTING

<160> NUMBER OF SEQ ID NOS: 21

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Val Ala Thr Val Ser Leu Pro Arg
1               5

<210> SEQ ID NO 2
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ala Phe Ser Leu Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Val Phe Ser Leu Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Ala Val Ser Leu Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Phe Ser Val Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Glu Phe Ala Glu Val Ser Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Leu Glu Pro Thr Leu Lys
```

```
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Val Asn Glu Val Thr Glu Phe Ala Lys
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Val Thr Asp Leu Thr Lys
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Pro Asp Tyr Ser Val Val Leu Leu Leu Arg
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Leu Pro Ala Pro Ile Glu Lys
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 13

Ser Ala Ser Asp Leu Trp Asp Asn Leu Lys
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Leu Gly Gly His Leu Asp Ala Lys
1               5

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Leu Ser Val Pro Tyr Val Ile Val Pro Leu Lys
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Val His Val Glu Glu Pro His Thr Glu Thr Val Arg
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Gln Asn Ala Leu Leu Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Thr Val Asp Lys Thr Met Thr
1               5

<210> SEQ ID NO 19

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Thr Leu Met Ile Ser Arg
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Glu Phe Ala Lys
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Val Asn Glu Val Thr Glu
1               5
```

MASS SPECTROMETRIC ANALYSIS

CROSS REFERENCE TO RELATED APPLICATIONS

This application is a U.S. National Stage Application filed under 35 U.S.C. §371 and claims priority to International Application No. PCT/EP09/056010, filed May 18, 2009, which application claims priority to Great Britain Application No. 0809488.0, filed on May 23, 2008, the disclosures of which are incorporated herein by reference.

SEQUENCE LISTING

The instant application contains a Sequence Listing which has been submitted in ASCII format via EFS-Web and is hereby incorporated by reference in its entirety. Said ASCII copy, created on Dec. 14, 2012, is named 33945006.txt and is 4,946 bytes in size.

FIELD OF THE INVENTION

This invention relates to a method of assaying a target analyte by mass spectrometry, particularly biomolecules such as nucleic acids and proteins. Specifically the invention relates to a method of multiplexed tandem mass spectrometry using isobaric mass labels. The present invention also relates to a mass spectrometric device for assaying one or more target analytes.

BACKGROUND OF THE INVENTION

Various methods of labelling molecules of interest are known in the art, including radioactive atoms, fluorescent dyes, luminescent reagents, electron capture reagents and light absorbing dyes. Each of these labelling systems has features which make it suitable for certain applications and not others. More recently there has been development in the area of mass spectrometry as a method of detecting labels that are cleavably attached to their associated molecule of interest.

For many applications such as nucleic acid analysis, the structure of the analyte can be determined from indirect labelling. This is advantageous particularly with respect to the use of mass spectrometry because complex biomolecules such as DNA have complex mass spectra and are detected with relatively poor sensitivity. Indirect detection means that an associated label molecule can be used to identify the original analyte, where the label is designed for sensitive detection and a simple mass spectrum. Simple mass spectra mean that multiple labels can be used to analyse multiple analytes simultaneously.

PCT/GB98/00127 describes arrays of nucleic acid probes covalently attached to cleavable labels that are detectable by mass spectrometry which identify the sequence of the covalently linked nucleic acid probe. The labelled probes of this application have the structure Nu-L-M where Nu is a nucleic acid covalently linked to L, a cleavable linker, covalently linked to M, a mass label. Preferred cleavable linkers in this application cleave within the ion source of the mass spectrometer. Preferred mass labels are substituted poly-aryl ethers. This application discloses a variety of ionisation methods and analysis by quadrupole mass analysers, Time of Flight (TOF) analysers and magnetic sector instruments as specific methods of analysing mass labels by mass spectrometry.

PCT/GB94/01675 discloses ligands, and specifically nucleic acids, cleavably linked to mass tag molecules. Preferred cleavable linkers are photo-cleavable. This application discloses Matrix Assisted Laser Desorption Ionisation (MALDI) Time of Flight (TOF) mass spectrometry as a specific method of analysing mass labels by mass spectrometry.

PCT/US97/22639 discloses releasable non-volatile mass-label molecules. In preferred embodiments these labels comprise polymers, typically biopolymers which are cleavably attached to a reactive group or ligand, i.e. a probe. Preferred cleavable linkers appear to be chemically or enzymatically cleavable. This application discloses MALDI TOF mass spectrometry as a specific method of analysing mass labels by mass spectrometry.

PCT/US97/01070, PCT/US97/01046, and PCT/US97/01304 disclose ligands, and specifically nucleic acids, cleavably linked to mass tag molecules. Preferred cleavable linkers appear to be chemically or photo-cleavable. These applications disclose a variety of ionisation methods and analysis by quadrupole mass analysers, TOF analysers and magnetic sector instruments as specific methods of analysing mass labels by mass spectrometry.

None or these prior art applications mention the use of tandem or serial mass analysis of tagged biomolecules.

Gygi et al. (Nature Biotechnology 17: 994-999, "Quantitative analysis of complex protein mixtures using isotope-coded affinity tags" 1999) disclose the use of 'isotope encoded affinity tags' for the capture of peptides from proteins, to allow protein expression analysis. In this article, the authors describe the use of a biotin linker, which is reactive to thiols, for the capture peptides with cysteine in them. A sample of protein from one source is reacted with the biotin linker and cleaved with an endopeptidase. The biotinylated cysteine-containing peptides can then be isolated on avidinated beads for subsequent analysis by mass spectrometry. Two samples can be compared quantitatively by labelling one sample with the biotin linker and labelling the second sample with a deuterated form of the biotin linker. Each peptide in the samples is then represented as a pair of peaks in the mass spectrum. Integration of the peaks in the mass spectrum corresponding to each tag indicate the relative expression levels of the peptide linked to the tags.

Selected reaction monitoring (SRM) and multiple reaction monitoring (MRM) provide highly selective methods of tandem mass spectrometry which have the potential to effectively filter out all molecules and contaminants except the desired analyte. This is particularly beneficial if complex samples are analysed which tend to have several isobaric species present within a defined analytical window. Usually, a combination of precursor (parent ion) selection in the first stage of the mass spectrometer (here termed Q1: quadrupole 1, but also equivalent for the respective stages in non-quadrupole mass spectrometers such as ion traps etc.), fragmentation of the parent ion into many fragments of which one or several specific fragments are selected in the following steps of the MS-measurement (usually in quadrupole 3, Q3) and detected at the ion detector. This two-step selection ensures that the desired analyte is measured and any other ion species are reduced in their intensity. Signal-to-noise ratio is much superior to conventional MS/MS experiments which select one mass window in Q1, and then measure all generated fragments in the ion detector. In principle, this MS-based approach can provide absolute structural specificity for the analyte, and in combination with appropriate stable isotope-labelled internal standards (SISs), it can provide absolute quantitation of analyte concentration.

In conventional SRM/MRM type experiments, a stable isotope labelled reference is used to generate an analyte/reference pair which will be used for quantification of analyte against the reference. For the analysis of proteins, such a reference peptide differs from the analyte to be measured only by incorporation of isotopes, to make it distinctly different in mass for the Q1 selection, but otherwise identical in chemical composition, and physico-chemical behaviour. In a typical experiment, the analyte/reference pair are selected, i.e. in Q1 by switching mass selection channels between these two masses. The subsequent fragmentation of these two ions leads to distinct (specific) fragment masses. One or more suitable fragment masses are then chosen where the Q3 filter remains on the position of the selected fragment ions, thus assuring transition of this ion to the mass analyser, and filtering out other ion species.

Recent work in designing improved mass labels for identifying analytes using mass spectrometry has focused on mass labels which are more easily identified in the mass spectrum without other contaminants.

WO 01/68664 discloses a set of two or more mass labels, each label in the set comprising a mass marker moiety attached via a cleavable linker to a mass normalisation moiety, the mass marker moiety being fragmentation resistant. The aggregate mass of each label in the set may be the same or different and the mass of the mass marker moiety of each label in the set may be the same or different. In any group of labels within the set having a mass marker moiety of a common mass each label has an aggregate mass different from all other labels in that group, and in any group of labels within the set having a common aggregate mass each label has a mass marker moiety having a mass different from that of all other mass marker groups in that group, such that all of the mass labels in the set are distinguishable from each other by mass spectrometry. This application further discloses methods of analysis comprising detecting an analyte by identifying by mass spectrometry a mass label or a combination of mass labels unique to the analyte. Tandem mass spectrometry may be used. Specifically, the mass spectrometer employed to detect the mass label may be a triple quadrupole mass analyser comprising a first analyser to select ions of a particular mass or mass range, a second mass analyser to dissociate the selected ions and a third mass analyser to detect resulting ions.

WO 03/025576 discloses a set of two or more mass labels, each label in the set comprising a mass marker moiety attached via at least one amide bond to a mass normalisation moiety. The mass marker moiety comprises an amino acid and the mass normalisation moiety comprises an amino acid. As for WO 01/68664 the aggregate mass of each label in the set may be the same or different and the mass of the mass marker moiety of each label in the set may be the same or different such that all of the mass labels in the set are distinguishable from each other by mass spectrometry. As for WO 01/68664 this application also discloses a method of analysis which may involve tandem mass spectrometry. This application is specifically directed to the analysis of peptides and mass labels with mass normalisation moieties and mass marker moieties comprising at least one amino acid.

WO 2007/012849 discloses a mass label and a reactive mass label having a general chemical formula for labelling and detecting a biological molecule by mass spectroscopy. The mass labels and reactive mass labels of this invention are clearly identified in a mass spectrum and are easily reacted with analytes. As for WO 01/68664 this application also discloses a method of analysis which may involve tandem mass spectrometry.

The development of isobaric mass tags in the late 1990's has revolutionised biomarker discovery. The ability to analyse multiple samples in theoretically unlimited numbers in a single LC-MS/MS workflow increases throughput whilst at the same time reducing analytical variability. Therefore, there remains a need for improved methods of quantitatively detecting and routinely measuring analytes by mass spectrometry in a wide range of samples.

SUMMARY OF THE INVENTION

Whilst the mass labels provided by WO 01/68664, WO 03/025576 and WO 2007/012849 have allowed significant improved methods of analysis of analytes by mass spectroscopy, there is still a requirement to provide improved methods of detecting an analyte by identifying by mass spectrometry such mass labels. In particular, whilst these new mass labels and methods of analysis allow multiple samples to be analysed simultaneously and quantitatively without significantly increasing the complexity of the mass spectrum, the analysis of isobaric mass labels using known tandem mass spectrometry can still provide inaccurate results for complex samples. There is still a requirement to provide improved methods of analysis which allow easy identification of the mass labels in a mass spectrometer and allow sensitive quantification.

Accordingly, it is an aim of the present invention to solve the problems of the prior art in this field and provide improved methods of assaying a target analyte by mass spectroscopy.

In a first aspect the invention provides a method for assaying for a target analyte, which method comprises:
  (a) providing a plurality of samples which may comprise the target analyte, wherein each sample is differentially labelled with a mass label or a combination of mass labels, wherein the mass labels are from a set of mass labels, wherein each mass label is an isobaric mass label comprising a mass spectrometrically distinct mass marker group, such that the samples can be distinguished by mass spectrometry;
  (b) mixing the plurality of labelled samples to produce an analysis mixture and introducing the analysis mixture into a mass spectrometer;
  (c) selecting ions having a first mass to charge ratio equivalent to an ion of the target analyte labelled with a specific number of mass labels;
  (d) fragmenting ions of the first mass to charge ratio into a plurality of fragment ions, wherein a proportion of the plurality of fragment ions comprise at least one intact mass label;
  (e) selecting ions of a second mass to charge ratio equivalent to an ion of a fragment of the target analyte comprising at least one intact mass label;
  (f) fragmenting ions of the second mass to charge ratio into a plurality of further fragment ions, wherein a proportion of the further fragment ions are ions of the mass marker groups;
  (g) producing a mass spectrum of the further fragment ions produced in step (f); and
  (h) determining from the mass spectrum the quantity of the target analyte in each sample.

The method according to the present invention overcomes the limitations of the art by quantifying molecules of interest using isobarically tagged samples wherein the method comprises two steps of selecting ions of a pre-determined mass to charge ratio each followed by a fragmentation step. The use of such a method provides a high degree of selectivity and, therefore, the mass spectrum produced in the final step provides more accurate quantitative results compared to the results from a conventional tandem mass spectrometry (MS/MS) experiment.

In conventional tandem mass spectrometry (MS/MS) using isobaric mass labels, ions equivalent to the mass of the labelled target analyte are first selected. After selection, the ions of the labelled analytes are subjected to fragmentation and then peaks corresponding to the mass marker group of mass labels are identified. However, the spectra obtained often do not provide accurate quantification of analytes due to co-eluting fragments from contaminants having the same mass to charge ratio as the selected mass to charge ratio. This problem occurs when conducting analysis of complex mixtures of proteins. In complex mixtures, different peptides or peptide fragments may have the same mass as the target analyte. These contaminating peptides will not be differentiated from the target analyte by MS/MS because they will all be selected together as the parent ion mass to charge ratio in the selection step. Therefore, the fragmentation of the parent ions to release mass marker groups from the mass labels will provide a spectrum of mass marker groups from all peptides selected including contaminating peptides having the same mass as the target analyte.

This limitation of MS/MS is overcome in the present invention due to the further steps of selecting (step e) and fragmenting (step f). In step e) selection of the mass to charge ratio equivalent to a desired ion of a fragment of the target analyte comprising at least one intact mass label ensures that the vast majority, if not all contaminating molecules selected in Q1 (step c) are removed from the mass spectrum. Contaminating peptides which fragment in step d) into a plurality of fragments, none of which have a mass to charge ratio equivalent to the second mass to charge ratio selected in step e) will be removed. Therefore, the mass marker groups release from the fragmentation step f) are only from the target analyte and the resulting mass spectrum will provide highly improved accurate quantification results for the target analyte. The method according to the present invention is particularly advantageous for analysis of complex samples because the further degree of selectivity improves specificity.

The method according to the present invention succeeds to generate a combination between the high sensitivity and selectivity of SRM (selected reaction monitoring: one analyte) or MRM (multiple reaction monitoring: multiple analytes) with multiplexing in the final analysis step which is used for quantification purposes.

The quantity determined in step (h) may be the relative quantity of the target analyte in each sample or the absolute quantity of the target analyte in each sample.

A further advantage of the present invention is that it allows a plurality of samples to be analysed together. The plurality of samples may be test samples which may comprise the target analyte.

The term "test sample" refers to any specimen in which an analyte may be present. The test sample may comprise only one analyte. Alternatively, the test sample may comprise a plurality of different analytes.

In one embodiment of the present invention one sample is a test sample and one sample is a calibration sample, wherein the calibration sample comprises one or more different aliquots of the target analytes, each aliquot having a known quantity of the analyte, wherein the test sample and each aliquot of the calibration sample are differentially labelled.

When one or more calibration samples are present, step h) in the method according to the present invention preferably comprises calibrating the quantity of the analyte in the test sample against the known and determined quantities of the analytes in the one or more aliquots in the calibration sample. In a preferred embodiment, the method comprises a step of plotting a graph of the quantity of the analyte in each aliquot versus the quantity of the analyte in each aliquot as determined by mass spectrometry. This step may instead simply involve calculation and mathematical programs or algorithms for performing such calculations that are well understood by the skilled person. The quantity of the analyte in the sample is then calculated by measuring the quantity in the sample as determined by mass spectrometry against the calibration graph. In the context of this invention, a reference to "a quantity as measured by mass spectrometry" is typically an ion abundance, ion intensity, or other signal measured by mass spectrometry which relates to the quantity of an analyte. This embodiment provides more accurate quantification results which are independent of externally obtained calibrations, thus providing for a much more robust and reliable analysis.

The different aliquots each have a different known quantity of the analyte. The term "known quantity" means that the absolute quantity, or a qualitative quantity of the analyte in each aliquot of the calibration sample is known.

An absolute quantity means a quantity which is a known. This allows for the absolute quantity of an analyte in a test sample to be determined.

A qualitative quantity in the present context means a quantity which is not known absolutely, but may be a range of quantities that are expected in a subject having a particular state, for example a subject in a healthy or diseased state, or some other expected range depending on the type of test sample under investigation. Each aliquot is "different" since it contains a different quantity of the analyte. Typically this is achieved by taking different volumes from a standard sample, especially for qualitative quantities where taking different volumes will ensure that different quantities are present in each aliquot in a desired ratio, without needing to know the absolute quantities. As an alternative, each aliquot is prepared separately and is not taken from the same sample. In one embodiment, each different aliquot has the same volume, but comprises a different quantity of the analyte.

Preferably, the or each calibration sample comprises two or more different aliquots of the target analyte. The use of two or more different aliquots of the target analyte allows the construction of multi-point standard curves for each analyte without increasing MS complexity. Analyte quantitation is obtained in the mass spectrum produced in step g), and the analyte in the sample and in the calibration sample can be simultaneously quantified and identified. Alternatively, only the quantity of the analyte is determined. This method provides means for the measurement of up to 10, up to 20, up to 50 or more analytes in a single experiment.

The method according to the present invention may comprise analysis of a plurality of test samples in addition to one or more calibration samples. In this embodiment, each of the plurality of test samples is preferably assayed for the same analyte. Preferably the same calibration sample is used for each test sample to be assayed. Typically, the same known volume of the calibration sample comprising at one or more aliquots of the analyte is added to each different test sample. This method is particularly useful in clinical studies involving multiple samples from patients. If a large quantity of the calibration sample is prepared and fractions taken, the same calibration sample can be used by multiple laboratories, facilitating cross-study and cross-laboratory comparisons. Each test sample may be differentially labelled with one or more of the isobaric mass labels and combined with one or more calibration samples in step b), and the quantity of the analyte in each sample is determined simultaneously in step h). Alternatively, each test sample may be labelled with the same mass label and steps b) to h) are repeated for each different test sample.

In one embodiment the method according to the present invention may be used to assay a plurality of different target analytes. In this embodiment the method comprises a step of repeating steps (c) to (h) for each target analyte. In this embodiment, wherein one sample is a test sample, a calibration sample may be provided for each different analyte. Each calibration sample comprises one or more different aliquots of a target analyte, wherein the test sample and each aliquot of each calibration sample are differentially labelled. In one embodiment the plurality of analytes are peptide fragments of a protein or polypeptide which are produced by chemical or enzymatic processing of the protein or polypeptide prior to step (a). In a particular embodiment, the plurality of analytes are peptides from the same protein or polypeptide.

BRIEF DESCRIPTION OF THE DRAWINGS

The present invention will now be described in more detail with reference to the following figures:

FIG. 1b shows a zoomed in section of the spectrum of FIG. 1a showing the peaks of the mass marker groups.

FIG. 2b shows a zoomed in section of the spectrum of FIG. 2a showing the peaks of the mass maker groups.

FIG. 3 shows a MS spectrum of peptide VAFSLR (SEQ ID NO: 2) labelled with different isobaric mass labels from a set of six mass labels, each label representing a predetermined relative amount of the peptide (the ratio of the mass marker groups having masses 126:127:128:129:130:131 is 1:3:5:5:3:1).

FIG. 4 shows a MS/MS spectrum of the labelled VAFSLR peptide (SEQ ID NO: 2), as analysed in FIG. 3.

FIG. 5a shows a MS/MS spectrum of the distinct mass marker groups from the labelled VAFSLR peptide (SEQ ID NO: 2), as analysed in FIG. 3; FIG. 5b shows a MS/MS/MS spectrum of the distinct mass marker groups from the labelled VAFSLR peptide (SEQ ID NO: 2), as analysed in FIG. 3.

FIG. 7 shows a MS/MS spectrum of the labelled AVFSLR peptide (SEQ ID NO: 3), as analysed in FIG. 6.

FIG. 8a shows a MS/MS spectrum of the distinct mass marker groups from the labelled AVFSLR peptide (SEQ ID NO: 3), as analysed in FIG. 6; FIG. 8b MS/MS/MS spectrum of the distinct mass marker groups from the labelled AVFSLR peptide (SEQ ID NO: 3), as analysed in FIG. 6.

FIG. 9 shows a MS spectrum of peptide FAVSLR (SEQ ID NO: 4) labelled with different isobaric mass labels from a set of six mass labels, each label representing a predetermined relative amount of the peptide (the ratio of the mass marker groups having masses of 126:127:128:129:130:131 is 4:4:4:1:1:1).

FIG. 11a shows a MS/MS spectrum of the distinct mass marker groups from the labelled FAVSLR peptide (SEQ ID NO: 4), as analysed in FIG. 9; FIG. 11b MS/MS/MS spectrum of the distinct mass marker groups from the labelled FAVSLR peptide (SEQ ID NO: 4), as analysed in FIG. 9.

FIG. 12 shows a MS spectrum of peptide LAFSVR (SEQ ID NO: 5) labelled with different isobaric mass labels from a set of six mass labels, each label representing a predetermined relative amount of the peptide (the ratio the mass marker groups having masses of 126:127:128:129:130:131 is 5:3:1:1:3:5).

FIG. 14a shows a MS/MS spectrum of the distinct mass marker groups from the labelled LAFSVR peptide (SEQ ID NO: 5), as analysed in FIG. 12; FIG. 14b MS/MS/MS spectrum of the distinct mass marker groups from the labelled LAFSVR peptide (SEQ ID NO: 5), as analysed in FIG. 12.

FIG. 15 shows a MS spectrum of a mixture of peptide VAFSLR (SEQ ID NO: 21 and LAFSVR (SEQ ID NO: 5) each labelled with different isobaric mass labels from a set of six mass labels, each label representing a predetermined relative amount of a peptide (peptide VAFSLR (SEQ ID NO: 2): the ratio of mass marker groups having masses of 126:127:128:129:130:131 is 1:3:5:5:3:1; and peptide LAFSVR (sEQ ID NO: 5): the ratio of mass marker groups having masses of 126:127:128:129:130:131 is 5:3:1:1:3:5).

FIG. 16 shows a MS/MS spectrum of a mixture of labelled VAFSLR (SEQ ID NO: 2) and LAFSVR peptides (SEQ ID NO: 5), as analysed in FIG. 15.

FIG. 17 shows a MS/MS spectrum of the distinct mass marker groups from a mixture of labelled VAFSLR (SEQ ID NO: 2) and LAFSVR peptides (SEQ ID NO: 5), as analysed in FIG. 15.

FIG. 18b shows a MS/MS/MS spectrum of the distinct mass marker groups from the b1-ions of labelled LAFSVR (SEQ ID NO: 5), as analysed in FIG. 15.

FIG. 19 shows a MS spectrum of a mixture of peptide AVFSLR (SEQ ID NO: 3) and FAVSLR (SEQ ID NO: 4) each labelled with different isobaric mass labels from a set of six mass labels, each label representing a predetermined relative amount of a peptide (peptide AVFSLR (SEQ ID NO: 3): the ratio of the mass marker groups having masses of 126:127:128:129:130:131 is 1:1:1:4:4:4; peptide FAVSLR (SEQ ID NO: 4): the ratio of the mass marker groups having masses of 126:127:128:129:130:131 is 4:4:4:1:1:1).

FIG. 20 shows a MS/MS spectrum of a mixture of labelled AVFSLR (SEQ ID NO: 3) and FAVSLR peptides (SEQ ID NO: 4), as analysed in FIG. 19.

FIG. 21 shows a MS/MS spectrum of the distinct mass marker groups from a mixture of labelled AVFSLR (SEQ ID NO: 3) and FAVSLR peptides (SEQ ID NO: 4), as analysed in FIG. 19.

FIG. 22a shows a MS/MS/MS spectrum of the distinct mass marker groups from the b1-ions of labelled AVFSLR (SEQ ID NO: 3), as analysed in FIG. 19; and FIG. 22b shows a MS/MS/MS spectrum of the distinct mass marker groups from the b1-ions of labelled FAVSLR (SEQ ID NO: 4), as analysed in FIG. 19.

FIGS. 27a and b disclose SEQ ID NO: 20.

FIGS. 28a and b disclose SEQ ID NO: 21.

DETAILED DESCRIPTION OF THE INVENTION

Figure 1A:
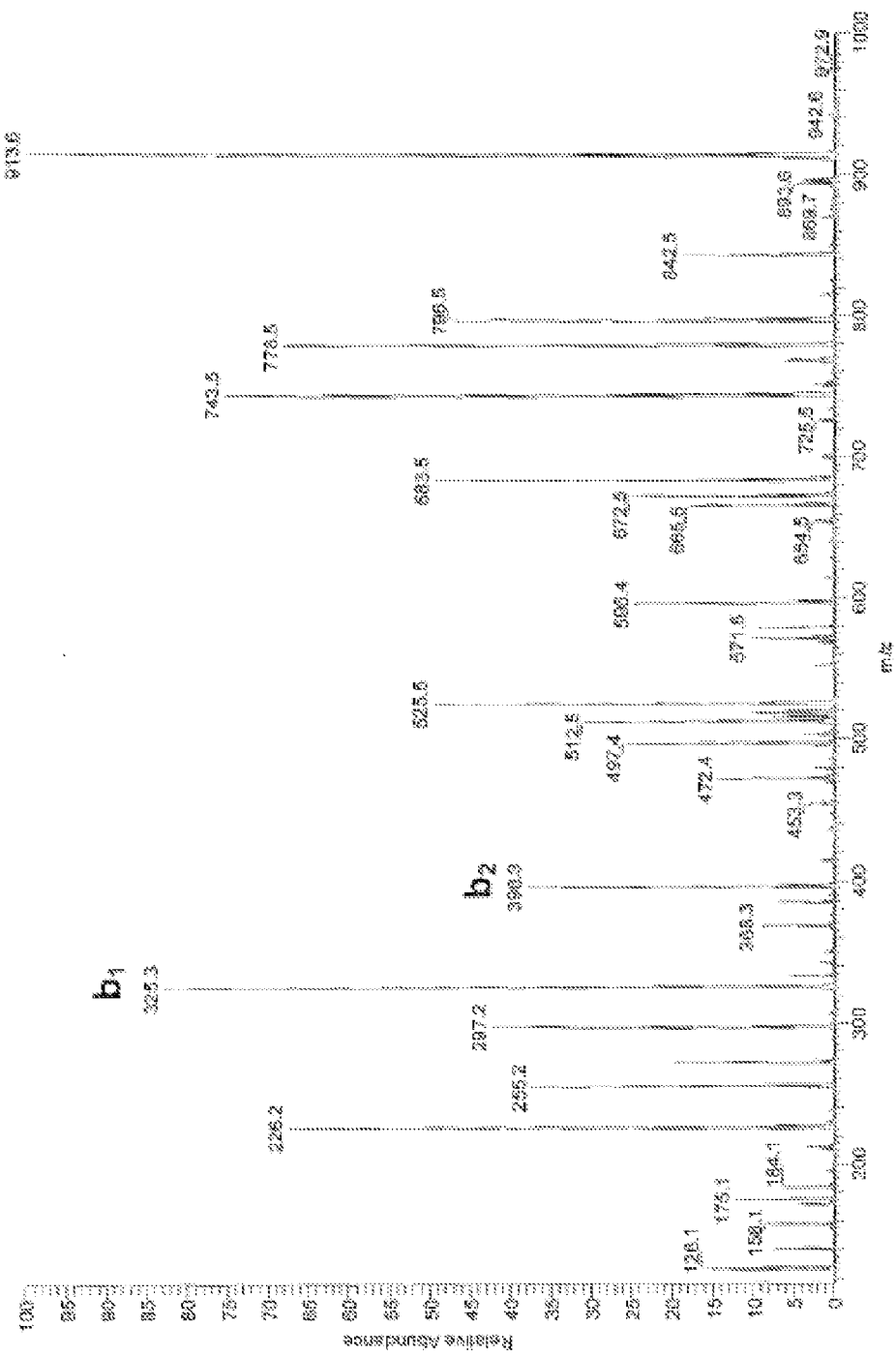
FIG. 1a shows a MS/MS spectrum of peptide VATVSLPR (SEQ ID NO: 1) labelled with different isobaric mass labels from a set of two mass labels, each label representing a predetermined relative amount of the peptide (the ratio of the mass marker groups having masses 126:127 is 2:1)

The term "analyte" is not particularly limiting, and the methods according to the present invention may be employed to assay any type of molecule provided that it can be analysed by mass spectrometry, and is capable of being labelled by an isobaric mass label with a mass spectrometrically distinct mass marker group. Analytes include amino acids, peptides, polypeptides, proteins, glycoproteins, lipoproteins, nucleic acids, polynucleotides, oligonucleotides, DNA, RNA, peptide-nucleic acids, sugars, starches and complex carbohydrates, fats and complex lipids, polymers and small organic molecules such as drugs and drug-like molecules or fragments thereof. Preferably the analyte is a peptide, protein, nucleotide or nucleic acid.

In relation to this invention the term analyte shall be synonymous with the term biomolecule.

In relation to this invention the term "protein" shall encompass any molecule comprising two or more amino acids including di-peptides, tri-peptides, peptides, polypeptides and proteins.

In relation to this invention the term "nucleic acid" shall encompass any molecule comprising two or more nucleotide bases including di-nucleotides, tri-nucleotides, oligonucleotides, deoxyribonucleic acids, ribonucleic acids and peptide nucleic acids.

The wording "set of sixplex Tandem Mass Tags (TMT)" refers to a set of six isobaric mass labels, wherein each label comprises a mass spectrometrically distinct mass marker group. An example of a set of sixplex Tandem Mass Tags are $TMT^6$-128, $TMT^6$-129, $TMT^6$-130, $TMT^6$-131, wherein "6" represents the number of labels in the set and the numbers 128-131 following "TMT", represent the mass of the mass marker group. In the same manner, a set of duplex Tandem Mass Tags refers to a set of two isobaric mass labels. An examples of a set of duplex Tandem Mass Tags are $TMT^2$-126 and $TMT^2$-127, wherein "2" represents the number of labels in the set and the numbers 126 and 127 following "TMT", represent the mass of the mass marker group. A set of fiveplex Tandem Mass Tags refers to a set of 5 isobaric mass labels.

The term 'MS' in the context of the present invention refers to a method of mass spectrometry comprising producing ions from a sample and producing a mass spectrum of the ions.

The term 'MS/MS' in the context of the present invention refers to the method according to the present invention comprising selecting ions of particular mass to charge ratio, subjecting selected ions to fragmentation, for example by Collision Induced Dissociation (CID), and producing a mass spectrum of the fragment ions.

The term 'MS/MS/MS' in the context of the present invention refers to the method according to the present invention comprising steps (a) to (h).

In relation to this invention the term "mass spectrometry" shall include any type of mass spectrometry capable of fragmentation analysis. The mass spectrometers suitable for use in the present invention include instruments that comprise any form of analyser capable of MS/MS/MS.

In one embodiment, steps (c) to (g) of the method according to the present invention are carried out in separate quadrupoles in a mass spectrometer. In this embodiment, step c) of selecting the ions having a first mass to charge ratio is performed in the first mass analyser of a serial instrument (Q1). The selected ions are then channelled into a separate collision cell (Q2) where they are collided with a gas or a solid surface to produce a plurality of fragment ions in step d). The collision products from step d) are then channelled into a third mass analyser (Q3) wherein ions of a second mass to charge ratio (MS/MS ions) are selected in step e). The selected ions from step e) are then channelled into a separate collision cell (Q4) wherein they are collided with a gas or a solid surface to produce a plurality of further fragment ions in step f). The further fragment ions from step f) are channelled into a further mass analyser (Q5) of a serial instrument in step g) to detect collision products. Typical serial instruments include five quadrupole mass spectrometers, tandem sector instruments and quadrupole time of flight (TOF) mass spectrometers.

Alternatively, steps (c) to (g) of the method according to the present invention are carried out sequentially in the same zone of a mass spectrometer. This may be effected in ion trap mass analysers and Fourier Transform Ion Cyclotron Resonance (FT-ICR) mass spectrometers, for example.

MS/MS/MS experiments according to the present invention can be undertaken using conventional 3D iontraps, hybrid geometry instruments such as a quadrupole ion trap in combination with a TOF analyser, as well as the larger footprint four sector instruments.

Wu Z., Bordas-Nagy J. and Fenselau C. (1991) "Triple mass spectrometry (MS/MS/MS) with a floated collision cell in a four-sector tandem mass spectrometer" *Organic Mass Spectrometry* 26, 10, 908-911 describes a method for carrying out MS/MS/MS experiments with an electrically floated collision cell in the third field-free region on a tandem double-focusing mass spectrometer. The experiments were performed using a JEOL JMS-HX110/HX110 four-sector mass spectrometer and although the method involved calibration of the magnet calibration at all accelerating voltages, it is generally applicable at any value of the collision cell voltage.

Figure 33:
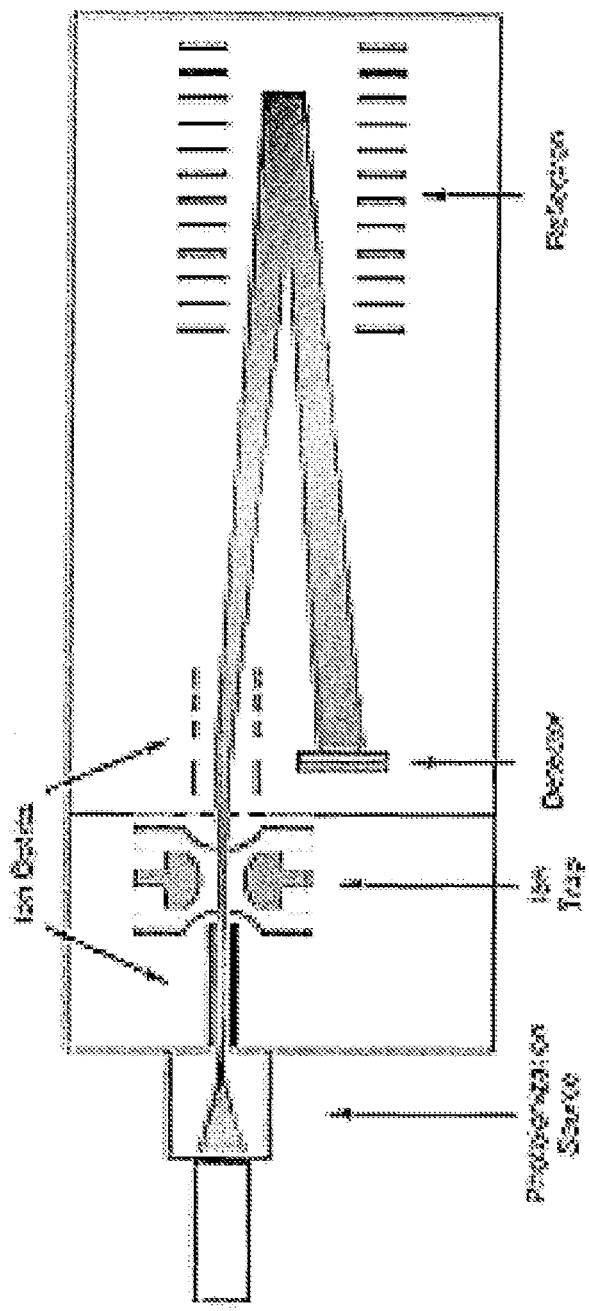
FIG. 33 shows a schematic of the QitTof™ instrument.
Figure 34:
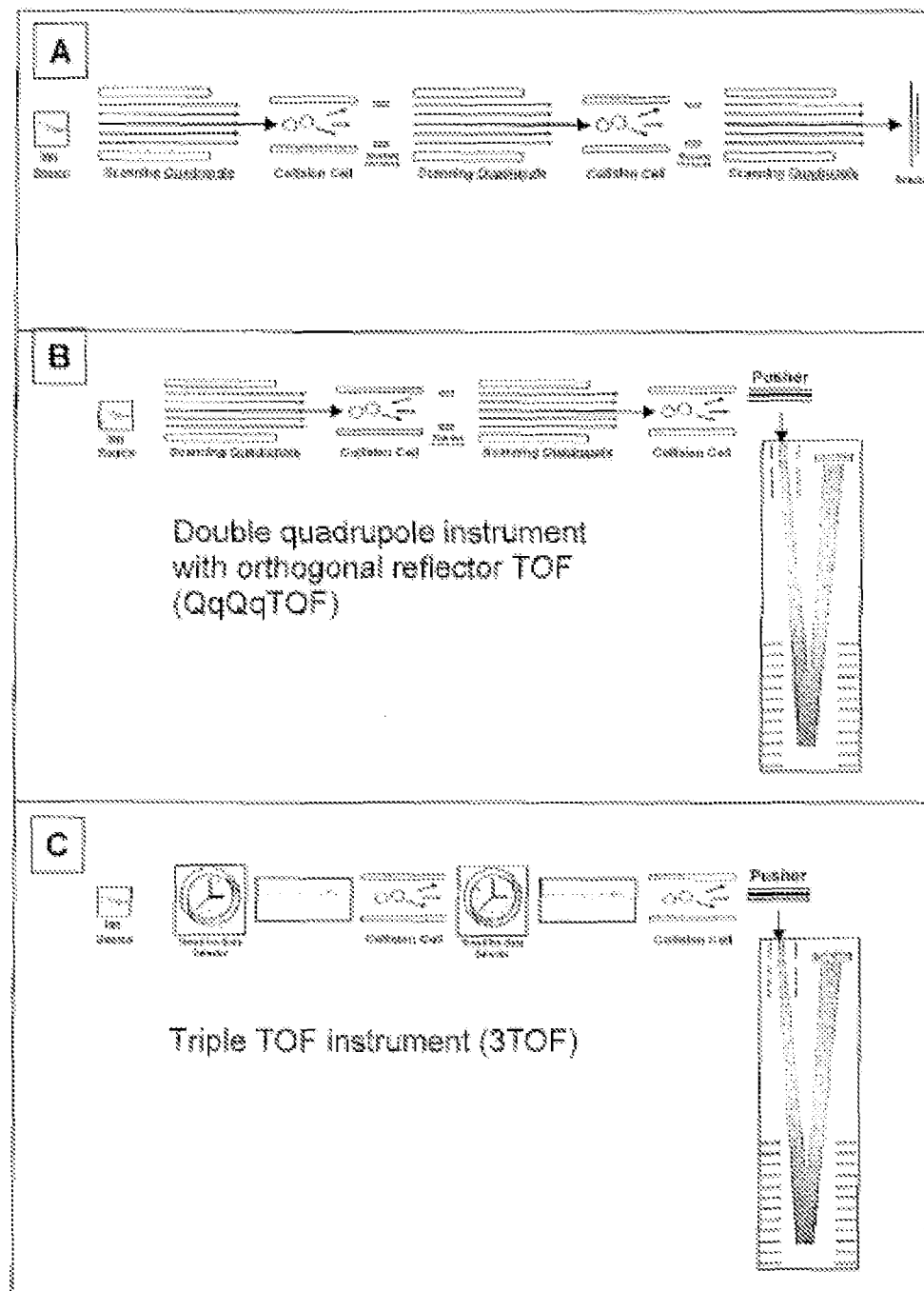
FIGS. 34a, 34b and 34c shows alternative arrangements of mass spectrometers capable of MS/MS/MS.

Quadrupole ion traps (QITs) are an effective means to accumulate and store ions. The combination of QIT with TOF mass spectrometry offers powerful capabilities not available by QIT or TOF mass spectrometry alone. Syagen® has already combined these devices into a single instrument called the QitTof™, which is the first commercially-available instrument to offer the MS advantages of QIT MS with the high-speed data collection rates of TOF MS. The configuration of the QitTof™ instrument is shown in FIG. 33. Shimadzu have also subsequently developed an LCMS-QIT-TOF system. FIG. 34 shows a schematic to illustrate the geometry of the QitTof™ instrument.

There are specific benefits of the QitTof™ geometry compared to other instruments. The QitTof™ configuration has the potential for higher ion transmission efficiency and allows effective MS$^n$ operation compared to orthogonal-extraction TOF MS. The QIT gives the advantage of mass-selective ejection with higher dynamic range and greater ion trap capacity due to the higher repetition rate because ions are pulsed out rather than scanned out of the QIT. The TOF provides the advantage of multichannel mass detection leading to efficient collection of all ions. Better ion mass accuracy is also achieved using the TOF analyzer.

Several other instrument geometries could be considered for MS$^3$ experiments in the present invention and a selection of future possibilities are shown in FIG. 34. The performance of each design is difficult to assess at this stage and will require further investigation. FIG. 34 A depicts a penta-quadrupole arrangement with three scanning quadrupoles and two collision cells. An ion multiplier detector is typically used in conjunction with quadrupole mass analysers. FIG. 34 B depicts a double scanning quadrupole with an orthogonal reflectron TOF as the final stage analyser. FIG. 34 C depicts a triple stage TOF instrument with timed ion gates permitting ions with a user-specified mass range to enter the first two linear TOF analysers.

In the present invention, matrix assisted laser desorption/ionisation (MALDI) techniques may be employed. MALDI requires that the biomolecule solution be embedded in a large molar excess of a photo-excitable 'matrix'. The application of laser light of the appropriate frequency results in the excitation of the matrix which in turn leads to rapid evaporation of the matrix along with its entrapped biomolecule. Proton transfer from the acidic matrix to the biomolecule gives rise to protonated forms of the biomolecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. The laser energy and the timing of the application of the potential difference used to accelerate the ions from the source can be used to control fragmentation with this technique. This technique is highly favoured due to its large mass range, due to the prevalence of singly charged ions in its spectra and due to the ability to analyse multiple peptides simultaneously. The TOF/TOF technique may be employed in the present invention.

The photo-excitable matrix comprises a 'dye', i.e. a compound that strongly absorbs light of a particular frequency, and which preferably does not radiate that energy by fluorescence or phosphorescence but rather dissipates the energy thermally, i.e. through vibrational modes. It is the vibration of the matrix caused by laser excitation that results in rapid sublimation of the dye, which simultaneously takes the embedded analyte into the gas phase.

Although MALDI techniques are useful in the context of the present invention, the invention is not limited to this type of technique, and other techniques common to the art can be employed by the skilled person in the present invention, if desired. For example electrospray or nanoelectrospray mass spectrometry may be employed.

The method according to the present invention may comprise a further step prior to step (a) of differentially labelling each sample and, when one or more calibration samples are present; each aliquot of the calibration sample with one or more isobaric mass labels. In the embodiments wherein one or more calibration samples are present the method also preferably comprises a further step of combining the differentially labelled aliquots to produce a calibration sample prior to step (a).

The target analyte may be attached to one mass label, two mass labels or more than two mass labels. Preferably the target analyte or fragment thereof is attached to two isobaric mass labels. It is also preferable that at least one mass label is attached to each end of the target analyte. This is particularly preferred when the target analyte is a protein or nucleic acid.

The samples may be labelled under suitable conditions to control how many labels attach to the target analyte. For example, an excess quantity of label may be added to the samples to ensure the maximum number of labels attach to each analyte. This may be preferable when it is advantageous to attach a mass label to each end of a nucleic acid or protein analyte. Alternatively, the reactive group of the mass label and/or the conditions for labelling may be controlled to attach a mass label to a preferred end of the analyte, such as the C-terminal or N-terminal end of a protein.

If the target analyte is a protein or peptide the N-terminal and C-terminal of each target analyte is preferably labelled with a mass label. Preferably, the amino-terminal amine group and C-terminal epsilon-amine group of lysine of each analyte each comprises a mass label. The peptide shown in FIG. 25a and FIG. 26b (LVNEVTEFAK (SEQ ID NO: 8)) is attached to two labels wherein one label is attached to the N-terminal leucine and one label is attached to the C-terminal lysine.

In step c) in the method according to the present invention, ions having a first mass to charge ratio equivalent to an ion of the target analyte labelled with a specific number of mass labels are selected. The labelled target analytes in each sample are selected in step c) because they have identical masses.

In one embodiment the first mass to charge ratio is equivalent to the mass to charge ratio of the unfragmented parent ion of the target analyte labelled with a specific number of mass labels. Alternatively, the first mass to charge ratio is equivalent to the mass to charge ratio of a fragment ion of the target analyte labelled with a specific number of mass labels.

The specific mass to charge ratio selected for step c) depends upon the target analyte and the number of labels attached to the target analyte. The skilled person would easily be able to select a suitable first mass to charge ratio for step c). It is preferred that the ions selected in step c) have a 2+ or higher charge state.

When the method according to the present invention is carried out for example on a sample comprising a mixture of components, such as proteins, a number of proteins or protein fragments may have the same mass and, therefore, a number of different ions having the same mass may be selected in step c).

Following step c) the selected ions having a first mass to charge ratio are fragmented in step d) into a plurality of fragment ions, wherein a proportion of the plurality of fragment ions comprise at least one intact mass label.

A proportion of the plurality of fragment ions comprising at least one intact mass label means that greater than 0% of the fragment ions comprise at least one intact mass label. The proportion of these fragments provided in step d) is sufficient to allow the mass reporter groups to be detected in the mass spectrum produced in step g).

The present inventors have discovered that analytes labelled with isobaric mass labels fragment in step d) to produce fragment ions which comprise at least one intact mass label. This is an important finding in the present invention because it allows a further selection step to remove contaminants before cleavage of the mass reporter group from the labelled target analyte. This provides accurate quantification results. The inventors have found that it is advantageous for the target analyte to be attached to two or more mass labels to ensure that at least one mass label is intact after step d).

When the target analyte is a peptide, the peptides predominantly fragment into y- and b-ion series, with other forms also seen including a-series, c-series, x-series and z-series. The fragmentation conditions may be selected in step d) in order to control the type of fragment ions produced. Preferably, the fragmentation conditions are selected to ensure b- and y-ions are the most prominent fragment ions. Preferably the collision energy should be chosen quite low to prevent consecutive fragmentation. For example, an Ion trap may be used to ensure that consecutive fragmentation does not occur.

Typically, the fragmentation is caused by Collision Induced (CID), Surface Induced Dissociation (SID), Electron Capture Dissociation (ECD), Electron Transfer Dissociation (ETD), or Fast Atom Bombardment.

Electron capture dissociation (ECD) is a method of fragmenting multiply charged (protonated) peptide or proteins ions for tandem mass spectrometric analysis (structural elucidation). In this method multiply protonated peptide or proteins are confined in the Penning trap of a Fourier transform ion cyclotron resonance (FT-ICR) mass spectrometer and exposed to electrons with near-thermal energies. The capture of a thermal electron by a protonated peptide is exothermic ($\approx 6$ eV; 1 eV=$1.602 \times 10^{-19}$ J), and causes the peptide backbone to fragment by a nonergodic process (i.e., a process that does not involve intramolecular vibrational energy redistribution).

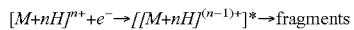

In addition, one or more protein cations can be neutralised with low energy electrons to cause specific cleavage of bonds to form c, z products, in contrast to b, y products formed by other techniques such as collisionally activated dissociation (CAD; also known as collision-induced dissociation, CID). Since thermal electrons introduced into the RF fields of RF 3D quadrupole ion trap (QIT), quadrupole time-of-flight (TOF), or RF linear 2D quadrupole ion trap (QLT) instruments maintain their thermal energy only for a fraction of a microsecond and are not trapped in these devices, ECD remains a technique exclusively used with FTICR, the most expensive type of MS instrumentation.

Electron transfer dissociation (ETD) is a method of fragmenting multiply protonated peptide or proteins ions for tandem mass spectrometric analysis (structural elucidation). Similar to electron capture dissociation (ECD), ETD induces fragmentation of cations (e.g. multiple charged peptide or proteins) by transferring electrons to them. In contrast to ECD, ETD does not use free electrons but employs radical anions for this purpose (e.g. anthracene or azobenzene anions which possess sufficiently low electron affinities to act as electron donors).

After the electron transfer, ETD results in a similar fragmentation pattern as ECD, i.e. the formation of so called c and z ions. Based on the different way of electron transfer, ETD can be implemented on various "lower cost" mass spectrometers like quadrupole ion trap (QIT) or RF linear 2D quadrupole ion trap (QLT) instruments which are not appropriate for ECD. For an appropriate reference see John E. P. Syka, Joshua J. Coon, Melanie J. Schroeder, Jeffrey Shabanowitz, and Donald F. Hunt, PNAS, Vol. 101, no. 26, pp. 9528-9533.

Whilst the method of fragmentation is not particularly limited, the most preferred embodiment is where the fragmentation is caused by collision-induced dissociation.

In one embodiment the method according to the present invention comprises a further step after step (d) of producing a mass spectrum of the plurality of fragment ions from step (d). The mass spectrum produced after step d) may be used to identify the target analyte by identifying one or more fragment ions characteristic of the target analyte in the mass spectrum. The fragment ions produced in the spectrum may be used for database searching, particularly for peptide analytes, to determine the identity of the analyte.

The fragmentation in step (d) may cleave a proportion of mass marker groups from the mass labels and peaks representing the mass marker groups may be seen in a mass spectrum if produced. However, if this mass spectrum is used to measure the quantity of target analyte in the samples it will produce inaccurate results due to the presence of labelled contaminants in step (d).

Following fragmentation in step d), ions of a second mass to charge ratio equivalent to an ion of a fragment of the target analyte comprising at least one intact mass label is selected in step e).

As discussed above, when the sample is a complex mixture step c) may select a number of ions including the target analyte and other contaminating ions having the same mass. Accordingly, analysis of the mass marker groups from the mass labels attached to all ions selected in step c) would provide quantitation results which do not accurately represent the quantity of the target analyte. To overcome this limitation step e) provides a further selection step of the target analyte to be passed through for further analysis. The mass to charge ratio equivalent to an ion of a fragment of the target analyte comprising at least one intact mass label ensures that contaminating molecules selected in step c) are removed from the mass spectrum.

Preferably in step (e) the second mass to charge ratio is equivalent to a fragment ion of the target analyte comprising at least one intact mass label which fragment ion is unique to the target analyte.

The second mass to charge ratio selected in step e) may be any suitable fragment ion produced in step d) provided that the fragment ion comprises at least one intact mass label.

The second mass to charge ratio may be equivalent to an a-series ion, a b-series ion, a c-series ion, an x-series ion, a y-series ion or a z-series ion. The type of ion selected in step e) may be chosen depending upon the amount of each ion produced. For example, a peptide may predominantly fragment into b-series ions and the b1 ion may be the most prevalent ion. The most prevalent ion will ensure that a good signal of mass reporter groups is produced in the mass spectrum in step h).

The type of ion selected in step e) may also be chosen depending upon the degree of selectivity required. A larger fragment ion selected in step e) will provide better selectivity for target analyte. For example, selection of a b1 ion will differentiate between peptides having different amino acids at the N-terminus. However, if greater selectivity is required to differentiate between peptides having the same b1 ion, a larger ion such as a b2 or b3 ion may be selected. It may also be preferable to select larger ions if fragmentation in step d) produces different series ions having the same mass.

The best type of ion to select in step e) may be determined separately to the method of the present invention, for example using MS-data results or in silico methods.

In one embodiment according to the present invention, a second mass to charge ratio is selected in step e), such as a b1 ion or y1 ion, and steps f) to h) are carried out on the selected fragment ion. Steps e) to h) may then be repeated and the second mass to charge ratio selected in step e) ensures a larger ion is selected, such as b2 or y2. The results from the larger ion may then be compared to the results from the smaller ion as a check to ensure that the results accurately reflect the quantity of the target analyte in the sample.

Preferably, the second mass to charge ratio is equivalent to a y-series ion comprising an intact mass label. For example, the y-series ion may be a y1 ion, y2 ion, y3 ion etc. provided that the ion comprises at least one intact mass label.

In an alternative preferred embodiment the second mass to charge ratio is equivalent to a b-series ion comprising an intact mass label. For example, the b-series ion may be a b1 ion, b2 ion, b3 ion etc. provided that the ion comprises at least one intact mass label.

Preferably the ion, such as the y-series ion or b-series ion, has a higher mass to charge ratio compared to the first mass to charge ratio selected in step (c). It is also preferably that the ion selected in step e) has a charge state which is one less compared to the charge state of the ion selected in step c) but with a higher mass to charge ratio compared to the charge state of the ion selected in step c). This ensures that the selected ion appears in a very clean part of the mass spectrum without any contaminating ions, which provides an excellent signal to noise ratio.

The number and positioning of the mass labels attached to the target analyte may be controlled depending upon which fragment ion is preferred for selection in step e). For example, when the analyte is a peptide and it is preferable to select a b-series ion labelling can be controlled to ensure that the peptide is attached to a mass label at the N-terminal end. If it is preferable to select a y-series ion labelling can be controlled to ensure that the peptide is attached to a mass label at the C-terminal end.

It may be preferable to select a b-series ion in step e) and repeat the method selecting a y-series ion in step e). In this embodiment, the labelling can be controlled to ensure the peptide is attached to a mass label at the C-terminal end and the N-terminal end. For example, if the target analyte is a peptide and the amino-terminal amine function and the C-terminal epsilon-amine function of lysine are attached to mass labels, y-ions are generated having one intact mass label on the lysine, or b-ions are generated having one intact n-terminal mass label.

The fragmentation step d) may produce pseudo y-ions which represent the full length peptide with the loss of one mass marker group plus, for example, the neighbouring carbonyl group, and appearing at a charge state −1. These ions are not useful for selection in step e) since they will contain contaminants of the same m/z and charge state as the target analyte which also have lost only one mass reporter group and if the analyte is only attached to one mass label then this ion would not produce fragments comprising an intact mass label.

Following selection of ions having the second mass to charge ratio in step e), these ions are then fragmented into a plurality of further fragment ions in step f), wherein a proportion of the further fragment ions are ions of the mass marker group.

Due to the selection in step e), which allows ions of the target analyte to be passed through for further analysis, the mass marker groups released from the fragmentation step f)

are only from the target analyte and the resulting mass spectrum will provide accurate quantification results for the target analyte.

A proportion of the further fragment ions are ions of the mass marker group means that greater than 0% of the fragment ions are ions of the mass marker group. In step g) a mass spectrum of the further fragment ions is produced and, therefore, the proportion of ions of the mass marker group is sufficient to allow determination of the quantity of the target analyte in each sample from the mass spectrum.

The fragmentation in step f) may be carried out by any of the methods as discussed above with respect to step d). The energy used in the fragmentation step f) is preferably higher compared to the energy used in step d) in order to ensure that mass marker groups are cleaved from the rest of the mass label. It is preferably to use a collision cell in step f) not an Ian trap because in this step it is preferably to promote consecutive fragmentation. In one embodiment the method according to the present invention comprises a further step after step (f) of selecting ions of a range of mass to charge ratios equivalent to the range of mass to charge ratios of the mass reporter groups. This third selection step ensures that only the ions of the mass reporter groups are entered into the mass spectrum produced in step g), thereby removing any contaminants.

Following fragmentation in step f), a mass spectrum is produced in step g) of the further fragment ions.

In step h) the quantity of the target analyte in each sample is determined from the mass spectrum produced in step g). This step preferably comprises identifying the fragment ions corresponding to the mass marker groups of the mass labels in the mass spectrum and determining the quantity of the analyte in each sample on the basis of the quantity of their mass marker groups in the mass spectrum. In the embodiment, wherein one or more calibration samples are analysed step h) comprises determining the quantity of the analyte in the test sample on the basis of the quantity of the mass marker groups in the related mass spectrum relative to the quantities of the mass marker groups from the aliquots of the calibration sample in the same mass spectrum. As discussed above, the determined quantity of analyte may be the absolute quantity, or a qualitative quantity of the analyte.

The test sample may be from a natural source or may be produced synthetically. An example of a synthetic sample is a mixture of recombinant proteins. In one embodiment, the test sample is a complex mixture, for example a sample from a plant or an animal. In a preferred embodiment the sample is from a human.

Examples of test samples assayed in the present invention include: mammalian tissue, fluids such as blood, plasma, serum, cerebrospinal fluid, synovial fluid, ocular fluid, urine, tears and tear duct exudate, lung aspirates including bronchoalveolar lavage fluid, saliva, sputum, breast milk, nipple aspirate, semen, lavage fluids, cell extracts, cell lines and sub-cellular organelles, tissues such as solid organ tissues, cell culture supernatants or preparations derived from mammals, fish, birds, insects, annelids, protozoa and bacteria, tissue culture extracts, plant tissues, plant fluids, plant cell culture extracts, bacteria, viruses, fungi, fermentation broths, foodstuffs, pharmaceuticals and any intermediary products.

In a preferred embodiment the test sample is plasma from blood. In a particularly preferred embodiment the test sample is depleted plasma. This is plasma which has been purified to remove the most abundant plasma proteins, such as albumin, so as to reduce the protein load in the sample, hence reducing the number of analytes and the total protein content in the sample.

The calibration sample may be a natural sample such as a body fluid or a tissue extract or may be synthetic, as for the sample to be assayed. The calibration sample may comprise a recombinantly expressed protein, synthetically manufactured peptide or oligonucleotide. In addition it is possible to produce a number of different peptides by recombinant protein expression in a concatenated sequence. European patent application EP 1736480 discloses methods of producing multiple reference peptides as a concatenated recombinant protein for use in multiple reaction monitoring experiments in a manner analogous to the AQUA methodology. Such methods of production may be combined with isobaric mass labels to provide the calibration samples according to any of the various aspects of this invention.

The calibration sample may be a standardised form of the sample to be assayed. The calibration sample may comprise all of the components of the sample to be assayed but in particular quantities. For example, the calibration sample may comprise a standardised preparation of mammalian tissue, fluids such as blood, plasma, serum cerebrospinal fluid, synovial fluid, ocular fluid, urine, tears and tear duct exudate, lung aspirates including bronchoalveolar lavage fluid, saliva, sputum, breast milk, nipple aspirate, semen, lavage fluids, cell extracts, cell lines and sub-cellular organelles, tissues such as solid organ tissues, cell culture supernatants or preparations derived from mammals, fish, birds, insects, annelids, protozoa and bacteria, tissue culture extracts, plant tissues, plant fluids, plant cell culture extracts, bacteria, viruses, fungi, fermentation broths, foodstuffs, pharmaceuticals and any intermediary products. If the analytes of interest are proteins, since all proteins in the calibration sample are labelled, the entire proteome of such a sample may be used as a reference for all proteins of the study sample.

Alternatively, the calibration sample may comprise only analytes to be assayed in the sample, and not any other components of the sample. The calibration sample comprising one or more analytes may be produced and isobarically labelled exogenously and added to the complex mixture containing the analyte. For example, if the sample is a plasma sample, but only a particular protein is to be assayed in the plasma sample, a calibration sample can be prepared which comprises different aliquots of the recombinant form of the protein.

In an alternative method, the absolute quantity of an analyte in each aliquot in the calibration sample is not known. In this embodiment, the quantity of analyte in each aliquot in the calibration sample is a known qualitative quantity. The calibrating step comprises calibrating the quantity of the analyte in the test sample against the qualitative and determined quantities of the analytes in the aliquots of the calibration sample. In a particular embodiment, the qualitative quantity is an expected range of quantities of analyte in a subject having a particular state, such as a healthy or diseased state. Assays which provide such calibration samples for relative quantitation have wide range of applications including biomarker discovery, industrial microbiology, pharmaceutical and food manufacture and the diagnosis and management of human and veterinary disease.

Relative quantitation experiments are often useful when analysing complex biological samples such as blood plasma. In a specific embodiment, a large amount of entire human blood plasma is split into several (i.e. four) aliquots and individually labelled with different isobaric mass labels. For instance, one could utilise the TMTsixplex to produce four labelled aliquots of blood plasma. $TMT^6$-128, $TMT^6$-129, $TMT^6$-130, $TMT^6$-131 would be used for labelling. All individual samples of a blood plasma study are labelled with one further different version of this isobaric mass tag, i.e. $TMT^6$-126. The aliquots of blood plasma can now be used to generate a calibration curve, for instance by mixing the four aliquots in a 0.5 to 1 to 2 to 5 µL ratio to produce a calibration sample, and then adding 1 µl of the study sample. By combining the sample with the calibration sample comprising four differentially labelled aliquots, virtually all experiments performed with this material will result in groups of five marker-ions—four from the calibration sample and one from the test sample. Thus, the entire proteome can be used in a four-point calibration curve. If all test samples of the study are spiked with the identical amount of the calibration sample, relative quantification across all study samples becomes possible. Since the calibration sample can be used by multiple laboratories, cross-study and cross-laboratory comparisons are possible.

Whereas the absolute quantity of an analyte might not be known, the % change in quantity can be calculated from the calibration curve. Depending on the application, the ratio and width of the calibration curve can be adjusted.

In a preferred embodiment, the quantity of analyte in each different aliquot of the calibration sample is selected to reflect the known or suspected variation of the analyte in the test sample. In a still further preferred embodiment, aliquots are provided which comprise the analyte in quantities which correspond to the upper and lower limits, and optionally intermediate points within a range of the known or suspected quantities of the analyte found in test samples of healthy or diseased subjects.

Because each analyte is quantified independently of all other analytes in the sample it is conceivable to prepare multiple sets of calibration samples each at extremely different concentrations to all other calibration samples, so enhancing the dynamic, range of the experiment. It is also possible to prepare a number of reference biomolecules for each analyte wherein each biomolecule is provided in a range of overlapping quantities thereby extending the total range of the standard curve for a given analyte. As an example a number of different tryptic peptides from a target protein may be selected for use as reference standards based on their performance in a tandem mass spectrometer. The reference peptides may be selected on the basis of the ion intensity of the ion corresponding to the peptide in a mass spectrum or on the basis of the signal-to-noise ratio in the area of the spectrum in which the ion corresponding to the peptide appears. Alternatively the reference peptides may be selected so as to avoid peptides which have isobaric species. The selection of proteotypic peptides, i.e. peptides which are only present in a particular protein is particularly favoured.

If each standard peptide is independently labelled with up to five different members of a sixplex set of isobaric mass tags these may be mixed in different ratios to provide a five-point standard curve. The same isobaric mass labels may be used to label second, third, fourth or more standard peptides each of which may be mixed in different ratios covering a range of concentrations different to that covered by each of the other reference peptides for the same analyte.

A different calibration curve is produced for each peptide derived from the target protein, each calibration curve covering a different range of concentrations. The concentration of each peptide is then determined from their respective calibration curve, and this can be related back to the concentration of the target protein. For some of the calibration curves, the quantity of the peptide in the test sample may fall in the middle of the calibration curve, providing an accurate determination of its actual quantity in the sample. For other calibration curves covering a different range in concentrations, the quantity of the peptide in the test sample may fall outside the range of the calibration curve. By using multiple peptides which are each derived from a single analyte of interest, we can produce multiple calibration curves which can be related to the same analyte and then choose the most accurate calibration to determine the concentration of the analyte in the test sample from the concentration of one or more of the peptides. In this way a broad dynamic range may be covered without compromising assay sensitivity.

The calibration sample may comprise a normal quantity of an analyte. The quantity of the analyte in the calibration sample may indicate that a plant, animal, or preferably a human is healthy. Alternatively, the calibration sample may comprise an analyte in a quantity that indicates the presence and/or stage of a particular disease. In a further embodiment, the calibration sample comprises an analyte in a quantity that indicates the efficacy and/or toxicity of a therapy. Standard panels of known markers of a particular trait such as presence and/or stage of disease, response to therapy, and/or toxicity are prepared. Calibration samples comprising body fluids or tissue extracts labelled with an isobaric mass tag could be prepared from patients with well characterised disease including but not limited to tumours, neurodegeneration, cardiovascular, renal, hepatic, respiratory, metabolic, inflammatory, and infectious diseases. Known amounts of such samples are added to multiple test samples in such a manner that for a series of analyses ion intensities in the mass spectrum can be normalised based on the ion intensity of the common calibration sample, thereby providing more accurate comparisons between the separate analyses, reducing the analytical variability of the study.

In the case of coronary medicine a series of peptides derived from the tryptic digestion of known heart disease markers such as myoglobin, troponin-I, CK-MB, BNP, pro-BNP and NT-pro-BNP are produced synthetically and split into three aliquots. Each aliquot of each reference peptide is, for example, labelled with one of three isobaric mass tags from a set of such isobaric mass tags wherein all tags in the set have substantially the same aggregate mass as determined by mass spectrometry and wherein each tag in the set releases a mass marker ion of unique mass on collision induced dissociation in a mass spectrometer. Each unique reference peptide-mass tag molecule is then added to a carrier solution such as a mass spectrometric-compatible buffer at a known concentration such that the concentration of the three differentially labelled aliquots of the same reference peptide are different, and that the differences span the normal biological concentrations of the parent protein in patients with cardiac disease. The resultant reference peptide panel is added at a defined volumetric ratio with a test sample that has been labelled with a fourth isobaric mass tag from the same set of isobaric mass tags used to label the reference peptides. The spiked sample is then subjected to tandem mass spectrometry wherein the survey scan is performed in a directed manner to only identify those precursor ions of characteristic retention time and mass correlating to each of the isobarically labelled reference peptides. For each selected ion the mass spectrum will contain marker ions derived from the high, medium and low concentration reference peptides and the test sample.

A simple standard curve is easily constructed from the reference peptide marker ion intensities and the fourth marker ion from the same peptide in the test sample can be read against the calibration curve. By this means the absolute concentration of multiple biologically relevant proteins can be determined in a single experiment. The skilled artisan will be aware that the number of different proteins for which reference peptides are prepared need not be particularly limited and will be in the range of 1-100 and most preferably 1-50. Similarly the number of representative peptides may be in the range of 1-20, preferably 1-10, more preferably 1-5 and most preferably 1-3. It would be understood by the skilled artisan that the example described above is a general example and the principles described therein may be applied to known markers of any disease and applied for disease diagnosis, monitoring of disease progression or monitoring the response of a patient to treatment.

A further application is in the use of these calibration samples in time course experiments. The "Status" of a sample with respect to time course can be established if the different aliquots (four) are from four different time points, such as time zero, 1 hour, 8 hours, and 24 hours into an experiment (drug challenge in mice and man, induction of fermentation in E. coli and yeast), also on a longer time scale of weeks and months for development or treatment response of chronic diseases.

The skilled artisan will understand that the nature of the isobaric mass label is not particularly limiting. Various suitable isobaric mass labels are known in the art such as Tandem Mass Tags (Thompson et al., 2003, Anal. Chem. 75(8): 1895-1904 (incorporated herein by reference) disclosed in WO 01/68664 (incorporated herein by reference) and WO 03/025576 (incorporated herein by reference), iPROT tags disclosed in U.S. Pat. No. 6,824,981 (incorporated herein by reference) and iTRAQ tags (Pappin et al., 2004, Methods in Clinical Proteomics Manuscript M400129-MCP200 (incorporated herein by reference)). Any of these isobaric mass labels are suitable for preparation of the samples and calibration samples and performing the methods of the current invention.

Although the structure of the mass labels used in the present invention is not especially limited, providing that they are isobaric and have mass spectrometrically distinct mass marker groups (moieties), in preferred embodiments the mass label comprises the following structure:

X-L-M wherein X is a mass marker moiety, L is a cleavable linker and M is a mass normalisation moiety. L may be a single bond, or part of X, or part of M. These mass labels may be attached at any point to the analyte in the test or calibration samples, e.g. through M, L or X. Preferably, they are attached through M, e.g. the label would comprise the structure:

(X-L-M)-

This is typically effected by including a reactive functionality in the mass label to allow it to bind to the analyte, e.g.:

X-L-M-reactive functionality

When the labels comprise a reactive functionality these are termed reactive mass labels.

The reactive functionality for attaching the mass label to the analyte is not especially limited and may comprise any appropriate reactive group.

The term mass label used in the present context is intended to refer to a moiety suitable to label an analyte for determination. The term label is synonymous with the term tag.

The term mass marker moiety used in the present context is intended to refer to a moiety that is to be detected by mass spectrometry. The term mass marker moiety is synonymous with the term mass marker group or the term reporter group. The components of the mass marker moiety of this invention are preferably fragmentation resistant so that the site of fragmentation of the markers can be controlled by the introduction of a linkage that is easily broken by Collision Induced Dissociation (CID), Surface Induced Dissociation, Electron Capture Dissociation (ECD), Electron Transfer Dissociation (ETD), or Fast Atom Bombardment. In the most preferred embodiment, the linkage is easily broken by CID.

The term mass normalisation moiety used in the present context is intended to refer to a moiety that is not necessarily to be detected by mass spectrometry, but is present to ensure that a mass label has a desired aggregate mass. The mass normalisation moiety is not particularly limited structurally, but merely serves to vary the overall mass of the mass label.

In a preferred embodiment the aggregate molecular weight of the mass label is 600 Daltons or less, more preferably 500 Daltons or less, still more preferably 400 Daltons or less, most preferably from 300 to 400 Daltons. Particularly preferred molecular weights of the mass labels are 324, 338, 339 and 380 Daltons. These preferred embodiments are particularly advantageous because the small size of the mass labels means that the size of the peptide to be detected is minimally increased when labelled with the mass label.

In a preferred embodiment, the molecular weight of the mass marker moiety is 300 Daltons or less, preferably 250 Daltons or less, more preferably 100 to 250 Daltons, most preferably 100-200 Daltons. These preferred embodiments are particularly advantageous because the small size of the mass marker moiety means that it produces a peak in the silent region of a mass spectrum, which allows the mass marker to be easily identified from the mass spectrum and also allows sensitive quantification.

Particularly preferred molecular weights of the mass marker moiety are 125, 126, 153 and 154 Daltons, or weights in which one or more or all of the 12C atoms are replaced by 13C atoms, e.g. for a non-substituted mass marker moiety having a weight of 125, masses for its substituted counterparts would be 126, 127, 128, 129, 130 and 131 Daltons for substitution with 1, 2, 3, 4, 5 and 6 13C atoms respectively and/or one or more or all of the 14N atoms are replaced by 15N atoms.

The term silent region of a mass spectrum used in the present context is intended to refer to the region of a mass spectrum with low background "noise" caused by peaks relating to the presence of fragments generated by fragmentation of the labelled peptides. Thus, the term silent region is intended to refer to the region of the mass spectrum with low "noise" caused by peaks relating to the peptide to be detected. For a peptide or protein, the silent region of the mass spectrum is less than 200 Daltons.

The present inventors have also discovered that the reactive mass labels defined above are easily and quickly reacted with a protein to form a labelled protein.

In the present invention a set of two or more mass labels is employed. The labels in the sets are isobaric mass labels each having a mass marker of a different mass. Thus, each label in the set is as defined above and wherein each mass normalisation moiety ensures that a mass label has a desired aggregate mass, and wherein the set comprises mass labels having a mass marker moiety, each mass marker moiety having a mass different from that of all other mass marker groups in the set, and each label in the set having a common aggregate mass; and wherein all the mass labels in the set are distinguishable from each other by mass spectroscopy.

The term "isobaric" means that the mass labels have substantially the same aggregate mass as determined by mass spectrometry. Typically, the average molecular masses of the isobaric mass labels will fall within a range of ±0.5 Da of each other. The term "labels" shall be synonymous with the term "tags". In the context of the present invention, the skilled addressee will understand that the term "mass marker moiety" and the term "reporter group" can be used interchangeably.

The number of labels in the set is not especially limited, provided that the set comprises a plurality of labels. However, it is preferred if the set comprises two or more, three or more, four or more, or five or more labels, more preferably six or more labels, most preferably eight or more labels.

The term aggregate mass in the present context refers to the total mass of the mass label, i.e. the sum of the masses of the mass marker moiety, the cleavable linker, the mass normalisation moiety and any other components of the mass label.

The mass of the mass normalisation moiety will be different in each mass label in the set. The mass of the mass normalisation moiety in each individual mass label will be equal to the common aggregate mass minus the mass of the particular mass marker moiety in that mass label and minus the mass of the cleavable linker.

All mass labels in the set are distinguishable from each other by mass spectroscopy. Therefore, a mass spectrometer can discriminate between the mass labels, i.e. the peaks derived from individual mass labels can be clearly separated from one another. The difference in mass between the mass marker groups means that a mass spectrometer can discriminate between ions derived from different mass labels or mass marker groups.

The present invention may also employ an array of mass labels, comprising two or more sets of mass labels as defined above, wherein the aggregate mass of each of the mass labels in any one set is different from the aggregate mass of each of the mass labels in every other set in the array.

In preferred embodiments of the invention, the array of mass labels are preferably all chemically identical (substantially chemically identical). The term "substantially chemically identical" means that the mass labels have the same chemical structure, into which particular isotopic substitutions may be introduced or to which particular substituents may be attached.

In further preferred embodiments of this invention, the mass labels may comprise a sensitivity enhancing group. The mass labels are preferably of the form:

sensitivity enhancing group—X-L-M-reactive functionality

In this example the sensitivity enhancing group is usually attached to the mass marker moiety, since it is intended to increase the sensitivity of the detection of this moiety in the mass spectrometer. The reactive functionality is shown as being present and attached to a different moiety than the sensitivity enhancing group. However, the mass labels need not be limited in this way and in some cases the sensitivity enhancing group may be attached to the same moiety as the reactive functionality.

Preferred structures of mass labels employed to tag the analytes in the present invention will now be described in more detail.

In preferred embodiments X is a mass marker moiety comprising the following group:

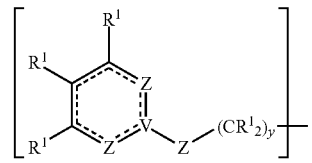

wherein the cyclic unit is aromatic or aliphatic and comprises from 0-3 double bonds each Z is independently N, $N(R^1)$, $C(R^1)$, CO, $CO(R^1)$ (i.e. $-O-C(R^1)-$ or $-C(R^1)-O-$), $C(R^1)_2$, O or S; V is N, C or $C(R^1)$; each $R^1$ is independently a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10.

In the above general formula, when Z is $C(R^1)_2$, each $R^1$ on the carbon atom may be the same or different (i.e. each $R^1$ is independent). Thus the $C(R^1)2$ group includes groups such as $CH(R^1)$, wherein one $R^1$ is H and the other $R^1$ is another group selected from the above definition of $R^1$.

In the above general formula, the bond between V and the non-cyclic Z may be single bond or a double bond depending upon the selected V and Z groups in this position. For example, when V is N or $C(R^1)$ the bond from V to the non-cyclic Z must be a single bond. When V is C, the bond from V to the non-cyclic Z may be a single bond or a double bond depending upon the selected non-cyclic Z group and cyclic Z groups. When the non-cyclic Z group is N or $C(R^1)$ the bond from non-cyclic Z to V is a single bond or if y is 0 may be a double bond depending on the selected V group and the group to which the non-cyclic Z is attached. When the non-cyclic Z is $N(R^1)$, $CO(R^1)$, CO, $C(R^1)_2$, O or S the bond to V must be a single bond. The person skilled in the art may easily select suitable V, Z and $(CR^1_2)_y$ groups with the correct valencies (single or double bond links) according to the above formula.

The substituents of the mass marker moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

The cleavable linker of the mass label used in the present invention is not especially limited. Preferably, the cleavable linker is a linker cleavable by Collision Induced Dissociation, Surface Induced Dissociation, Electron Capture Dissociation (ECD), Electron Transfer Dissociation (ETD), or Fast Atom Bombardment. In the most preferred embodiment, the linkage is cleavable by CID. The linker may comprise an amide bond.

In the discussion above and below reference is made to linker groups which may be used to connect molecules of interest to the mass label compounds used in this invention. A variety of linkers is known in the art which may be introduced between the mass labels of this invention and their covalently attached biological molecule. Some of these linkers may be cleavable. Oligo- or poly-ethylene glycols or their derivatives may be used as linkers, such as those disclosed in Maskos, U. & Southern, E.M. Nucleic Acids Research 20: 1679-1684, 1992. Succinic acid based linkers are also widely used, although these are less preferred for applications involving the labelling of oligonucleotides as they are generally base labile and are thus incompatible with the base mediated de-protection steps used in a number of oligonucleotide synthesisers.

Propargylic alcohol is a bifunctional linker that provides a linkage that is stable under the conditions of oligonucleotide synthesis and is a preferred linker for use with this invention in relation to oligonucleotide applications. Similarly 6-aminohexanol is a useful bifunctional reagent to link appropriately functionalised molecules and is also a preferred linker.

A variety of known cleavable linker groups may be used in conjunction with the compounds employed in this invention, such as photocleavable linkers. Ortho-nitrobenzyl groups are known as photocleavable linkers, particularly 2-nitrobenzyl esters and 2-nitrobenzylamines, which cleave at the benzylamine bond. For a review on cleavable linkers see Lloyd-Williams et al., Tetrahedron 49, 11065-11133, 1993, which covers a variety of photocleavable and chemically cleavable linkers.

WO 00/02895 discloses the vinyl sulphone compounds as cleavable linkers, which are also applicable for use with this invention, particularly in applications involving the labelling of polypeptides, peptides and amino acids. The content of this application is incorporated by reference.

WO 00/02895 discloses the use of silicon compounds as linkers that are cleavable by base in the gas phase. These linkers are also applicable for use with this invention, particularly in applications involving the labelling of oligonucleotides. The content of this application is incorporated by reference.

The structure of the mass normalization moiety of the mass label used in the present invention is not particularly limited provided that it is suitable for ensuring that the mass label has a desired aggregate mass. However, the mass normalization moiety preferably comprises a straight or branched $C_1$-$C_{20}$ substituted or unsubstituted aliphatic group and/or one or more substituted or unsubstituted amino acids.

Preferably, the mass normalisation moiety comprises a $C_1$-$C_6$ substituted or unsubstituted aliphatic group, more preferably a $C_1$, $C_2$, $C_3$, $C_4$, $C_5$ substituted or unsubstituted aliphatic group, still more preferably a $C_1$, $C_2$, or $C_5$ substituted or unsubstituted aliphatic group or a $C_1$ methyl substituted group.

The one or more substituted or unsubstituted amino acids may be any essential or non-essential naturally occurring amino acids or non-naturally occurring amino acids. Preferred amino acids are alanine, β-alanine and glycine.

The substituents of the mass normalisation moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

In one embodiment of the present invention wherein the method comprises a step of labelling the samples, the labelling step comprises a step of reacting the analyte with a reactive mass label, wherein the reactive mass label comprises a mass label and a reactive functionality.

The reactive mass labels typically used in the present invention for labelling and detecting a biological molecule by mass spectroscopy comprise a reactive functionality for facilitating attachment of or for attaching the mass label to a biological molecule and a mass label as defined above. In preferred embodiments of the present invention, the reactive functionality allows the mass label to be reacted covalently to an analyte, preferably an amino acid, peptide or polypeptide. The reactive functionality may be attached to the mass labels via a linker which may or may not be cleavable. The reactive functionality may be attached to the mass marker moiety of the mass label or the mass normalization moiety of the mass label.

A variety of reactive functionalities may be introduced into the mass labels used in this invention. The structure of the reactive functionality is not particularly limited provided that it is capable of reacting with one or more reactive sites on the biological molecule to be labelled. The reactive functionality is preferably a nucleophile or an electrophile.

In the simplest embodiments this may be an N-hydroxysuccinimide ester. An N-hydroxysuccinimide activated mass label could also be reacted with hydrazine to give a hydrazide reactive functionality, which can be used to label periodate oxidised sugar moieties, for example. Amino-groups or thiols can be used as reactive functionalities in some applications. Lysine can be used to couple mass labels to free carboxyl functionalities using a carbodiimide as a coupling reagent. Lysine can also be used as the starting point for the introduction of other reactive functionalities into the mass labels of this invention. The thiol-reactive maleimide functionality can be introduced by reaction of the lysine epsilon amino group with maleic anhydride. The cysteine thiol group can be used as the starting point for the synthesis of a variety of alkenyl sulphone compounds, which are useful protein labelling reagents that react with thiols and amines. Compounds such as aminohexanoic acid can be used to provide a spacer between the mass modified mass marker moiety or mass normalisation moiety and the reactive functionality.

Table 1 below lists some reactive functionalities that may be reacted with nucleophilic functionalities which are found in biomolecules to generate a covalent linkage between the two entities. Any of the functionalities listed below could be introduced into the compounds of this invention to permit the mass markers to be attached to a biological molecule of interest. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
|---|---|---|
| —SH | —SO₂—CH=CR₂ | —S—CR₂—CH₂—SO₂— |
| —NH₂ | —SO₂—CH=CR₂ | —N(CR₂—CH₂—SO₂—)₂ or —NH—CR₂—CH₂—SO₂— |
| —NH₂ | ![succinimidyl ester] | —CO—NH— |
| —NH₂ | ![benzotriazolyl ester] | —CO—NH— |
| —NH₂ | —NCO | —NH—CO—NH— |
| —NH₂ | —NCS | —NH—CS—NH— |
| —NH₂ | —CHO | —CH₂—NH— |
| —NH₂ | —SO₂Cl | —SO₂—NH— |
| —NH₂ | —CH=CH— | —NH—CH₂—CH₂— |
| —OH | —OP(NCH(CH₃)₂)₂ | —OP(=O)(O)O— |

In a preferred embodiment of the present invention the reactive functionality comprises the following group:

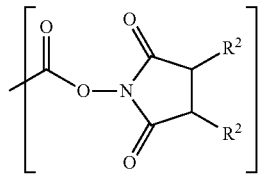

wherein each $R^2$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group.

The substituents of the reactive functionality are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

In a more preferred embodiment the reactive functionality comprises the following group:

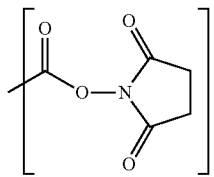

In a preferred embodiment of the present invention the reactive mass label has one of the following structures:

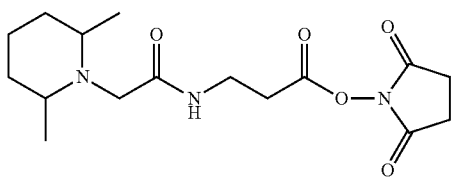 [SMILES: CC1CCCC(C)N1CC(=O)NCCC(=O)ON1C(=O)CCC1=O]

3-[2-(2,6-Dimethyl-piperidin-1-yl)-acetylamino]-propanoic acid-(2,5-dioxo-pyrrolidine-1-yl)-ester (DMPip-βAla-OSu)

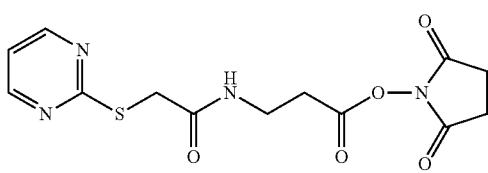 [SMILES: O=C(CSc1ncccn1)NCCC(=O)ON1C(=O)CCC1=O]

3-[2-(Pyrimidin-2-ylsulfanyl)-acetylamino]-propanoic acid-(2,5-dioxo-pyrrolidine-1-yl)-ester (Pyrm-βAla-OSu)

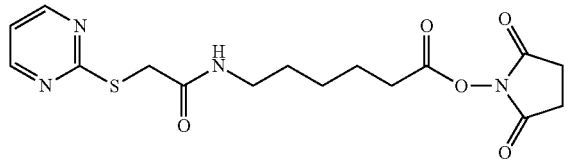 [SMILES: O=C(CSc1ncccn1)NCCCCCC(=O)ON1C(=O)CCC1=O]

6-[(Pyrimidin-2-ylsulfanyl)-acetylamino]-hexanoic acid-(2,5-dioxo-pyrrolidine-1-yl)-ester (Pyrm-C6-OSu)

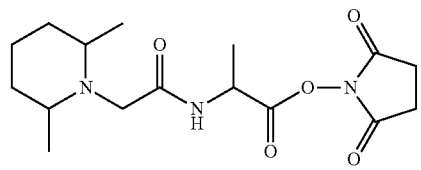 [SMILES: CC(NC(=O)CN1C(C)CCCC1C)C(=O)ON1C(=O)CCC1=O]

2-[2-(2,6-Dimethyl-piperidin-1-yl)-acetylamino]-propanoic acid-(2,5-dioxo-pyrrolidine-1-yl)-ester (DMPip-Ala-OSu)

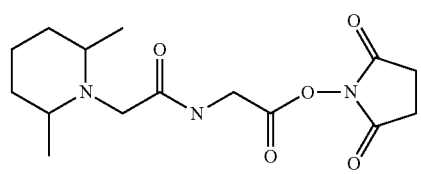 [SMILES: CC1CCCC(C)N1CC(=O)NCC(=O)ON1C(=O)CCC1=O]

[2-(2,6-Dimethyl-piperidin-1-yl)-acetylamino]-acetic acid-(2,5-dioxo-pyrrolidine-1-yl)-ester (Pyrm-Gly-OSu)

In the method according to the present invention, each label in the set has a common aggregate mass and each label in the set has a mass marker moiety of a unique mass.

It is preferred that, each mass marker moiety in the set has a common basic structure and each mass normalisation moiety in the set has a common basic structure, and each mass label in the set comprises one or more mass adjuster moieties, the mass adjuster moieties being attached to or situated within the basic structure of the mass marker moiety and/or the basic structure of the mass normalisation moiety. In this embodiment, every mass marker moiety in the set comprises a different number of mass adjuster moieties and every mass label in the set has the same number of mass adjuster moieties.

Throughout this description, by common basic structure, it is meant that two or more moieties share a structure which has substantially the same structural skeleton, backbone or core. The skeleton comprises the mass marker moiety of the formula given above or the mass normalisation moiety as defined above. The skeleton may additionally comprise a number of amino acids linked by amide bonds. Other units such as aryl ether units may also be present. The skeleton or backbone may comprise substituents pendent from it, or atomic or isotopic replacements within it, without changing the common basic structure.

In a preferred embodiment the set of mass labels or reactive mass labels according to the invention comprise mass labels having the following structure:

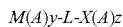

wherein M is a mass normalisation moiety, X is a mass marker moiety, A is a mass adjuster moiety, L is a cleavable linker, y and z are integers of 0 or greater, and y+z is an integer of 1 or greater. Preferably M is a fragmentation resistant group, L is a linker that is susceptible to fragmentation on collision with another molecule or atom and X is preferably a pre-ionised, fragmentation resistant group.

The sum of the masses of M and X is the same for all members of the set. Preferably M and X have the same basic structure or core structure, this structure being modified by the mass adjuster moieties. The mass adjuster moiety ensures that the sum of the masses of M and X is the same for all mass labels in a set, but ensures that each X has a distinct (unique) mass.

The mass adjuster moiety (A) is preferably selected from:
(a) an isotopic substituent situated within the mass marker moiety and/or within the mass normalisation moiety, and
(b) substituent atoms or groups attached to the mass marker moiety and/or attached to the mass normalisation moiety.

Preferably the mass adjuster moiety is selected from a halogen atom substituent, a methyl group substituent, and $^2$H, $^{15}$N, $^{18}$O or $^{13}$C isotopic substituents.

In one preferred embodiment the present invention, each mass label in the set of mass labels as defined above has the following structure:

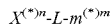

wherein X is the mass marker moiety, L is the cleavable linker, M is the mass normalisation moiety, * is an isotopic mass adjuster moiety, and n and m are integers of 0 or greater such that each label in the set comprises a mass marker moiety having a unique mass and each label in the set has a common aggregate mass.

It is preferred that X comprises the following group:

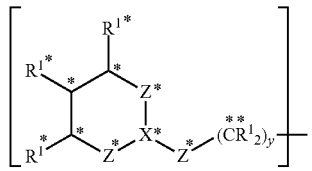

wherein $R^1$, Z, X and y are as defined above and each label in the set comprises 0, 1 or more * such that each label in the set comprises a mass marker moiety having a unique mass and each label in the set has a common aggregate mass.

In a further preferred embodiment, the reactive mass labels of the present invention comprise the following reactive functionality group:

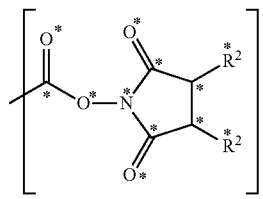

wherein $R^2$ is as defined above and the set comprises 0, 1 or more * such that each label in the set comprises a mass marker moiety having a unique mass and each label in the set has a common aggregate mass.

In all of the above preferred formulae, it is particularly preferred that the isotopic species * is situated within the mass marker moiety and/or the linker and/or the mass adjuster moiety, rather than on any reactive moiety that is present to facilitate attaching the label to an analyte. The number of isotopic substituents is not especially limited and can be determined depending on the number of labels in the set. Typically, the number of * species is from 0-20, more preferably from 0-15 and most preferably from 1-10, e.g. 1, 2, 3, 4, 5, 6, 7 or 8. In a set of two labels, it is preferred that the number of species * is 1, whilst in a set of 5 labels, it is preferred that the number is 4, whilst in a set of 6 labels it is preferred that the number is 5. However, the number may be varied depending upon the chemical structure of the label.

If desired, isotopic variants of S may also be employed as mass adjuster moieties, if the labels contain one or more sulphur atoms.

In a particularly preferred embodiment wherein the mass adjuster moiety is $^{15}$N or $^{13}$C the set of reactive mass labels comprises two mass labels having the following structures:

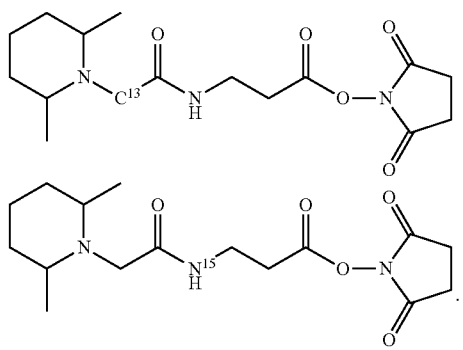

The above mass labels form an example of a set of duplex Tandem Mass Tags.

In an alternative particularly preferred embodiment wherein the mass adjuster moiety is $^{15}$N or $^{13}$C the set of reactive mass labels comprises the set comprises five mass labels having the following structures:

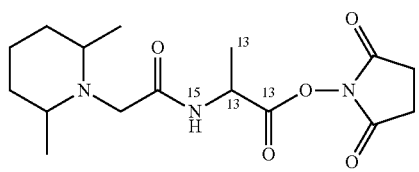

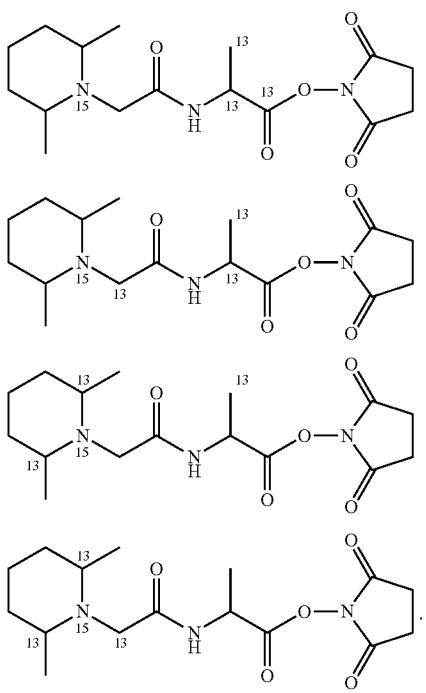

The above mass labels form an example of a set of fiveplex Tandem Mass Tags.

In an alternative particularly preferred embodiment wherein the mass adjuster moiety is $^{15}$N or $^{13}$C the set of reactive mass labels comprises six mass labels I-VI having the following structures, or stereoisomers of these structures:

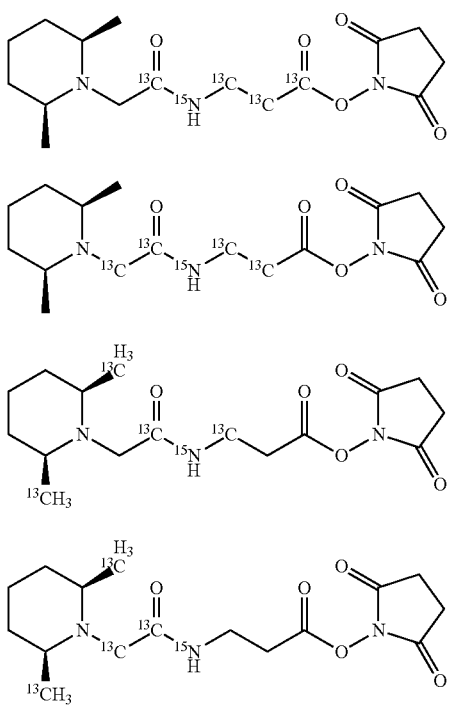

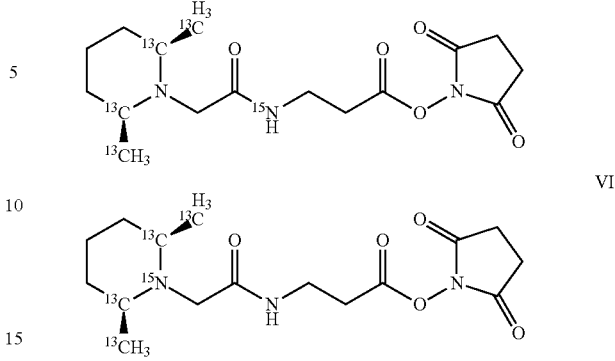

The above mass labels form an example of a set of sixplex Tandem Mass Tags.

The method according to the present invention may comprise a further step of separating the target analyte or a fragment thereof from other components in the samples. This step of separating may be carried out prior to step (a), after step (a) but before step (b) or during step (b).

The method may also comprise a step of digesting each sample with at least one enzyme to digest components of the samples. This step of digesting may be carried out prior to step (a), after step (a) but before step (b) or during step (b). In one embodiment the samples are labeled with the isobaric mass labels prior to digestion. In another embodiment the samples are labeled after digestion.

In a further embodiment, the mass labels used in the method further comprise an affinity capture ligand. The affinity capture ligand of the mass label binds to a counter-ligand so as to separate the isobarically labeled analytes from the unlabelled analytes prior to step (a), after step (a) but before step (b) or during step (b). The affinity capture ligand provides a means of enrichment of the analytes of interest, thereby increasing analytical sensitivity.

Affinity capture ligands are ligands which have highly specific binding partners. These binding partners allow molecules tagged with the ligand to be selectively captured by the binding partner. Preferably a solid support is derivitised with the binding partner so that affinity ligand tagged molecules can be selectively captured onto the solid phase support. A preferred affinity capture ligand is biotin, which can be introduced into the mass labels of this invention by standard methods known in the art. In particular a lysine residue may be incorporated after the mass marker moiety or mass normalization moiety through which an amine-reactive biotin can be linked to the mass labels (see for example Geahlen R. L. et al., Anal Biochem 202(1): 68-70, "A general method for preparation of peptides biotinylated at the carboxy terminus." 1992; Sawutz D. G. et al., Peptides 12(5): 1019-1012, "Synthesis and molecular characterization of a biotinylated analogue of [Lys]bradykinin." 1991; Natarajan S. et al., Int J Pept Protein Res 40(6): 567-567, "Site-specific biotinylation. A novel approach and its application to endothelin-1 analogues and PTH-analogue.", 1992). Iminobiotin is also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the c-myc epitope, for which selective monoclonal antibodies exist as counter-ligands. Alternatively, an antibody or other binding agent with specificity for the mass label structure may be produced by methods known to one skilled in the art. An affinity matrix may then be constructed by attaching such binding agent onto a solid support such as a bead, well, or planar surface in a lateral flow device. Labelled analytes are then purified by contacting them with the affinity matrix in conditions whereby the mass labeled analytes are bound by the binding agents and retained whilst all unlabeled materials are removed, e.g. by washing. Finally, the captured analytes may be recovered by adjusting the conditions to those favouring release of the captured mass labeled analyte such as low pH or high salt. Preferably, conditions of low pH are used to avoid the need for subsequent removal of salt ions that may interfere with MS. Metal ion binding ligands such as hexahistidine (SEQ ID NO: 11), which readily binds $Ni^{2+}$ ions, are also applicable. Chromatographic resins, which present iminodiacetic acid chelated $Ni^{2+}$ ions are commercially available, for example. These immobilised nickel columns may be used to capture mass labels. As a further alternative, an affinity capture functionality may be selectively reactive with an appropriately derivatised solid phase support. Boronic acid, for example, is known to selectively react with vicinal cis-dials and chemically similar ligands, such as salicylhydroxamic acid.

The method according to the invention may further include the step of separating the isobarically labeled analytes electrophoretically or chromatographically prior to step (a), after step (a) but before step (b) or during step (b). In a preferred embodiment, strong cation exchange chromatography is used.

In a further aspect of the invention, one of the samples comprises a trigger aliquot which comprises a trigger analyte. The trigger analyte is preferably labelled with a non-isobaric mass label and the method comprises a further step after step (b) and prior to step (c) of detecting ions having a mass to charge ratio equivalent to the mass to charge ratio of the trigger analyte, wherein when ions having a mass to charge ratio equivalent to the mass to charge ratio of the trigger analyte are detected step (c) is initiated at the m/z of the first mass to charge ratio. The quantity of trigger analyte in the trigger aliquot is sufficient to serve as a trigger during the detection step. Preferably one or the aliquots of the calibration sample is the trigger aliquot.

The step of detecting ions having the mass to charge ratio equivalent to the mass to charge ratio of the trigger analyte may comprise precursor ion scanning Typically, this involves allowing all ions to pass from a first mass analyser into a collision cell, where CID occurs on all of the analytes in the sample instead of a particular selected ion as in conventional MS/MS. The final mass analyser is set to detect only the reporter ion from the trigger, which can be used as an indicator that an analyte of interest is entering the mass spectrometer at any particular point in time. When the reporter ion from the trigger is detected the mass spectrometer is then set to perform the method of the present invention on the target analyte(s) of interest including acquisition across the full m/z range of mass marker groups present.

In a preferred embodiment, the presence of a reporter ion from the trigger indicates that an analyte of interest is eluting from an LC column. This would "trigger" the execution of a pre-defined MS/MS/MS experiment according to the present invention.

The trigger aliquot may be labelled with an isobaric mass label. Alternatively the trigger may not be an analyte labelled with an isobaric mass label. The trigger may be any other labelled analyte which co-elutes, or substantially co-elutes with the labelled analyte of interest during LC. The label of the trigger analyte may have a different mass to that of the isobaric mass labels of the calibration sample. For example, in one embodiment, the calibration sample comprises aliquots of an analyte differentially labelled with isobaric mass labels, and further comprises an aliquot of the analyte which is labelled with a chemically identical but isotopically distinct mass label, preferably with a mass difference of 5 Da from that of the isobaric mass labels. The isotopically distinct mass label could then serve as the "trigger". During the MS phase of the analysis each analyte present in the calibration sample bearing the isotopically distinct and isobaric labels will appear as a pair of peaks separated by the mass difference between the isobaric and isotopically distinct labels and wherein the analyte bearing the isotopically distinct label is present in a readily detectable amount. The mass spectrometer is programmed to perform a dedicated MS/MS/MS experiment on the isobarically labelled analyte in such pairs, thereby triggering the quantitative analysis of the analytes of interest.

In a preferred embodiment, the isotopically distinct mass label trigger comprises no isotopic substituents, and the isobaric mass labels comprise a plurality of isotopic substituents, preferably $^2H$, $^{15}N$, $^{18}O$ or $^{13}C$ isotopic substituents. This provides a mass difference between the analytes of the calibration sample labelled with isobaric mass labels and the analyte labelled with the trigger label. Since the trigger label comprises no isotopic substituents, this label can be used in large quantities if required without the need for costly isotope labelling.

The quantity analyte in the trigger aliquot is preferably larger than the quantity of analyte present in the other samples including test samples and calibration samples. A larger quantity of trigger analyte compared to analytes in the other samples ensures that the trigger analyte will be detected first and thereby trigger a scan for selection of ions having the first mass to charge ratio in step (c) according to the method of the present invention. Preferably the ratio of the quantity of the analyte in the trigger aliquot compared to the quantity of analyte in the other samples is 2:1 or more, more preferably 3:1 or more, more preferably 9:1 or more and most preferably 27:1 or more. A higher quantity of the analyte in the trigger aliquot compared to the analyte in the other samples is advantageous because the detection of the trigger analyte is facilitated. For example, as shown in FIGS. 31a to 31d, the higher the ratio of trigger aliquot ($TMT^0$) compared to $TMT^6$ labelled plasma, the larger the time period between the detection of the trigger and the following leading edges of each peak shown in the chromatogram.

The present invention also provides a mass spectrometric device for assaying one or more target analytes, wherein the device comprises:
  (i) a means for introducing two or more samples which may comprise the one or more target analytes, wherein each sample is differentially labelled with a mass label or a combination of mass labels, wherein each mass label is an isobaric mass label comprising a mass spectrometrically distinct mass marker group;
  (ii) a means for selecting ions having a first mass to charge ratio equivalent to a target analyte labelled with a specific number of the mass labels;
  (iii) a means for fragmenting ions of the first mass to charge ratio into a plurality of fragment ions, wherein a proportion of the plurality of fragment ions comprise at least one intact mass label;

(iv) a means for selecting ions of a second mass to charge ratio equivalent to a fragment of the target analyte comprising at least one intact mass label;
(v) a means for fragmenting ions of the second mass to charge ratio into a plurality of further fragment ions, wherein a proportion of the further fragment ions are ions of mass marker groups of the mass labels; and
(vi) a means suitable for selecting the ions of a range of mass to charge ratios equivalent to the range of mass to charge ratios of the mass marker groups and suitable for producing a mass spectrum of the mass marker groups.

The device according to the present invention is advantageous because the means for selecting ions (ii), (iv) and (vi) are only required to select a specific mass to charge ratio or small range of mass to charge ratios. This allows the device to be simple, easy to manufacture and of a relatively small size. The device may be manufactured for analysis of a specific target analyte and, therefore the means for selecting ions in steps (ii) and (iv) need only be capable of selecting the first mass to charge ratio and second mass to charge ratio for the specific target analyte. Therefore, the device may be suitable for example to be used at the point of care to for diagnostic purposes and will eliminate the need for samples to be sent away to labs and reduce the time it takes for diagnosis.

The device according to the present invention is suitable for carrying out the method according to the present invention wherein the method comprises a third step of selecting ions equivalent to the range of mass marker groups. Accordingly, the discussion above regarding the method of the present invention including the samples, analytes, mass labels, steps of selecting, steps of fragmenting, producing a mass spectrum and quantifying the target analyte also applies to the device according to the present invention.

The means suitable for selecting the ions of the mass marker groups selects a range of mass to charge ratios which is dependent upon the mass range of the mass marker groups in the mass labels used to label the one or more target analytes. Accordingly this range is not particularly limited. The means suitable for selecting the ions of the mass marker groups may for example selects a 15 Th range of mass to charge ratios, a 8 Th range of mass to charge ratios, a 5 Th range of mass to charge ratios or a 2 Th range of mass to charge ratios.

In a preferred embodiment wherein the means suitable for selecting the ions of the mass marker groups selects an 8 Th range, the range is from 124 to 131.

In a preferred embodiment wherein the means suitable for selecting the ions of the mass marker groups selects a 6 Th range, the range is from 126 to 131 Th, which corresponds to the masses of the mass marker groups of TMTsixplex set of mass labels discussed above.

In a preferred embodiment wherein the means suitable for selecting the ions of the mass marker groups selects a 5 Th range, the range is from 126 to 130 Th, which corresponds to the masses of the mass marker groups of five-plex set of mass labels discussed above.

In a preferred embodiment wherein the means suitable for selecting the ions of the mass marker groups selects a 2 Th range, the range is from 126 to 127 Th, which corresponds to the masses of the mass marker groups of the TMTduplex set of mass labels discussed above.

The means for selecting ions having a first mass to charge ratio is set to select ions equivalent to a target analyte labelled with a specific number of the mass labels, as discussed above with respect to the method according to the present invention. The first mass to charge ratio depends upon the mass of target analyte and the mass labels or combination of mass labels attached. As discussed above with respect to the method according to the present invention; the first mass to charge ratio may be equivalent to the mass to charge ratio of the unfragmented parent ion of the target analyte labelled with a specific number of mass labels. Alternatively, in one embodiment the first mass to charge ratio is equivalent to the mass to charge ratio of a fragment ion of the target analyte labelled with a specific number of mass labels.

The means for selecting ions having a first mass to charge ratio is preferably capable of selecting ions less than or equal to 1500 m/z. The width of the resulting ion beam is preferably adjustable (tunable) to a certain extent to enable the selected ion beam to span a selected mass range, for example 50 Dalton range, 20 Dalton range or a 5 Dalton range. More preferably, the selected ion beam has a unit resolution and only spans 1 Dalton. Most preferably, the width of the selected ions is tuned to less than 0.1 Dalton.

The means for selecting ions having a second mass to charge ratio is set to select ions equivalent to a fragment of the target analyte comprising at least one intact mass label. The second mass to charge ratio depends upon the mass of target analyte and the selected fragment ion which comprises a least one intact mass label. Preferably, the second mass to charge ratio is equivalent to a fragment of the target analyte comprising at least one intact mass label which is unique to the target analyte. As discussed above with respect to the method according to the present invention the second mass to charge ratio may be equivalent to an a-series ion, a b-series ion, a c-series ion, an x-series ion, a y-series ion or a z-series ion. Preferably second mass to charge ratio is a y-ion or b-ion having a higher mass to charge ratio compared to first mass to charge ratio.

The means for selecting ions having a second mass to charge ratio is preferably only capable of selecting ions less than or equal to 1500 Daltons. The means for selecting ions having a second mass to charge ratio is preferably only suitable for selecting ions over a 50 Dalton range, more preferably over a 20 Dalton range and most preferably ion have one mass.

In one embodiment the device according to the present invention comprises a further means of producing a mass spectrum of the plurality of fragment ions from the ions of the first mass to charge ratio. As discussed above with respect to the method according to the present invention, In one embodiment of the present invention the means (ii), (iii), (iv), (v) and (vi) are separate quadrupoles in the mass spectrometer. In an alternative embodiment, the means (ii), (iii), (iv), (v) and (vi) are in a single zone or multiple zones of a mass spectrometer.

The device according to the present invention may comprise ion traps, including linear ion traps such as ABI 4000 QTRAP, Orbitraps, QIT-T of from Kratos (Quadrupol-lontrap-T of). The types of devices discussed above which may be used to carry out the method of the present invention may also be used in the device according to the present invention.

The Invention is described by the following non-limiting examples.

EXAMPLE 1

MS/MS and MS/MS/MS Analysis of Labelled Peptide VATVSLPR (SEQ ID NO: 1)

To demonstrate the principle of the invention including the generation of mass reporter groups from mass labels during MS/MS and MS/MS/MS two samples of a peptide VATVSLPR (SEQ ID NO: 1) were prepared. One sample was labelled with TMT²-126 and the other sample was labelled with TMT²-127.

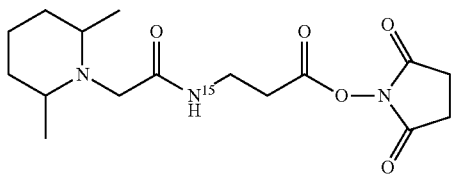

TMT²-126 (mass of reporter group)

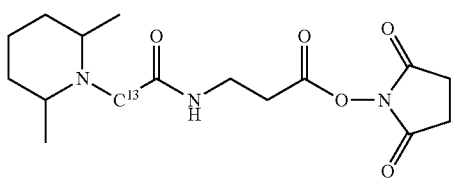

TMT²-127 (mass of reporter group)

The two samples were then mixed together in a 2:1 ratio of TMT²-126:TMT²-127.

The samples mixture was analysed by MS/MS using LCQ deca (Thermo). FIG. 1a shows the MS/MS profile, wherein the b1 ion (325) represents the b1 ion of the peptide (V) attached to an intact mass label and b2 ion (396) represents the b2 ion of the peptide (VA) attached to an intact mass label. FIG. 1b shows a zoom of the mass marker groups (126 and 127) which have been cleaved from the rest of the mass label. The peaks for the mass marker groups in FIG. 1b show the correct ratio for the quantity of each sample 2:1

Figure 2A:
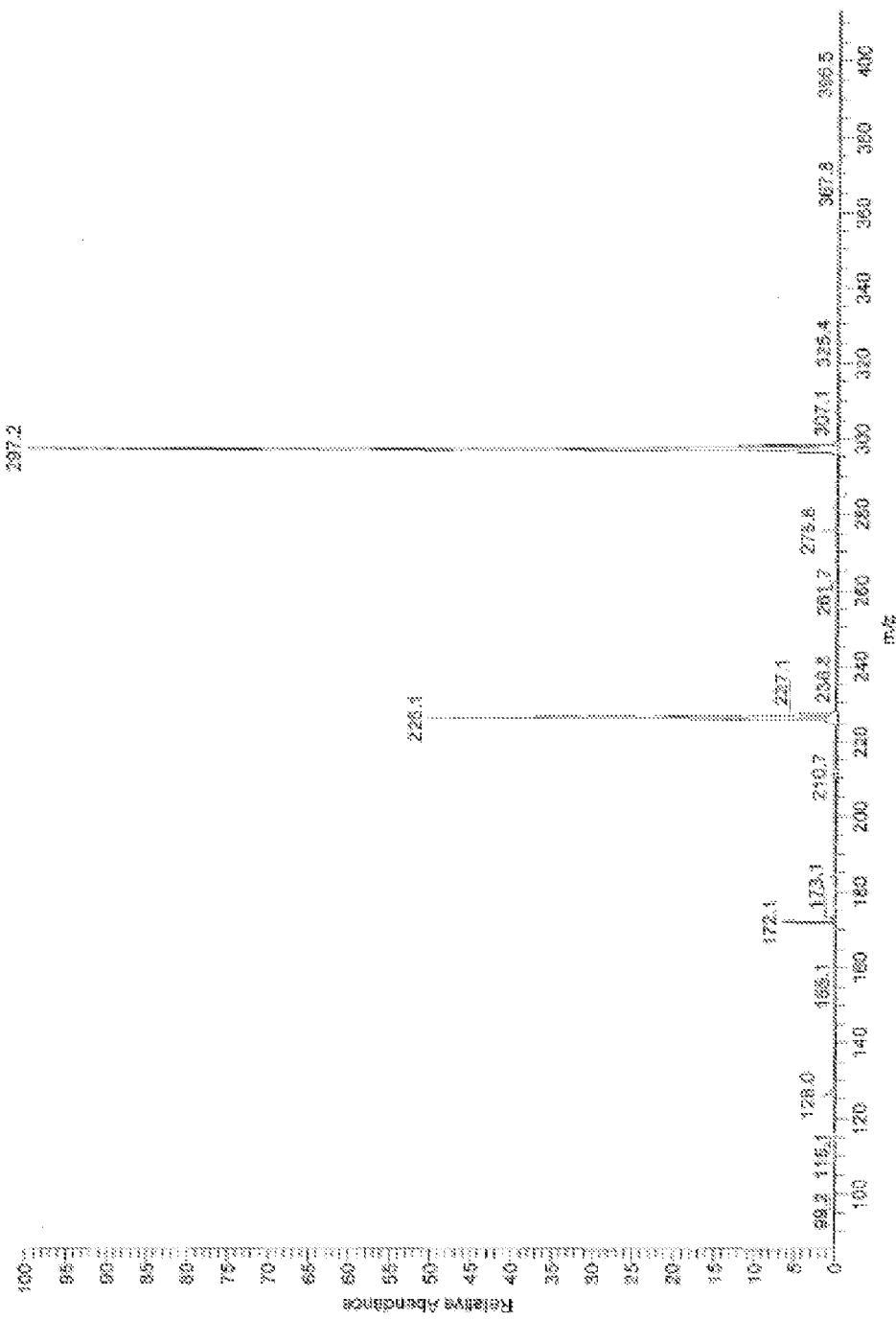
FIG. 2a shows a MS/MS/MS spectrum of the b1-ion of labelled peptide VATVSLPR (SEQ ID NO: 1), as analysed in FIG. 1.

The b1-ion was then selected and subjected to fragmentation using LCQ deca (Thermo) (MS/MS/MS). FIG. 2a shows the MS/MS/MS spectrum of the fragmented b1-ion wherein the peak at 226 is of an intact mass label and the peak at 297 is the a1-ion. FIG. 2b shows a zoom of the mass marker groups (126 and 127) from the MS/MS/MS spectrum which show that the correct ratio of 2:1 is conserved. This shows that a proportion of the fragment ion produced in MS/MS comprised intact mass labels, which could then be selected in MS/MS/MS for further fragmentation to release mass marker groups

EXAMPLE 2

MS/MS and MS/MS/MS Analysis of Mixtures of Labelled Isobaric Peptides

To demonstrate the principle of the invention including the generation of mass reporter groups from mass labels during MS/MS and MS/MS/MS and how MS/MS/MS using isobaric mass labels allows accurate quantification of analytes in a complex mixture, the following peptide solutions were prepared:

TABLE 2

| | | | SIXPLEX | | | | | |
|---|---|---|---|---|---|---|---|---|
| pep | SEQ ID NO: | seq | 126 | 127 | 128 | 129 | 130 | 131 |
| 1 | 2 | VAFSLR | 1 | 3 | 5 | 5 | 3 | 1 |
| 2 | 3 | AVFSLR | 1 | 1 | 1 | 4 | 4 | 4 |
| 3 | 4 | FAVSLR | 4 | 4 | 4 | 1 | 1 | 1 |
| 6 | 5 | LAFSVR | 5 | 3 | 1 | 1 | 3 | 5 |

Separate samples of each peptide 1, 2, 3 and 6 were prepared and each divided into six aliquots. Each aliquot comprised a predetermined amount of the peptide and the relative ratio of the peptide in each aliquot is shown in the table above. For example, peptide 1 was split into six aliquots having a relative ratio of peptide of 1:3:5:5:3:1. Each of the six aliquots for each peptide was labelled with a different TMTsixplex mass label. The structures of the mass labels used to the label the peptide aliquots are shown below: TMT⁶-126 (I), TMT⁶-127 (II), TMT⁶-128 (III), TMT⁶-129 (IV), TMT⁶-130 (V) and TMT⁶-131 (VI).

Each peptide is attached to a mass label at the N-terminus and at each lysine residue.

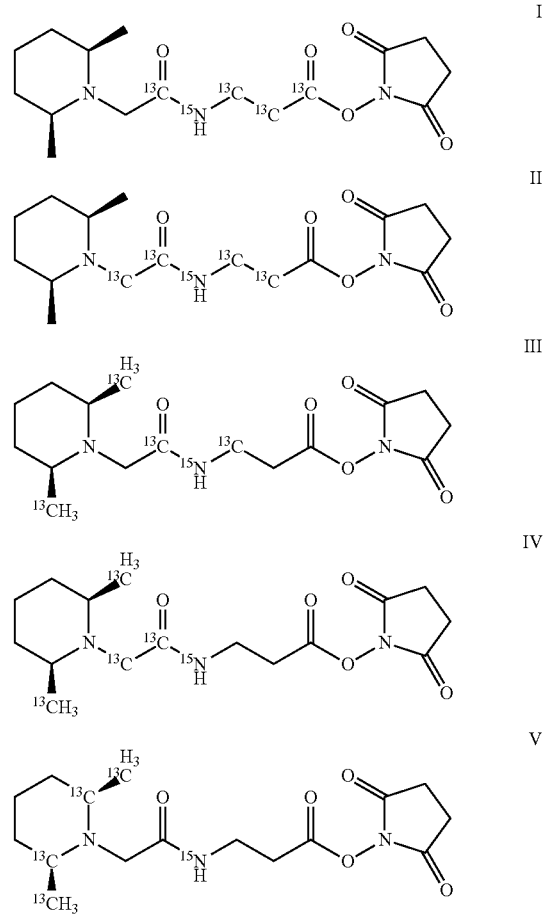

-continued

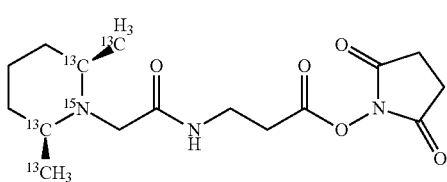

VI

The six aliquots of peptide 1 were then mixed together (hereinafter referred to as peptide 1 mixture) and analysed firstly by MS, then by MS/MS and then the b1-ion was selected for MS/MS/MS. This was repeated for each individual peptide mixture. The MS, MS/MS and MS/MS/MS spectra for each peptide mixture is discussed below:

Peptide 1

Figure 3:
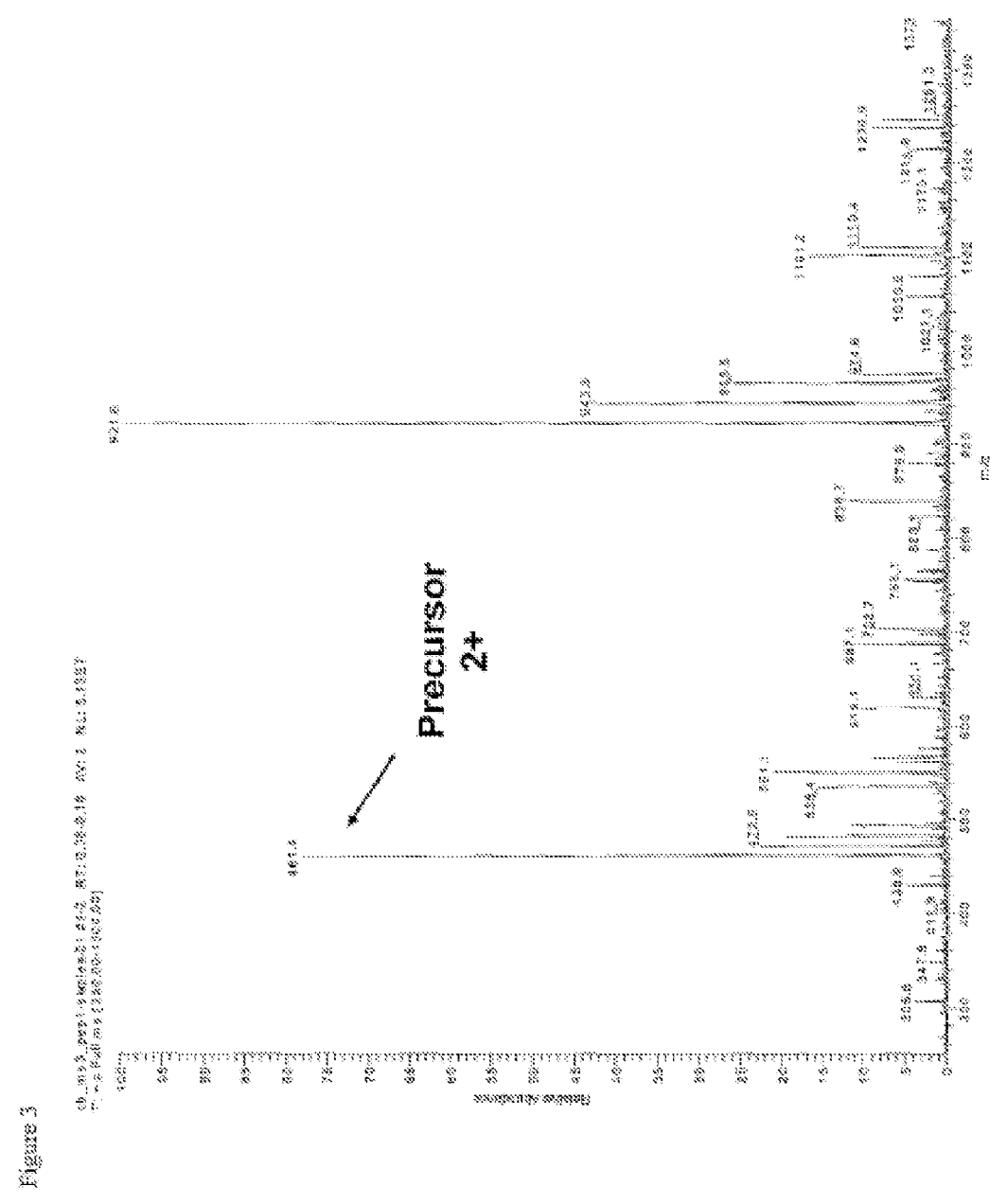

FIG. 3 shows a MS spectrum of peptide 1 mixture, wherein the precursor 2+ ion at m/z 461 and the precursor 1+ ion at m/z 921 is peptide 1 attached to a mass label. The peaks at m/z 461 and m/z 921 show the peptide in two different charge states.

FIG. 4 shows a MS/MS spectrum of peptide 1 mixture, wherein the b1-ion at m/z 329 is TMT$^6$-130 (V) attached to an intact mass label.

FIG. 5a shows a zoom of the MS/MS spectrum of FIG. 4 showing the peaks of the six different mass marker groups. The correct ratio of 1:3:5:5:3:1 is shown by the peak heights.

FIG. 5b shows a zoom of the MS/MS/MS spectrum after selection of the b-1 ion attached to an intact mass label and further fragmentation. The correct ratio of 1:3:5:5:3:1 is also shown by the peak heights for the mass marker groups in MS/MS/MS.

Peptide 2

Figure 6:
FIG. 6 shows a MS spectrum of peptide AVFSLR (SEQ ID NO: 3) labelled with different isobaric mass labels from a set of six mass labels, each label representing a predetermined relative amount of the peptide (the ratio the mass marker groups having masses of 126:127:128:129:130:131 is 1:1:1:4:4:4).

FIG. 6 shows a MS spectrum of peptide 2 mixture, wherein the precursor 2+ ion at m/z 461 and the precursor 1+ ion at m/z 921 is peptide 2 attached to a mass label.

FIG. 7 shows a MS/MS spectrum of peptide 2 mixture, wherein the b1-ion at m/z 301 is A attached to an intact mass label.

FIG. 8a shows a zoom of the MS/MS spectrum of FIG. 7 showing the peaks of the six different mass marker groups. The correct ratio of 1:1:1:4:4:4 is shown by the peak heights.

FIG. 8b shows a zoom of the MS/MS/MS spectrum after selection of the b-1 ion attached to an intact mass label and further fragmentation: The correct ratio of 1:1:1:4:4:4 is also shown by the peak heights for the mass marker groups in MS/MS/MS.

Peptide 3

FIG. 9 shows a MS spectrum of peptide 3 mixture, wherein the precursor 2+ ion at m/z 461 and the precursor 1+ ion at m/z 921 is peptide 3 attached to a mass label.

Figure 10:
FIG. 10 shows a MS/MS spectrum of the labelled FAVSLR peptide (SEQ ID NO: 4), as analysed in FIG. 9.

FIG. 10 shows a MS/MS spectrum of peptide 3 mixture, wherein the b1-ion at m/z 377 is F attached to an intact mass label.

FIG. 11a shows a zoom of the MS/MS spectrum of FIG. 10 showing the peaks of the six different mass marker groups. The correct ratio of 4:4:4:1:1:1 is shown by the peak heights.

FIG. 11b shows a zoom of the MS/MS/MS spectrum after selection of the b-1 ion attached to an intact mass label and further fragmentation. The correct ratio of 4:4:4:1:1:1 is also shown by the peak heights for the mass marker groups in MS/MS/MS.

Peptide 6

FIG. 12 shows a MS spectrum of peptide 6 mixture, wherein the precursor 2+ ion at m/z 461 and the precursor 1+ ion at m/z 921 is peptide 3 attached to a mass label.

Figure 13:
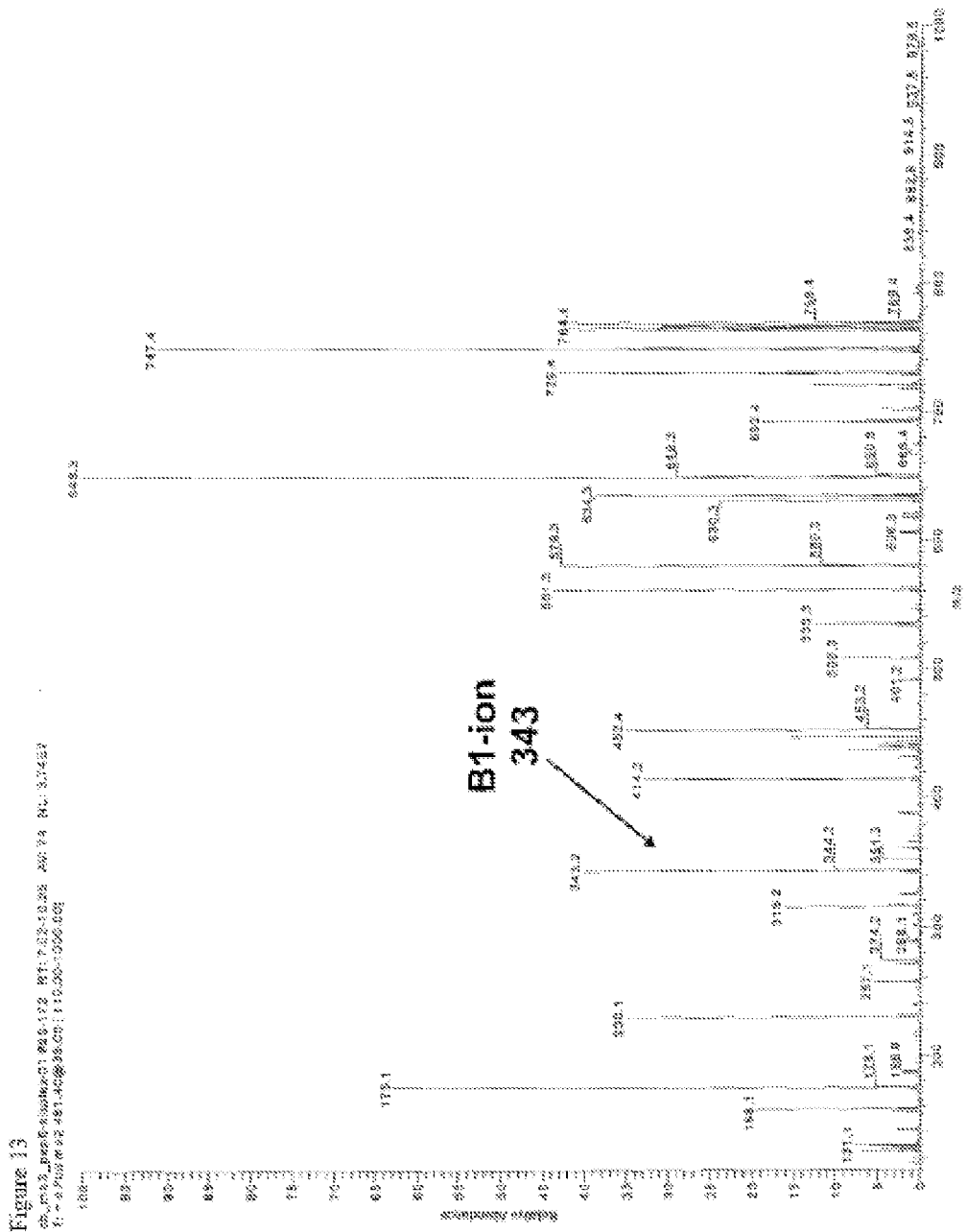
FIG. 13 shows a MS/MS spectrum of the labelled LAFSVR peptide (SEQ ID NO: 5), as analysed in FIG. 12.

FIG. 13 shows a MS/MS spectrum of peptide 6 mixture, wherein the b1-ion at m/z 343 is L attached to an intact mass label.

FIG. 14a shows a zoom of the MS/MS spectrum of FIG. 13 showing the peaks of the six different mass marker groups. The correct ratio of 5:3:1:1:3:5 is shown by the peak heights.

FIG. 14b shows a zoom of the MS/MS/MS spectrum after selection of the b-1 ion attached to an intact mass label and further fragmentation. The correct ratio of 5:3:1:1:3:5 is also shown by the peak heights for the mass marker groups in MS/MS/MS.

The above analysis by MS, MS/MS and MS/MS/MS of peptide mixtures 1, 2, 3 and 6 shows that in MS common precursor ions are shown because both the peptides themselves and the mass labels are all isobaric. In MS/MS, different b1-ion fragments are produced after one fragmentation step, wherein the b1-ions are attached to an intact mass label. Each peptide produces a different b1-ion. In MS/MS/MS, selection of the mass to charge ratio of the b1-ion attached to an intact mass label followed by fragmentation generates peaks corresponding to the mass marker groups, wherein the peaks of the six different mass marker groups correspond to the correct ratio of the labelled peptide mixture shown in Table 2 above.

MS, MS/MS and MS/MS/MS was then carried out on the following peptide mixtures:

Peptide 1 and Peptide 6

The six aliquot mixture of peptide 1 was mixed with the six aliquot mixture of peptide 6 and analysed as above.

FIG. 15 shows the MS spectrum of the peptide 1 and peptide 6 mixture, wherein both peptides have the same precursor 2+ ion at m/z 461 and the precursor 1+ ion at m/z 921 represents each peptide attached to a mass label.

FIG. 16 shows a MS/MS spectrum of the peptide 1 and peptide 6 mixture, wherein the b1-ion at m/z 329 is from peptide 1 and the b1-ion at m/z 343 is from peptide 6.

FIG. 17 shows a zoom of the MS/MS spectrum of FIG. 16 showing the peaks of the six different mass marker groups from both peptide 1 and peptide 6. The height of the six peaks for each mass marker group does not correspond to the correct ratio for either peptide 1 or peptide 6. This is because in MS/MS both isobaric peptides were selected and, therefore, mass reporter groups are from both labelled peptides.

Figure 18A:
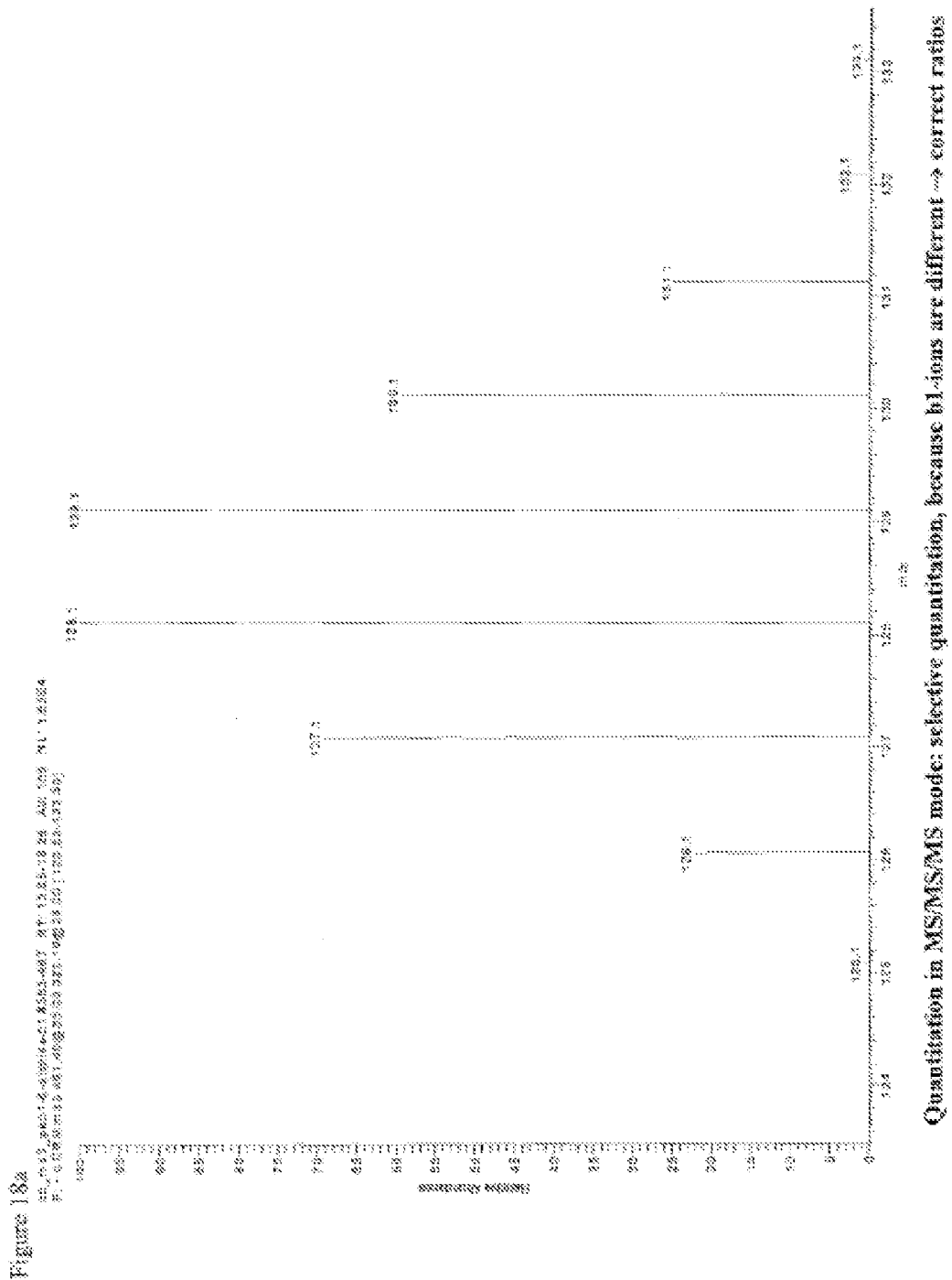
FIG. 18a shows a MS/MS/MS spectrum of the distinct mass marker groups from the b1-ions of labelled VAFSLR (SEQ ID NO: 2), as analysed in FIG. 15.

FIG. 18a shows a zoom of the MS/MS/MS spectrum after selection of the b-1 ion for peptide 1 and further fragmentation. The correct ratio of 1:3:5:5:3:1 is shown by the peak heights for the mass marker groups because only peptide 1 has a b1-ion of mass 329 and therefore the mass marker groups are only from peptide 1.

FIG. 18b shows a zoom of the MS/MS/MS spectrum after selection of the b-1 ion for peptide 6 and further fragmentation. The correct ratio of 5:3:1:1:3:5 is shown by the peak heights for the mass marker groups because only peptide 6 has a b1-ion of mass 343 and therefore the mass marker groups are only from peptide 6.

Peptide 2 and Peptide 3

The six aliquot mixture of peptide 2 was mixed with the six aliquot mixture of peptide 3 and analysed as above.

FIG. 19 shows the MS spectrum of peptide 2 and peptide 3 mixture, wherein both peptides have the same precursor 2+ ion at m/z 461 and the precursor 1+ ion at m/z 921 represents each peptide attached to a mass label.

FIG. 20 shows a MS/MS spectrum of peptide 2 and peptide 3 mixture, wherein the b1-ion at m/z 301 is from peptide 2 and the b1-ion at m/z 377 is from peptide 3.

FIG. 21 shows a zoom of the MS/MS spectrum of FIG. 20 showing the peaks of the six different mass marker groups from both peptide 2 and peptide 3. The height of the six peaks for each mass marker group does not correspond to the correct ratio for either peptide 2 or peptide 3. This is because in MS/MS both isobaric peptides were selected and, therefore, mass reporter groups are from both labelled peptides.

FIG. 22a shows a zoom of the MS/MS/MS spectrum after selection of the b-1 ion for peptide 2 and further fragmentation. The correct ratio of 1:1:1:4:4:4 is shown by the peak heights for the mass marker groups because only peptide 2 has a b1-ion of mass 301 and therefore the mass marker groups are only from peptide 2.

FIG. 22b shows a zoom of the MS/MS/MS spectrum after selection of the b-1 ion for peptide 3 and further fragmentation. The correct ratio of 4:4:4:1:1:1 is shown by the peak heights for the mass marker groups because only peptide 3 has a b1-ion of mass 377 and therefore the mass marker groups are only from peptide 3.

The above analysis by MS, MS/MS and MS/MS/MS of peptide mixture 1 and 6 and peptide mixture 2 and 3 shows that quantitation by MS/MS is inaccurate when a complex mixture of peptide is analysed comprising isobaric peptides. However, this problem is overcome by selection of the b1-ion for one peptide, wherein the b1-ion comprises an intact mass label, and subjecting the b1-ion to fragmentation to release the mass marker groups. The peaks heights of the mass marker groups after MS/MS/MS show the correct ratio of each label representing each aliquot of the peptide. The step of selection of b1-ion and fragmentation can then be repeated for each peptide in the mixture.

EXAMPLE 3

MS/MS Analysis of 8Abeled Peptide AEFAEVSK (SEQ ID NO: 6)

Figure 23:
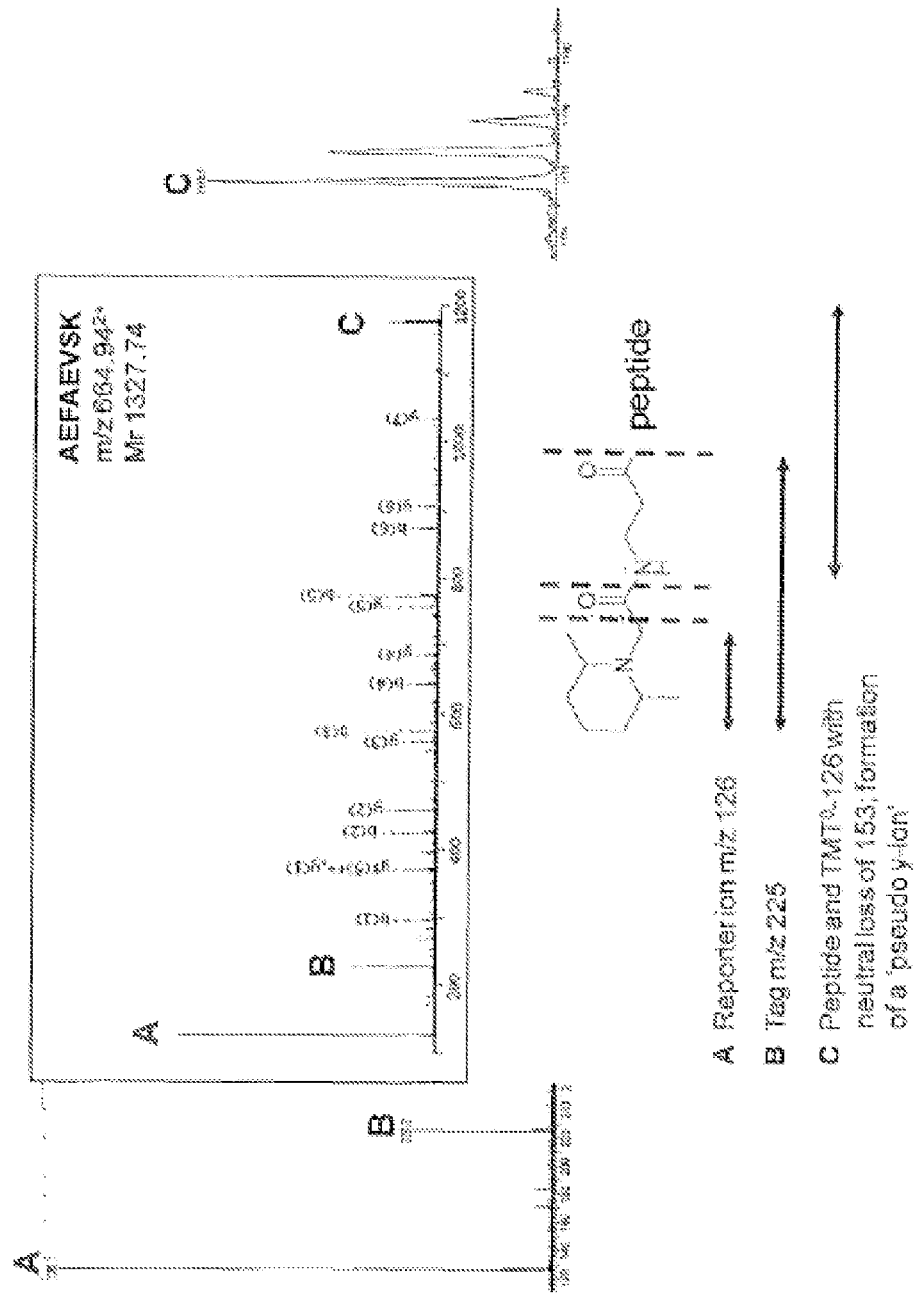
FIG. 23 shows a MS/MS spectrum of labelled peptide AEFAEVSK (SEQ ID NO: 6) and the structure of the mass label (TMT zero) used to label the peptide. The peptide is labelled at the N-terminus and at the lysine. Ions arising from fragmentation of the mass label are shown.

Peptide AEFAEVSK (SEQ ID NO: 6) was labelled with mass label. TMTzero, (the structure of this label is shown in FIG. 23), and analysed by MS/MS. The peptide is labelled with two labels, one at the N-terminus and one at the C-terminal lysine. FIG. 23 shows the full MS/MS spectrum of the labelled peptide. The peak labelled A (126) represents the m/z of the mass marker group. The peak labelled B (225) represents the m/z of the whole mass label. The peak labelled C (1175.7 and charge state 1), is a pseudo-y-ion which represents the m/z of the peptide and a portion of the mass label, a charge loss of 1 and a mass loss of 153 Da, resulting from the loss of one mass marker group and the neighbouring carbonyl group. Generally, this loss may have occurred on the aminoterminal tag as well as on the lysine tag. Since the peptide has one mass label on the N-terminus and one mass label on the C-terminal lysine, one intact mass label is still present on the pseudo y-ion after MS/MS.

EXAMPLE 4

MS/MS Analysis of Labelled Peptide VLEPTLK (SEQ ID NO: 7)

Figure 24:
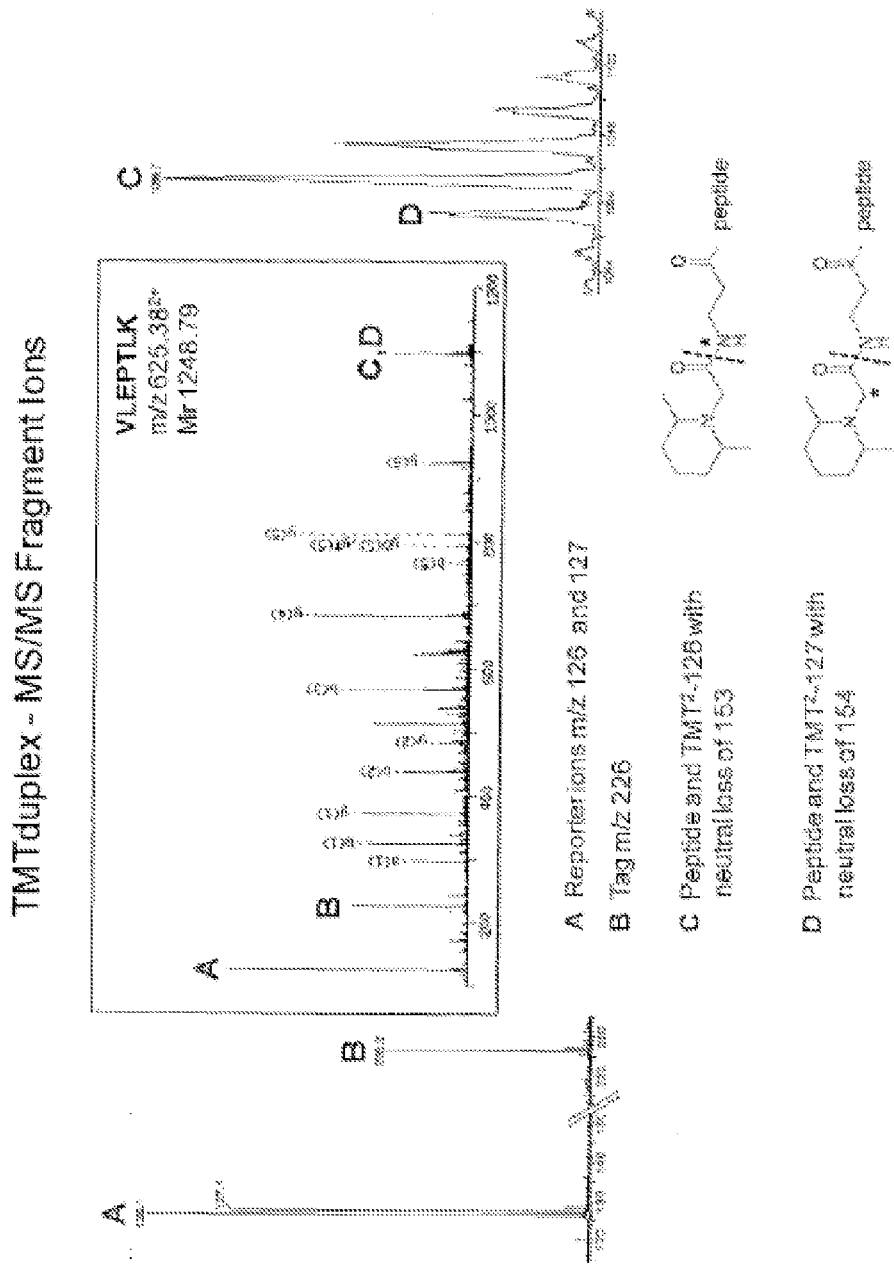
FIG. 24 shows a MS/MS spectrum of peptide VLEPTLK (SEQ ID NO: 7) labelled with a set of two isobaric mass labels (TMT duplex comprises $TMT^2$-126 and $TMT^2$-127), and the structures of the mass labels used to label the peptide. The peptide is labelled at the N-terminus and at the lysine. Ions arising from fragmentation of the mass labels are shown.

Peptide VLEPTLK (SEQ ID NO: 7) was labelled with TMTduplex, (TMT$^2$-126 and TMT$^2$-127, as shown in FIG. 24), and analysed by MS/MS. The peptide is labelled with two labels, one at the N-terminus and one at the C-terminal lysine. FIG. 24 shows the full MS/MS spectrum of the labelled peptide. The peaks labelled A (126 and 127) represents the m/z of the mass marker groups. The peak labelled B (226) represents the m/z of the whole mass label. The peak labelled C (1096.7) and the peak labelled D (1095.7) represent the pseudo-y-ions for each different labelled peptide, as shown in FIG. 24, by loss of 153 Da (TMT$^2$-126) and loss of 154 Da (TMT$^2$-127). Generally, this loss may have occurred on the aminoterminal tag as well as on the lysine tag. Since the peptide has one mass label on the N-terminus and one mass label on the C-terminal lysine, one intact mass label is still present on the peptide after MS/MS.

EXAMPLE 5

MS/MS Analysis of Labelled Peptide LVNEVTEFAK (SEQ ID NO: 8)

Peptide LVNEVTEFAK (SEQ ID NO: 8) was labelled with two mass labels. One aliquot was labelled with TMTzero (mass reporter group of 126 Da and structure shown in FIG. 23) and one aliquot was labelled with TMTsixplex (TMT$^6$-131). In each aliquot, the peptide is labelled with two labels, one at the N-terminus and one at the C-terminal lysine.

Figures 25A, 25B:
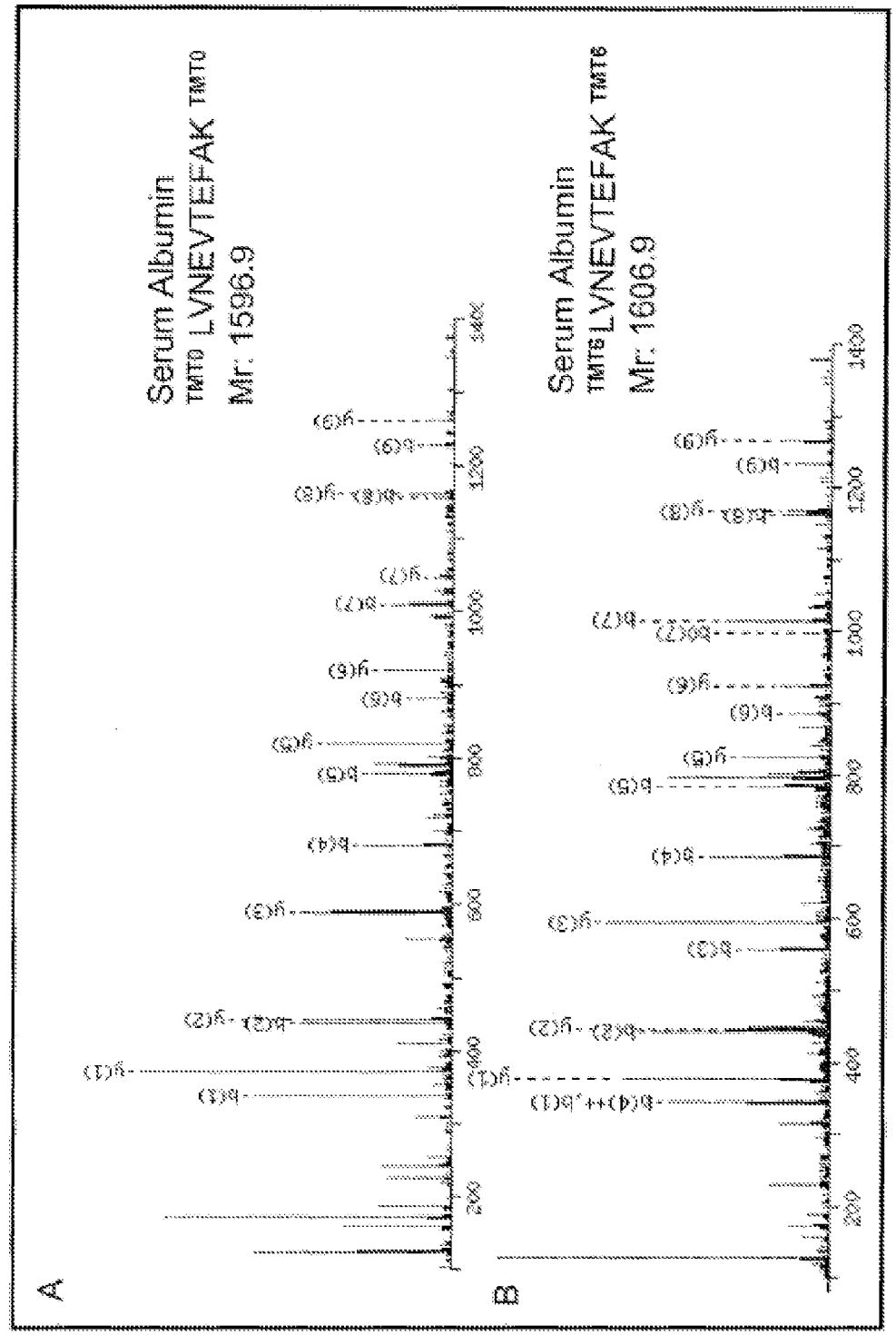
FIG. 25a shows a MS/MS spectrum of a peptide from Serum Albumin LVNEVTEFAK (SEQ ID NO: 8) labelled with mass label TMT-zero
FIG. 25b shows a MS/MS spectrum of a peptide from Serum Albumin LVNEVTEFAK (SEQ ID NO: 8) labelled with mass label TMT sixplex. The peptide in FIGS. 25a and 25b is labelled at the N-terminus and the lysine. A mass difference of 10 Da is shown between the labelled peptides in FIGS. 25a and 25b.

FIG. 25a shows the MS/MS spectrum of the peptide labelled with TMTzero and FIG. 25b shows the MS/MS spectrum of the peptide labelled with TMTsixplex (TMT$^6$-131). There is a mass difference of 10 Th due to the attachment of two mass labels on each peptide.

Figure 26A:
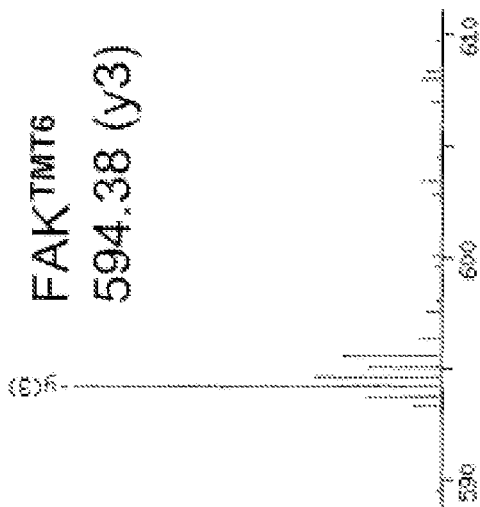
FIG. 26a shows a zoomed in section of the MS/MS spectrum of FIG. 25a showing the y3 ion fragment and FIG. 26b shows a zoomed in section of the MS/MS spectrum of FIG. 25b showing the y3 ion fragment. The y3 ion fragment retains one intact mass label on the lysine residue giving a m/z difference of 5 Thomsons (Th, unit of mass to charge ratio) between the two labelled fragment ions in FIGS. 26a and 26b.
Figure 26B:
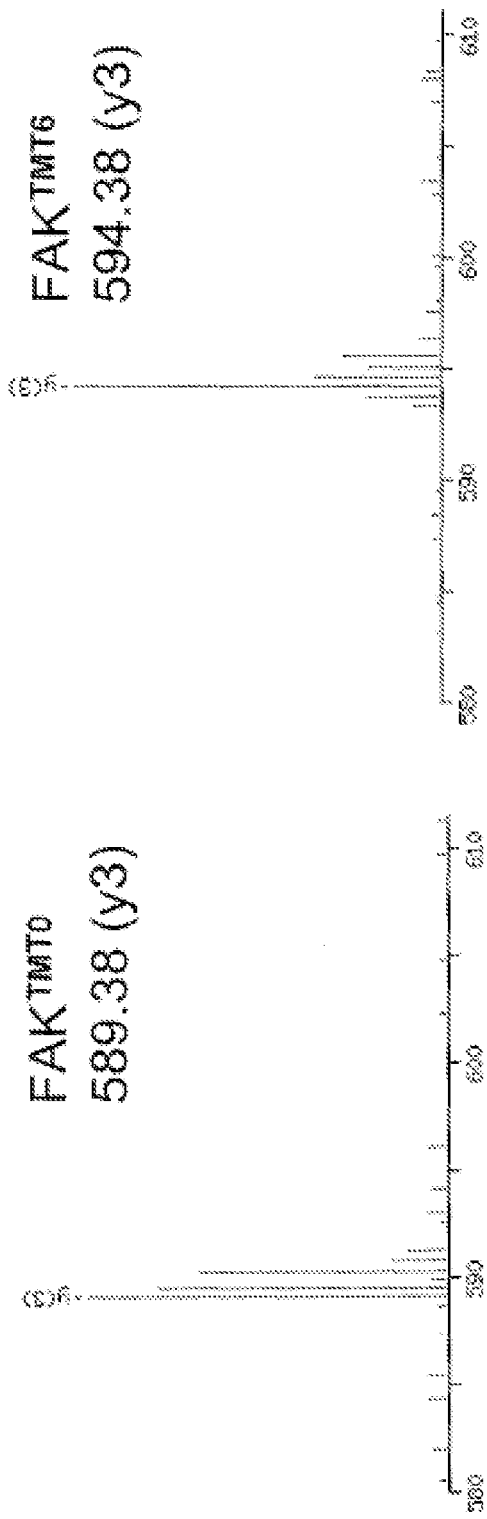

FIG. 26a shows a zoom of the y3-ion from FIG. 25a and FIG. 26b shows a zoom of the y3-ion from FIG. 25b. Each y3-ion comprises one intact mass label, as shown by the 5 Th difference between y3-ionsin FIG. 26a and FIG. 26b.

Figures 27A, 27B:
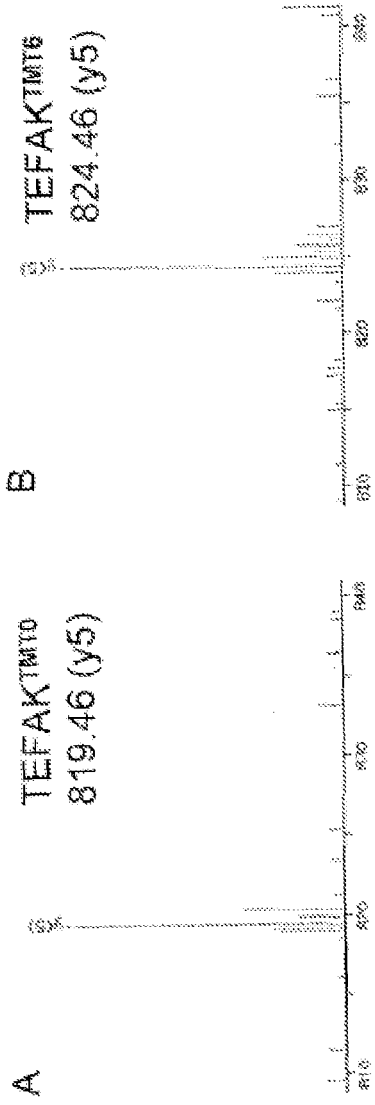
FIG. 27a shows a zoomed in section of the MS/MS spectrum of FIG. 25a showing the y5 ion fragment and FIG. 27b shows a zoomed in section of the MS/MS spectrum of FIG. 25b showing the y3 ion fragment. The y5 fragment ion retains one intact mass label on the lysine residue giving a m/z difference of 5 Thomsons (Th unit of mass to charge ratio) between the two labelled fragment ions in FIGS. 27a and 27b.

FIG. 27a shows a zoom of the y5-ion from FIG. 25a and FIG. 27b shows a zoom of the y5-ion from FIG. 25b. Each y5-ion comprises one intact mass label, as shown by the 5 Th difference between the y5-ion in FIG. 27a and the y5-ion in FIG. 27b.

Figures 28A, 28B:
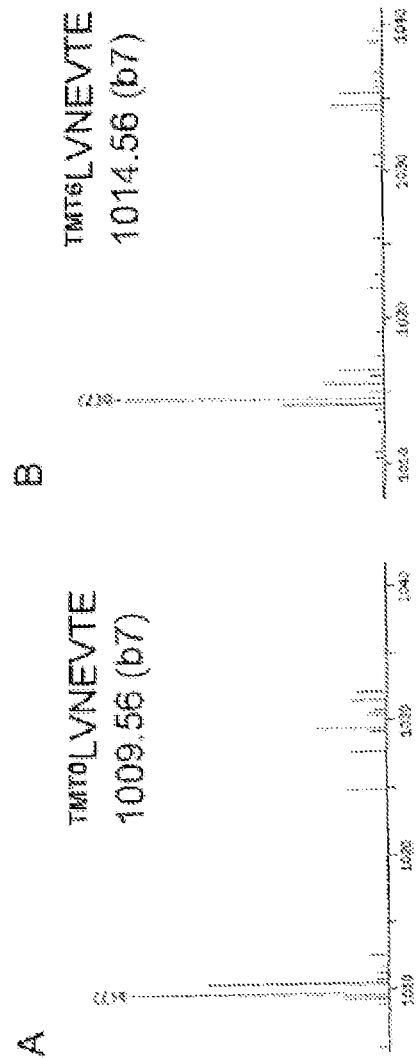
FIG. 28a shows a zoomed in section of the MS/MS spectrum of FIG. 25a showing the b7 ion fragment and FIG. 28b shows a zoomed in section of the MS/MS spectrum of FIG. 25b showing the b7 ion fragment. The b7 fragment ion retains one intact mass label on the N-terminus giving a m/z difference of 5 Thomsons (Th unit of mass to charge ratio) between the two labelled fragment ions in FIGS. 28a and 28b.

FIG. 28a shows a zoom of the b7-ion from FIG. 25a and FIG. 28b shows a zoom of the b7-ion from FIG. 25b. Each b7-ion comprises one intact mass label, as shown by the 5 Th difference between the b7-ion in FIG. 28a and the b7-ion in FIG. 28b.

FIGS. 26 to 28 show that after MS/MS a number of different fragment ions of the peptide still comprise one intact mass label and, therefore, any of these ions may be selected in MS/MS/MS and will fragment to provide mass reporter groups suitable for accurate quantification of the peptide.

EXAMPLE 6

MS/MS Analysis of Labelled Peptide LVTDLTK (SEQ ID NO: 9)

Peptide LVTDLTK (SEQ ID NO: 9) was labelled with two mass labels. One aliquot of the peptide was labelled with mass label TMTzero (total mass 224 Da) and one aliquot was labelled with TMTsixplex(TMT6-128; total mass 229 Da). The TMTzero and TMT6-128 labelled peptides have two mass labels attached, one at the N-terminus and one at the lysine giving a mass difference of 10 Da between the two labelled peptides.

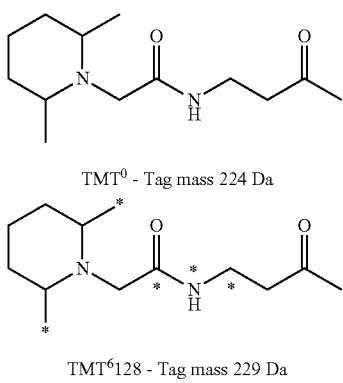

TMT⁰ - Tag mass 224 Da

TMT⁶128 - Tag mass 229 Da

Figure 29A:
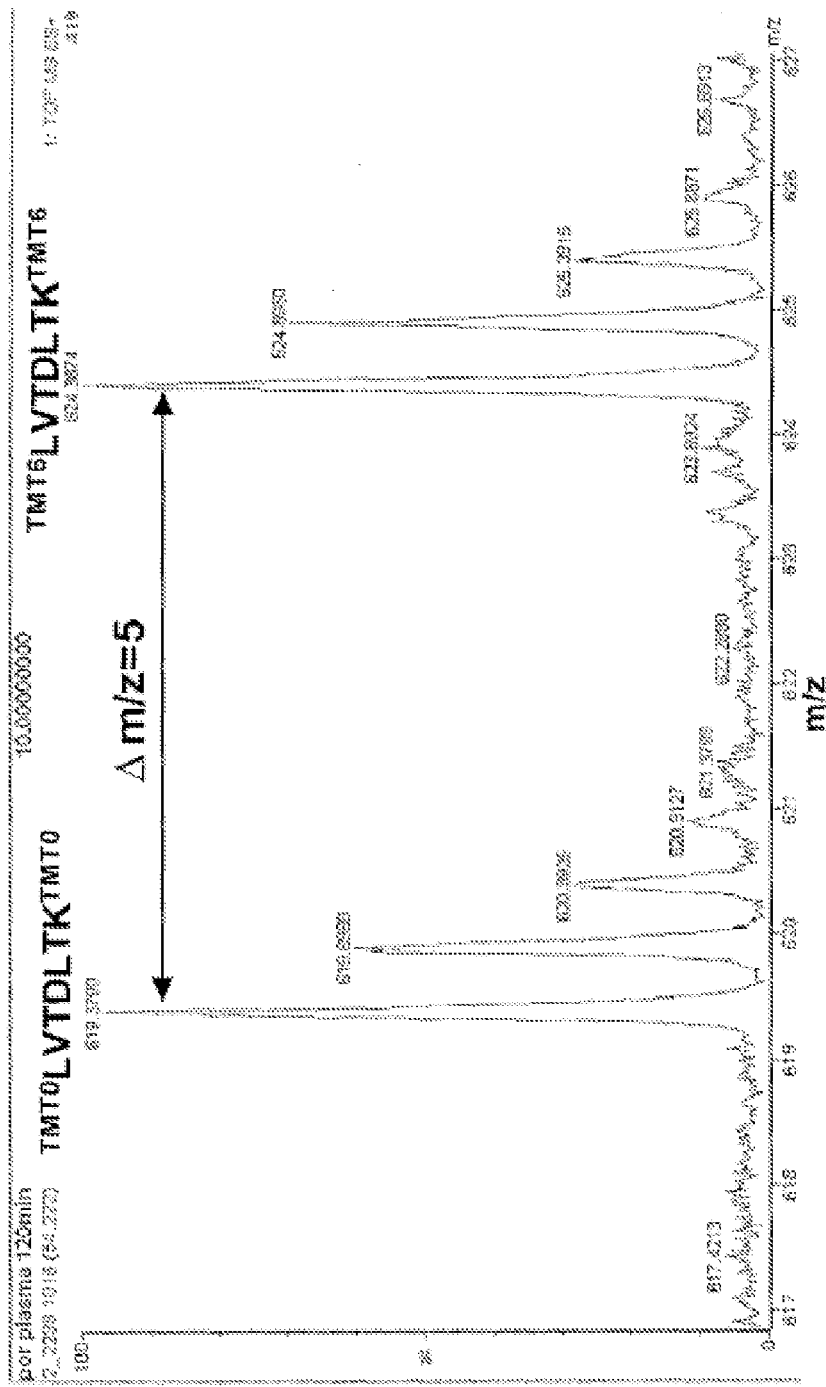
FIG. 29a shows a MS spectrum of peptide LVTDLTK (SEQ ID NO: 9) labelled with TMT zero and TMTsixplex. The peptide is labelled at the N-tenninus and lysine giving a mass difference of 10 Da between the labelled peptides TMT zero and TMT sixplex. A mass difference of 5 Th is observed between the doubly charged precursor ions.

The differently labelled aliquots were then mixed together and analysed by MS. FIG. 29*a* shows a mass spectrum of the doubly charged precursor ions at m/z 619.4 (TMTzero labelled peptide) and m/z 624.4 (TMT⁶-128 labelled peptide). A mass difference of 10 Da between the two tagged peptides gives a difference in m/z of 5 Th between the doubly charged precursors.

EXAMPLE 7

MS/MS Analysis of Labelled Peptide HPDYSVVLLLR (SEQ ID NO: 10)

Peptide HPDYSVVLLLR (SEQ ID NO: 10) was labelled with two mass labels TMTzero and TMT⁶-128, as described in example 6. The TMTzero and TMT⁶-128 labelled peptides have one tag attached at the N-terminus, giving a mass difference of 5 Da between the two tagged peptides.

Figure 29B:
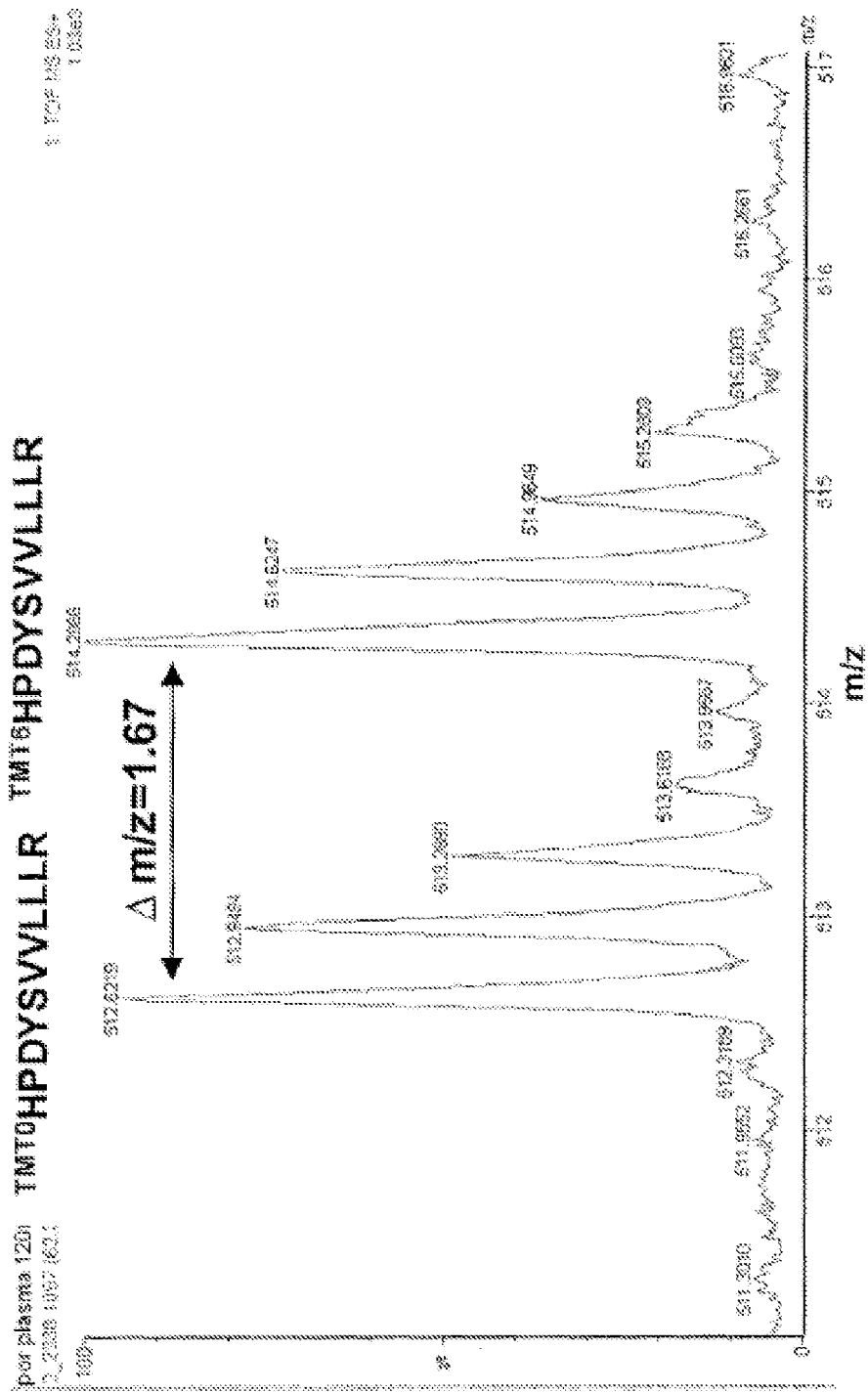
FIG. 29b shows a MS spectrum of peptide HPDYSVV-LLLR (SEQ ID NO: 10) labelled with TMTzero and TMTsixplex. The peptide is labelled at the N-terminus giving a mass difference of 5 Da between the labelled peptides TMT zero and TMT sixplex. A mass difference of 1.67 Th is observed between the triply charged precursor ions.

FIG. 29 *b* shows the MS spectrum of the triply charged precursor ions at m/z 512.62 (TMTzero labelled peptide) and m/z 514.30 (TMT⁶-128 labelled peptide). A mass difference of 5 Da between the two tagged peptides gives a difference in m/z of 1.66 Th between the triply charged precursors.

EXAMPLE 8

Analysis of Labelled Plasma Peptides by Chromatography and MRM

Plasma peptides A to M, as shown in table 3 below, were labelled with mass labels TMTzero and TMT⁶-127. The labelled peptide samples were mixed in a 1:1 ratio and, in the first instance, analysed by independent data acquisition (ida) on a 4000 QTRAP to obtain MS/MS fragment ion information. This was to determine the optimal Q1 (precursor ion selected in step c) of the method according to the present invention) and Q3 (MS/MS fragment ion selected in step e) transitions for TMTzero and TMT⁶-127 labelled versions of the selected peptides for subsequent analysis in steps f) to h) (MS/MS/MS). The collision energy to fragment the peptide for the optimal detection of the Q3 transition was also determined.

Prior to analysis by mass spectrometry the labelled peptide sample is resolved by reversed-phase chromatography interfaced to the mass spectrometer. The chromatographic properties (retention time) were defined from the ida analysis.

Table 3 lists the different Q1 and Q3 transitions for a set of TMTzero and TMT⁶-127 labelled peptides, the charge state of labelled precursor ions and the retention time for each peptide are also given. Q1 and Q3 transitions vary between the TMTzero and TMT⁶-127 labelled versions of the peptide; this is dependent on the number of tags attached to the precursor ion and its charge state (Q1 transition), and the number of tags attached to the fragment ion (Q3 transition). In all cases the Q3 transitions were singly charged. The information listed in Table 3 was required for the detection of the selected peptides by the method according to the present invention.

Figure 30:
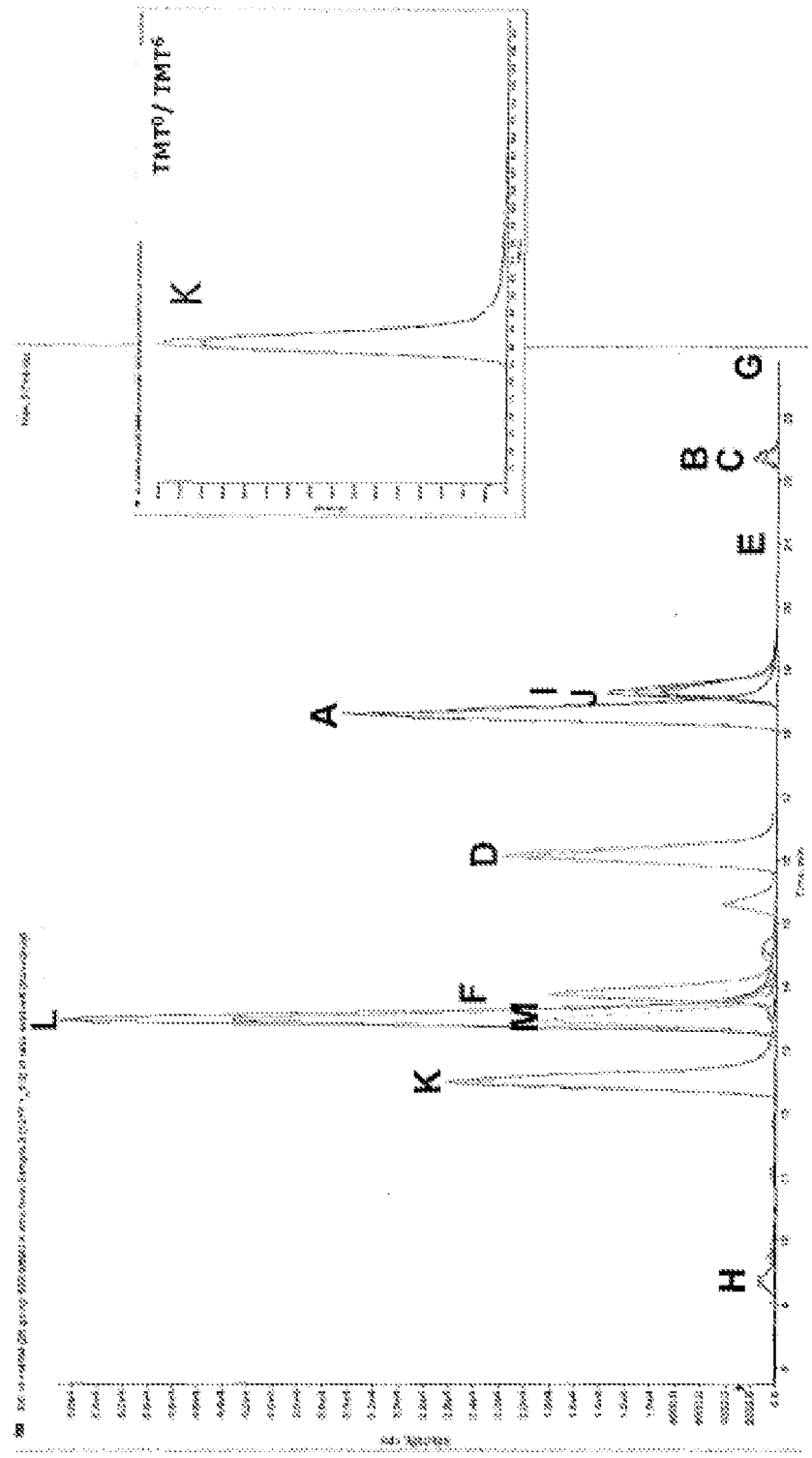
FIG. 30 shows an MRM ion chromatogram of ten plasma peptides labelled with mass label TMT-zero and mass label TMTsixplex ($TMT^6$-127).
Figure 31:
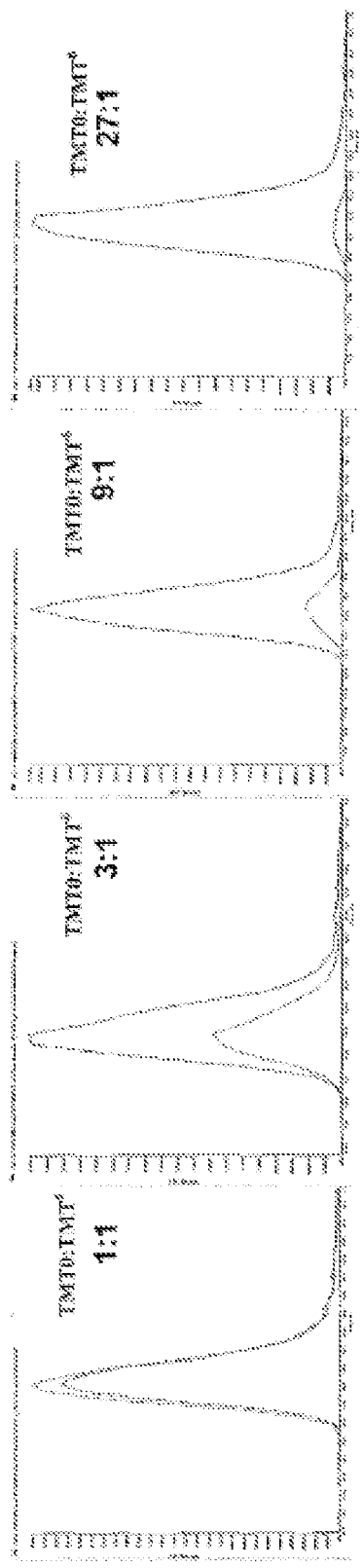
FIGS. 31a to d show MRM ion chromatograms of a plasma peptide K labelled with TMT-zero and TMTsixplex ($TMT^6$-127). The TMT-labelled plasma samples have been mixed in different ratios.

FIG. 30 shows the MRM ion chromatogram for the TMTzero and TMT⁶-127 labelled peptides of Table 3, wherein the labelled peptides were run over a 30 minute gradient with 1 μg protein load o/c (500 ng of each aliquot of labelled peptide). It can be seen from FIG. 30 that the labelled peptides, mixed in a 1:1 ratio, co-elute.

TABLE 3

| | Protein | SEQ ID NO: | Peptide sequence | Charge state | Retention Time (mins) | CE | Q1 TMTzero | Q3 TMTzero | Q1 TMT⁶-127 | Q3 TMT⁶-127 |
|---|---|---|---|---|---|---|---|---|---|---|
| A | Albumin | 9 | $^{TMT}$LVTDLTK$^{TMT}$ | 2 | 31.9 | 34 | 619.38 | 585.40 (y3) | 624.38 | 590.40 (y3) |
| B | Albumin | 8 | $^{TMT}$LVNEVTEFAK$^{TMT}$ | 2 | 35.3 | 43 | 799.48 | 819.46 (y5) | 804.48 | 824.46 (y5) |
| C | Albumin | 8 | $^{TMT}$LVNEVTEFAK$^{TMT}$ | 2 | 35.3 | 43 | 799.48 | 589.38 (y3) | 804.48 | 594.38 (y3) |
| D | IgG | 12 | $^{TMT}$ALPAPIEK$^{TMT}$ | 2 | 29.3 | 35 | 643.90 | 878.55 (y6) | 648.90 | 883.55 (y6) |
| E | Serotransferin | 13 | $^{TMT}$SASDLWDNLK$^{TMT}$ | 2 | 34.1 | 46 | 849.47 | 598.40 (y3) | 854.47 | 603.40 (y3) |
| F | Haptoglobulin | 14 | $^{TMT}$ILGGHLDAK$^{TMT}$ | 3 | 10.5 | 32 | 457.94 | 670.42 (y4) | 461.31 | 675.42 (y4) |
| G | Complement C3 | 15 | $^{TMT}$SLSVPYVIVPLK$^{TMT}$ | 2 | 20.7 | 60 | 925.55 | 581.41 (y3) | 930.55 | 586.41 (y3) |
| H | α2 Macroglobulin | 16 | $^{TMT}$LVHVEEPHTETVR | 3 | 6.8 | 38 | 590.66 | 839.44 (y7) | 592.33 | 839.44 (y7) |
| I | Albumin | 17 | $^{TMT}$FQNALLR | 2 | 13.9 | 43 | 592.90 | 1031.76 (pseudo y) | 595.90 | 1034.7 (pseudo y) |
| J | Albumin | 17 | $^{TMT}$FQNALLR | 2 | 13.9 | 43 | 592.90 | 798.50 (b5) | 595.40 | 803.50 (b5) |
| K | IgG | 18 | $^{TMT}$LTVDKTMT | 2 | 9.0 | 29 | 512.29 | 653.39 (b4) | 517.29 | 658.39 (b4) |
| L | IgG | 19 | $^{TMT}$DTLMISR | 2 | 10.0 | 40 | 530.30 | 906.60 (pseudo y) | 532.80 | 909.30 (pseudo y) |
| M | IgG | 19 | $^{TMT}$DTLMISR | 2 | 10.0 | 40 | 530.30 | 685.40 (b4) | 532.80 | 690.40 (b4) |

EXAMPLE 9

To demonstrate the accuracy and reproducibility of quantitation using TMTzero and TMTsixplex (TMT$^6$-127) labelled peptides combined with MRM, TMTzero and TMT$^6$-127 labelled plasma peptides were mixed in different ratios and the MRM transitions for the labelled peptide transitions A-M (Table 3) assessed. TMTzero:TMT$^6$-127 labelled samples were combined in 1:1, 3:1, 9:1 and 27:1 ratios; each ratio was analysed in triplicate. FIGS. 31a to d show the MRM ion chromatograms for a selected peptide K over the different ratios measured.

Ratios were compared for all peptide transitions A-M (Table 3) by extracting peak areas for each TMTzero and TMT$^6$-127 MRM transition using BioAnalyst® automated peak integration tool. Table 4 shows the observed mean ratios (average of three measurements) for all selected peptides and the coefficient of variance for each. The peptides are listed in order of retention time on the reversed phase column (1-13 numbered in parentheses). It can be seen that the observed mean ratios correlate very well with the expected ratios. Additionally, 82% of the observed ratios have coefficients of variation less than 5% (triplicate measurements). Observed ratios which showed the greatest deviations from the expected ratios and had higher coefficients of variation could be explained as these measurements were from the more hydrophobic peptides (highest retention times). For these peptides a deterioration in peak shape is observed due to the stronger binding of these peptides to the reversed phase resin and the higher concentrations of acetonitrile, the eluting solvent, required for their elution causing instability of the electrospray. Therefore peptides with earlier retention times are optimal for the approach.

Figure 32:
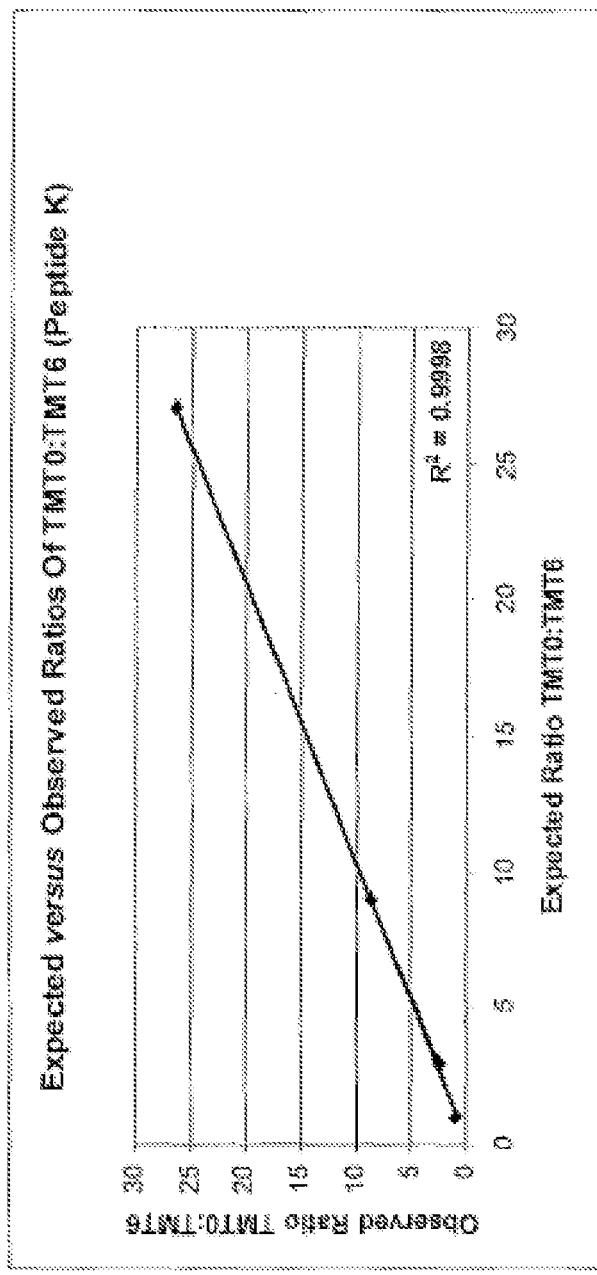
FIG. 32 shows a graph of the expected ratios versus the observed ratios of TMTzero:TMTsixplex for peptide K (as shown in FIGS. 31a to 31d). The analysis was performed in triplicate.

Shown in FIG. 32, taking peptide K as an example, observed ratios correlated very well with observed ratios. A linear relationship was shown over peak areas ranging from $2 \times 10e^4$ to $8 \times 10e^5$ ($R^2=0.9998$). A low coefficient of variation was also seen across replicate analyses (Table 4).

TABLE 4

| Peptide | Expected Ratio TMTzero:TMT$^6$-127 | Observed Mean Ratio TMTzero:TMT$^6$-127 | CV (%) |
|---|---|---|---|
| H (1) | 1:1 | 1.0:1 | 0.81 |
|  | 3:1 | 2.9:1 | 2.16 |
|  | 9:1 | 8.7:1 | 5.90 |
|  | 27:1 | 23.1:1 | 1.53 |

TABLE 4-continued

| Peptide | Expected Ratio TMTzero:TMT$^6$-127 | Observed Mean Ratio TMTzero:TMT$^6$-127 | CV (%) |
|---|---|---|---|
| K (2) | 1:1 | 0.9:1 | 0.72 |
|  | 3:1 | 2.5:1 | 0.24 |
|  | 9:1 | 8.6:1 | 0.56 |
|  | 27:1 | 26.5:1 | 0.85 |
| L (3) | 1:1 | 0.9:1 | 0.71 |
|  | 3:1 | 2.6:1 | 0.86 |
|  | 9:1 | 8.4:1 | 1.47 |
|  | 27:1 | 26.0:1 | 1.67 |
| M (4) | 1:1 | 0.8:1 | 0.60 |
|  | 3:1 | 2.2:1 | 0.93 |
|  | 9:1 | 8.6:1 | 0.56 |
|  | 27:1 | 24.5:1 | 0.85 |
| F (5) | 1:1 | 0.8:1 | 2.85 |
|  | 3:1 | 2.1:1 | 0.68 |
|  | 9:1 | 7.4:1 | 1.52 |
|  | 27:1 | 23.7:1 | 3.88 |
| D (6) | 1:1 | 0.8:1 | 2.01 |
|  | 3:1 | 2.3:1 | 2.18 |
|  | 9:1 | 8.0:1 | 2.56 |
|  | 27:1 | 25.7:1 | 2.16 |
| A (7) | 1:1 | 1.0:1 | 1.32 |
|  | 3:1 | 2.6:1 | 0.42 |
|  | 9:1 | 8.5:1 | 2.90 |
|  | 27:1 | 27.4:1 | 2.49 |
| J (8) | 1:1 | 0.9:1 | 0.58 |
|  | 3:1 | 2.6:1 | 1.11 |
|  | 9:1 | 8.4:1 | 2.50 |
|  | 27:1 | 27.9:1 | 2.69 |
| E (9) | 1:1 | 1.0:1 | 0.81 |
|  | 3:1 | 2.8:1 | 2.16 |
|  | 9:1 | 9.5:1 | 5.90 |
|  | 27:1 | 32.6:1 | 1.53 |
| I (10) | 1:1 | 0.8:1 | 1.32 |
|  | 3:1 | 2.2:1 | 1.87 |
|  | 9:1 | 7.5:1 | 3.34 |
|  | 27:1 | 23.8:1 | 1.51 |
| B (11) | 1:1 | 0.9:1 | 4.23 |
|  | 3:1 | 2.5:1 | 7.19 |
|  | 9:1 | 8.4:1 | 4.98 |
|  | 27:1 | 25.5:1 | 5.33 |
| C (12) | 1:1 | 0.9:1 | 4.19 |
|  | 3:1 | 2.5:1 | 9.05 |
|  | 9:1 | 8.7:1 | 3.04 |
|  | 27:1 | 26.8:1 | 7.20 |
| G (13) | 1:1 | 0.9:1 | 2.34 |
|  | 3:1 | 2.7:1 | 13.19 |
|  | 9:1 | 9.2:1 | 21.94 |
|  | 27:1 | 13.1:1 | 8.06 |

The invention claimed is:

1. A method for assaying for a target analyte, which method comprises:
   (a) providing a plurality of samples, at least one of which comprises the target analyte, wherein each sample is differentially labelled with a mass label or a combination of mass labels, wherein the mass labels are from a set of mass labels, wherein each mass label is an isobaric mass label comprising a mass spectrometrically distinct mass marker group, such that the samples can be distinguished by mass spectrometry;
   (b) mixing the plurality of labelled samples to produce an analysis mixture and introducing the analysis mixture into a mass spectrometer;
   (c) selecting ions having a first mass to charge ratio equivalent to an ion of the target analyte labelled with a specific number of mass labels, wherein a proportion of the selected ions comprises contaminating ions;
   (d) fragmenting ions of the first mass to charge ratio into a plurality of fragment ions, wherein a proportion of the plurality of fragment ions comprises at least one intact mass label and wherein a proportion of the plurality of fragment ions comprises contaminating fragment ions;
   (e) selecting ions having a second mass to charge ratio equivalent to a fragment ion of the target analyte comprising at least one intact mass label, which fragment ion is unique to the target analyte and distinct from fragment ions of the contaminating ions;
   (f) fragmenting ions of the second mass to charge ratio into a plurality of further fragment ions, wherein a proportion of the further fragment ions are ions of the mass marker groups;
   (g) producing a mass spectrum of the further fragment ions produced in step (f); and
   (h) determining from the mass spectrum the quantity of the target analyte in each sample.

2. The method according to claim 1, wherein one sample is a test sample and one sample is a calibration sample, wherein the calibration sample comprises one or more different aliquots of the target analyte, each aliquot having a known quantity of the analyte, wherein the test sample and each aliquot of the calibration sample are differentially labelled.

3. The method according to claim 1, wherein the plurality of samples may comprise a plurality of different target analytes and the method comprises a step of repeating steps (c) to (h) for each target analyte.

4. The method according to claim 3, wherein one sample is a test sample and a calibration sample is provided for each different analyte, wherein each calibration sample comprises one or more different aliquots of a target analyte, wherein the test sample and each aliquot of each calibration sample are differentially labelled.

5. The method according to claim 2, wherein the calibration sample comprises two or more different aliquots of the target analyte.

6. The method according to claim 1, wherein the plurality of samples comprise a plurality of test samples and a calibration sample, wherein the calibration sample comprises one or more aliquots of the target analyte, each aliquot having a known quantity of the analyte, wherein the test sample and each aliquot of the calibration sample are differentially labelled.

7. The method according to claim 6, wherein each of the plurality of test samples is assayed for the same analyte.

8. The method according to claim 7, wherein each test sample is differentially labelled with one or more of the isobaric mass labels.

9. A method according to claim 6, wherein the method comprises a further step prior to step (a) of differentially labelling each test sample and each aliquot of the calibration sample with one or more isobaric mass labels.

10. A method according to claim 9, which comprises a further step of combining the differentially labelled aliquots to produce a calibration sample prior to step (a).

11. The method according to claim 1, wherein the plurality of samples are test samples.

12. The method according to claim 1, wherein the quantity determined in step (h) is one of the relative quantity or absolute quantity of the target analyte in each sample.

13. The method according to claim 1, wherein the method comprises a further step after step (d) of producing a mass spectrum of the plurality of fragment ions from step (d).

14. The method according to claim 13, wherein the identity of the target analyte is determined by identifying one or more fragment ions characteristic of the target analyte in the mass spectrum.

15. The method according to claim 1, wherein in step (c) the first mass to charge ratio is equivalent to the mass to charge ratio of the unfragmented parent ion of the target analyte labelled with a specific number of mass labels.

16. The method according to claim 1, wherein in step (c) the first mass to charge ratio is equivalent to the mass to charge ratio of a fragment ion of the target analyte labelled with a specific number of mass labels.

17. The method according to claim 1, wherein in step (e) the second mass to charge ratio is the mass to charge ratio of one of a $y_2$ to $y_n$ series ion comprising an intact mass label.

18. The method according to claim 1, wherein in step (e) the second mass to charge ratio is the mass to charge ratio of one of a b-series ion comprising an intact mass label.

19. The method according to claim 17 or claim 18, wherein the $y_2$ to $y_n$ series ion or b-series ion has a higher mass to charge ratio compared to the first mass to charge ratio selected in step (c).

20. The method according to claim 1, wherein the target analyte is selected from a protein, a polypeptide, a peptide an amino acid or a nucleic acid, or fragments thereof.

21. The method according to claim 1, wherein steps (c) to (g) are carried out in separate quadrupoles in a mass spectrometer.

22. The method according to claim 1, wherein steps (c) to (g) are carried out sequentially in the same zone of a mass spectrometer.

23. The method according to claim 1, wherein one of the samples comprises a trigger aliquot which comprises a trigger analyte and the method comprises a further step after step (b) and prior to step (c) of detecting ions having a mass to charge ratio equivalent to the mass to charge ratio of the trigger analyte, wherein when ions having a mass to charge ratio equivalent to the mass to charge ratio of the trigger analyte are detected step (c) is initiated.

24. A method according to claim 23, wherein the trigger analyte in the trigger aliquot is labelled with an isobaric mass label.

25. The method according to claim 23, wherein the trigger analyte in the trigger aliquot is labelled with a mass label which is chemically identical to but isotopically distinct and differing in mass from the isobaric mass labels of the other analytes in the samples.

26. A method according to claim 1, wherein the mass label comprises the following structure:

X-L-M wherein X is a mass marker moiety comprising the following group:

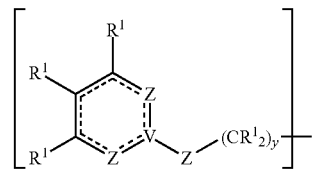

wherein the cyclic unit is aromatic or aliphatic and comprises from 0-3 double bonds; each Z is independently N, $N(R^1)$, $C(R^1)$, CO, $CO(R^1)$, $C(R^1)_2$, O or S; V is N, C or $C(R^1)$; each $R^1$ is independently H, a substituted or unsubstituted straight or branched C1-C6 alkyl group, a substituted or unsubstituted aliphatic cyclic group, a substituted or unsubstituted aromatic group or a substituted or unsubstituted heterocyclic group; and y is an integer from 0-10, L is a cleavable linker and M is a mass normalisation moiety.

27. A method according to claim 26, wherein the cleavable linker attaching the mass marker moiety to the mass normalisation moiety is a linker cleavable by collision.

28. A method according to claim 27, wherein the linker is cleavable by CID, ETD, ECD or SID using mass spectrometry.

29. A method according to claim 9, wherein the labelling step comprises a step of reacting the analyte with a reactive mass label, wherein the reactive mass label comprises the mass label and a reactive functionality.

30. A method according to claim 29, wherein the reactive functionality is capable of reacting with any amino group on a polypeptide and comprises a nucleophile or an electrophile.

31. A method according to claim 29 or claim 30, wherein the reactive functionality comprises the following group:

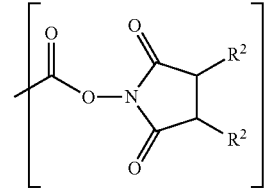

wherein each $R^2$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group.

32. A method according to claim 26, wherein the mass label is from a set of two or more mass labels, wherein the mass normalisation moiety ensures that the mass label has a desired aggregate mass, and wherein the mass marker moiety of each mass label in the set has a mass different from that of each other mass marker moiety in the set, and wherein each mass label in the set has a common aggregate mass, and wherein each mass label in the set is distinguishable from each other by mass spectroscopy.

33. A method according to claim 32, wherein each mass label in the set has a mass adjuster moiety, selected from:
   (a) an isotopic substituent situated within one or more of the mass marker moiety and the mass normalisation moiety, and
   (b) substituent atoms or groups attached to one or more of the mass marker moiety and the mass normalisation moiety.

34. A method according to claim 33, wherein the mass adjuster moiety is selected from a halogen atom substituent, a methyl group substituent, and $^2H$, $^{15}N$, $^{13}C$ or $18O$ isotopic substituents.

35. A method according to claim 34, wherein the mass adjuster moiety is $^{15}N$ or $^{13}C$ and the set comprises two mass labels having the following structures:

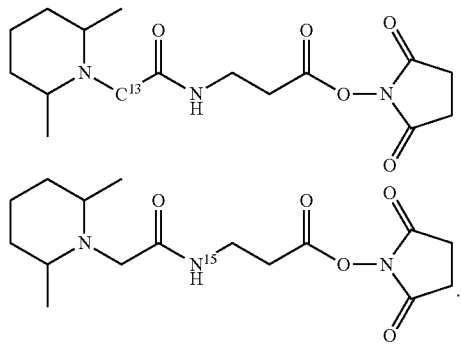

36. A method according to claim 34, wherein the mass adjuster moiety is $^{15}N$ and $^{13}C$ and the set comprises five mass labels having the following structures:

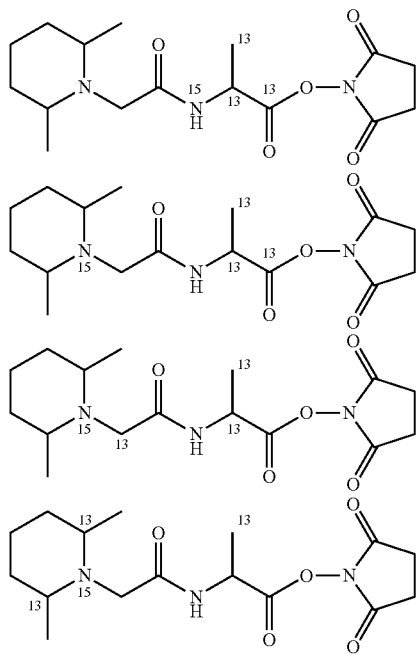

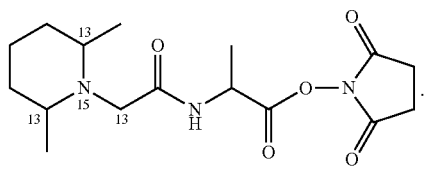

37. A method according to claim 34, wherein the mass adjuster moiety is $^{15}N$ and $^{13}C$ and the set comprises six mass labels having the following structures:

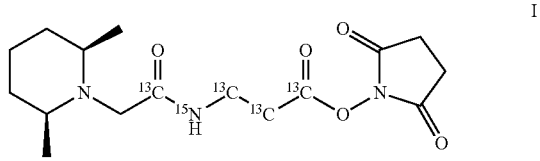

I

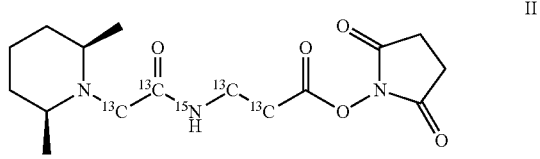

II

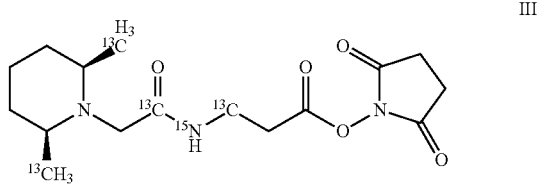

III

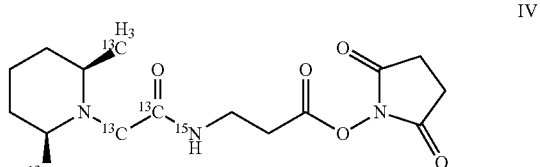

IV

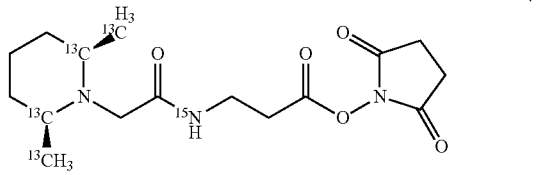

V

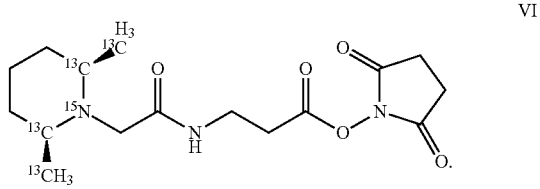

VI

* * * * *